(12) United States Patent
Rapaport et al.

(10) Patent No.: US 10,799,462 B2
(45) Date of Patent: Oct. 13, 2020

(54) PEPTIDE-POLYPEPTIDE CO-ASSEMBLED NANOPARTICLES FOR DRUG DELIVERY

(71) Applicant: B. G. Negev Technologies and Applications Ltd., at Ben-Gurion University, Beer-Sheva (IL)

(72) Inventors: Hanna Rapaport, Lehavim (IL); Ifat Cohen, Beer Sheva (IL)

(73) Assignee: B. G. Negev Technologies and Applications Ltd., at Ben-Gurion University, Beer-Sheva (IL)

( * ) Notice: Subject to any disclaimer, the term of this patent is extended or adjusted under 35 U.S.C. 154(b) by 316 days.

(21) Appl. No.: 15/310,286

(22) PCT Filed: May 13, 2015

(86) PCT No.: PCT/IL2015/050505
§ 371 (c)(1),
(2) Date: Nov. 10, 2016

(87) PCT Pub. No.: WO2015/173818
PCT Pub. Date: Nov. 19, 2015

(65) Prior Publication Data
US 2017/0258735 A1    Sep. 14, 2017

Related U.S. Application Data

(60) Provisional application No. 61/992,258, filed on May 13, 2014.

(51) Int. Cl.
| | | |
|---|---|---|
| *A61K 9/51* | (2006.01) | |
| *A61K 9/00* | (2006.01) | |
| *A61K 31/416* | (2006.01) | |
| *A61K 31/4706* | (2006.01) | |
| *A61K 9/10* | (2006.01) | |
| *A61K 31/704* | (2006.01) | |
| *A61K 9/127* | (2006.01) | |
| *A61K 47/42* | (2017.01) | |
| *B82Y 40/00* | (2011.01) | |
| *B82Y 5/00* | (2011.01) | |

(52) U.S. Cl.
CPC .............. *A61K 9/51* (2013.01); *A61K 9/0019* (2013.01); *A61K 9/10* (2013.01); *A61K 9/1273* (2013.01); *A61K 9/5146* (2013.01); *A61K 9/5192* (2013.01); *A61K 31/416* (2013.01); *A61K 31/4706* (2013.01); *A61K 31/704* (2013.01); *A61K 47/42* (2013.01); *B82Y 5/00* (2013.01); *B82Y 40/00* (2013.01)

(58) Field of Classification Search
CPC ...................................................... A61K 9/51
See application file for complete search history.

(56) References Cited

U.S. PATENT DOCUMENTS 5,904,936 A    5/1999   Huille et al.

FOREIGN PATENT DOCUMENTS

| WO | 2007/148334 A1 | 12/2007 |
|---|---|---|
| WO | 2009/079066 A2 | 6/2009 |
| WO | 2013/004716 A1 | 1/2013 |
| WO | 2013/123298 A1 | 8/2013 |

OTHER PUBLICATIONS

Guo (Mitofusin 2 Triggers Vascular Smooth Muscle Cell Apoptosis via Mitochondrial Death Pathway, Circ Res. 2007;101:1113-1122) (Year: 2007).*
You (You (Efficient gene transfection using chitosan-alginate core-shell nanoparticles, International Journal of Nanomedicine 2006: 1(2) 173-180)2006:1(2) 173-180) (Year: 2006).*
Hashida (Development of a Novel Composite Material with Carbon Nanotubes Assisted by Self-Assembled Peptides Designed in Conjunction with β-Sheet Formation, Journal of Pharmaceutical Sciences 2012, vol. 101) (Year: 2012).*
Shamsir (b-Sheet Containment by Flanking Prolines: Molecular Dynamic Simulations of the Inhibition of b-Sheet Elongation by Proline Residues in Human Prion Protein, Biophysical Journal vol. 92 Mar. 2007 2080-2089) (Year: 2007).*
Aggeli et al., (1997) Responsive gels formed by the spontaneous self-assembly of peptides into polymeric beta-sheet tapes. Nature, 386(6622), 259-262.
Akagi et al., (2005) Preparation and characterization of biodegradable nanoparticles based on poly (γ-glutamic acid) with I-phenylalanine as a protein carrier. Journal of Controlled Release, 108(2), 226-236.

(Continued)

*Primary Examiner* — Andrew D Kosar
*Assistant Examiner* — Khalid Kader
(74) *Attorney, Agent, or Firm* — J.A. Lindeman & Co. PLLC

(57) ABSTRACT

Provided are co-assembled nanoparticles including at least one polypeptide including a polyanion; and at least one amphiphilic peptide capable of forming a β-sheet structure, a derivative or a salt thereof, the amphiphilic peptide including at least 2 pairs of alternating hydrophobic/hydrophilic amino acid residues in which the hydrophilic amino acid residue is positively charged, and methods of preparation of the nanoparticles. Further provided are pharmaceutical compositions including the co-assembled nanoparticles and a pharmaceutically active ingredient, dissolved, entrapped, encapsulated or attached to the co-assembled nanoparticles. Further provided are therapeutic uses of the pharmaceutical compositions.

20 Claims, 21 Drawing Sheets

Specification includes a Sequence Listing.

(56) References Cited

OTHER PUBLICATIONS

Akita et al., (2009) Multi-layered nanoparticles for penetrating the endosome and nuclear membrane via a step-wise membrane fusion process. Biomaterials, 30(15), 2940-2949.
Bawa et al., (2012) Self-assembling peptide-based nanoparticles enhance cellular delivery of the hydrophobic anticancer drug ellipticine through caveolae-dependent endocytosis. Nanomedicine: Nanotechnology, Biology and Medicine, 8(5), 647-654.
Brannon-Peppas et al., (2012) Nanoparticle and targeted systems for cancer therapy. Advanced drug delivery reviews, 64, 206-212.
Breunig et al., (2008) Polymers and nanoparticles: intelligent tools for intracellular targeting?. European Journal of Pharmaceutics and Biopharmaceutics, 68(1), 112-128.
Cai et al., (2011) Self-assembly of polypeptide-based copolymers into diverse aggregates. Chemical Communications, 47(40), 11189-11203.
Degrado et al., (1985). Induction of peptide conformation at apolar water interfaces. 1. A study with model peptides of defined hydrophobic periodicity. Journal of the American Chemical Society, 107(25), 7684-7689.
Dias et al., (2005) Drugs targeting mitochondrial functions to control tumor cell growth. Biochemical pharmacology, 70(1), 1-12.
El-Sayed et al., (2009) Delivery of macromolecules using arginine-rich cell-penetrating peptides: ways to overcome endosomal entrapment. The AAPS journal, 11(1), 13-22.
Fulda et al., (2010) Targeting mitochondria for cancer therapy. Nature reviews Drug discovery, 9(6), 447-464.
Fung et al., (2007) Formation of colloidal suspension of hydrophobic compounds with an amphiphilic self-assembling peptide. Colloids and Surfaces B: Biointerfaces, 55(2), 200-211.
Fung et al., (2009) Self-Assembling Peptide as a Potential Carrier for Hydrophobic Anticancer Drug Ellipticine: Complexation, Release and In Vitro Delivery. Advanced functional materials, 19(1), 74-83.
Fung et al., (2011) The potential of nanoscale combinations of self-assembling peptides and amino acids of the Src tyrosine kinase inhibitor in acute lung injury therapy. Biomaterials, 32(16), 4000-4008.
Futaki et al., (2001) Arginine-rich peptides An abundant source of membrane-permeable peptides having potential as carriers for intracellular protein delivery. Journal of Biological Chemistry, 276(8), 5836-5840.
Gamboa-Vujicic et al., (1993) Toxicity of the mitochondrial poison dequalinium chloride in a murine model system. Journal of pharmaceutical sciences, 82(3), 231-235.
Gazit, (2007) Self-assembled peptide nanostructures: the design of molecular building blocks and their technological utilization. Chemical Society Reviews, 36(8), 1263-1269.
Hamidi et al., (2008) Hydrogel nanoparticles in drug delivery. Advanced drug delivery reviews, 60(15), 1638-1649.
Husseini et al., (2008) Micelles and nanoparticles for ultrasonic drug and gene delivery. Advanced drug delivery reviews, 60(10), 1137-1152.
Kulterer et al., (2012) Functional polysaccharide composite nanoparticles from cellulose acetate and potential applications. Advanced Functional Materials, 22(8), 1749-1758.
Liu et al., (2008) Polysaccharides-based nanoparticles as drug delivery systems. Advanced drug delivery reviews, 60 (15), 1650-1662.
Marrache et al., (2012) Engineering of blended nanoparticle platform for delivery of mitochondria-acting therapeutics. Proceedings of the National Academy of Sciences, 109(40), 16288-16293.
Meade et al., (2007) Exogenous siRNA delivery using peptide transduction domains/cell penetrating peptides. Advanced drug delivery reviews, 59(2), 134-140.
Mo et al., (2012) Multistage pH-Responsive Liposomes for Mitochondrial-Targeted Anticancer Drug Delivery. Advanced materials, 24(27), 3659-3665.
Mikhopadhyay et al., (2007) Delivery of drugs and macromolecules to mitochondria. Advanced drug delivery reviews, 59(8), 729-738.
Murphy et al., (2000) Drug delivery to mitochondria: the key to mitochondrial medicine. Advanced drug delivery reviews, 41(2), 235-250.
Neupert, (1997) Protein import into mitochondria. Annual review of biochemistry, 66(1), 863-917.
Neupert et al., (2007) Translocation of proteins into mitochondria. Annu. Rev. Biochem., 76, 723-749.
Oppermann et al., (1998) Biodegradation of polyamides. Polymer degradation and stability, 59(1), 337-344.
Rajagopal et al., (2004) Self-assembling peptides and proteins for nanotechnological applications. Current opinion in structural biology, 14(4), 480-486.
Rapaport et al., (2000) Two-dimensional order in β-sheet peptide monolayers. Journal of the American Chemical Society, 122(50), 12523-12529.
Schneider et al., (2002) Responsive hydrogels from the intramolecular folding and self-assembly of a designed peptide. Journal of the American Chemical Society, 124(50), 15030-15037.
Schroeder et al., (2009) Peptide nanoparticles serve as a powerful platform for the immunogenic dsplay of poorly antigenic actin determinants. Journal of molecular biology, 386(5), 1368-1381.
Shen et al., (2012) Polyampholyte Nanoparticles Prepared by Self-Complexation of Cationized Poly (γ-glutamic acid) for Protein Carriers. Macromolecular bioscience, 12(8), 1100-1105.
Shima et al., (2014) The role of hydrophobicity in the disruption of erythrocyte membrane by nanoparticles composed of hydrophobically modified poly (γ-glutamic acid). Journal of Biomaterials Science, Polymer Edition, 25(2), 203-210.
Sung et al., (2005) Natural and edible biopolymer poly-γ-glutamic acid: synthesis, production, and applications. The Chemical Record, 5(6), 352-366.
Szeto, (2008) Mitochondria-targeted cytoprotective peptides for ischemia-reperfusion injury. Antioxidants & redox signaling, 10(3), 601-620.
Tang et al., (2010) Heparinized chitosan/poly (γ-glutamic acid) nanoparticles for multi-functional delivery of fibroblast growth factor and heparin. Biomaterials, 31(35), 9320-9332.
Tu et al., (2004) Bottom-up design of biomimetic assemblies. Advanced drug delivery reviews, 56(11), 1537-1563.
Ulijn et al., (2008) Designing peptide based nanomaterials. Chemical Society Reviews, 37(4), 664-675.
Verma et al., (2010) Effect of surface properties on nanoparticle-cell interactions. Small, 6(1), 12-21.
Vinod et al., (2013) Transparent, conductive, and SERS-active Au nanofiber films assembled on an amphiphilic peptide template. Nanoscale, 5(21), 10487-10493.
Wallace, (2012) Mitochondria and cancer. Nature Reviews Cancer, 12(10), 685-698.
Wang et al., (2008) Poly (γ-glutamic acid) nanoparticles as an efficient antigen delivery and adjuvant system: Potential for an AIDS vaccine. Journal of medical virology, 80(1), 11-19.
Weiss et al., (1987) Dequalinium, a topical antimicrobial agent, displays anticarcinoma activity based on selective mitochondrial accumulation. Proceedings of the National Academy of Sciences, 84(15), 5444-5448.
Wu et al., (2012) Self-assembling peptide-based nanoparticles enhance anticancer effect of ellipticine in vitro and in vivo. Int J Nanomedicine, 7(4), 3221-3233.
Yamada et al., (2012) Delivery of bioactive molecules to the mitochondrial genome using a membrane-fusing, liposome-based carrier, DF-MITO-Porter. Biomaterials, 33(5), 1589-1595.
You et al., (2006) Efficient gene transfection using chitosan-alginate core-shell nanoparticles. international Journal of nanomedicine, 1(2), 173-180.
Zhang et al., (1993) Spontaneous assembly of a self-complementary oligopeptide to form a stable macroscopic membrane. Proceedings of the National Academy of Sciences, 90(8), 3334-3338.
Zhang, (2003) Fabrication of novel biomaterials through molecular self-assembly. Nature biotechnology, 21(10), 1171-1178.
Field et al., ( 2015) Peptides for specifically targeting nanoparticles to cellular organelles: quo vadis? Acc Chem Res 48(5): 1380-1390.
Horton et al., (2008) Mitochondria-penetrating peptides. Chem Biol 15(4): 375-382.

(56) References Cited

OTHER PUBLICATIONS

Horton et al., (2012) Tuning the activity of mitochondria-penetrating peptides for delivery or disruption. Chembiochem 13(3): 476-485.
Kelley et al., (2011) Development of novel peptides for mitochondrial drug delivery: amino acids featuring delocalized lipophilic cations. Pharm Res 28(11): 2808-2819.
Lindgren et al., (2000) Cell-penetrating peptides. Trends Pharmacol Sci 21(3): 99-103.
Loo et al., (2012) From short peptides to nanofibers to macromolecular assemblies in biomedicine. Biotechnol Adv 30(3): 593-603.
Ruoslahti et al., (2010) Targeting of drugs and nanoparticles to tumors. J Cell Biol 188(6): 759-768.
Smith et al., (2011) Mitochondria-targeted small molecule therapeutics and probes. Antioxid Redox Signal 15(12): 3021-3038.

\* cited by examiner

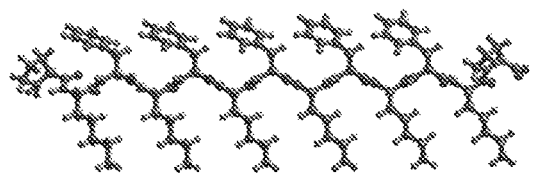
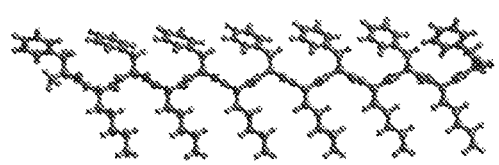
Figure 1a
Figure 1b
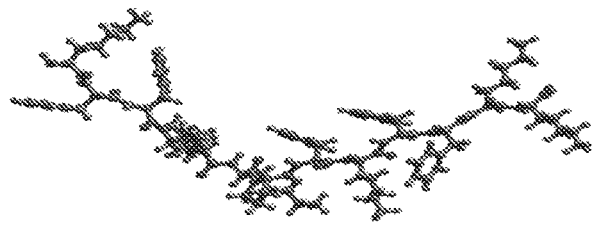
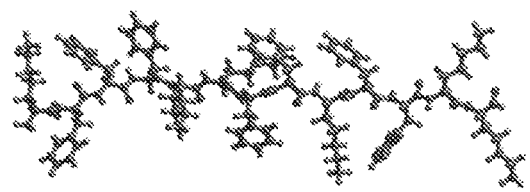
Figure 1c
Figure 1d

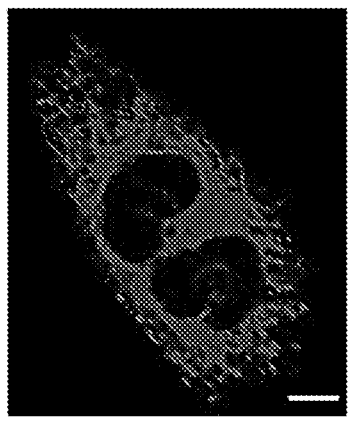 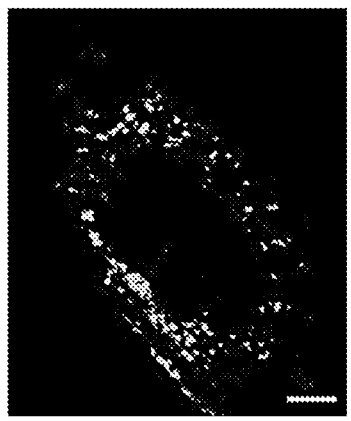 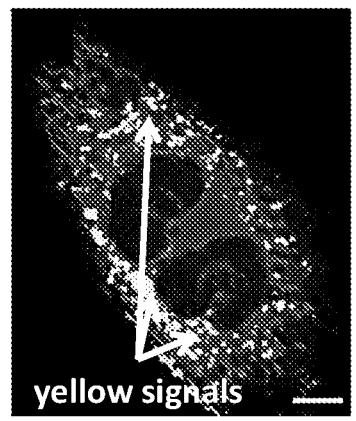
Figure 15a　　Figure 15b　　Figure 15c
 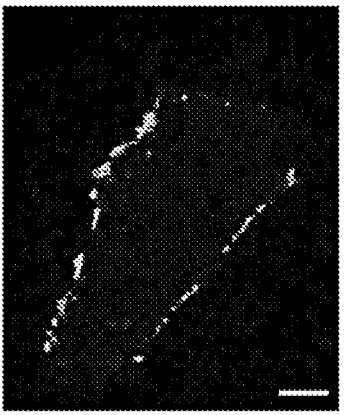 
Figure 15d　　Figure 15e　　Figure 15f

PEPTIDE-POLYPEPTIDE CO-ASSEMBLED NANOPARTICLES FOR DRUG DELIVERY

SEQUENCE LISTING

The Sequence Listing submitted in text format (.txt) filed on Feb. 22, 2019, named "SequenceListing.txt", created on Feb. 22, 2019, 6.82 KB), is incorporated herein by reference.

FIELD OF INVENTION

The present invention relates to peptide-polypeptide co-assembled nanoparticles for intracellular delivery of active ingredients. The present invention further provides methods of preparation and therapeutic uses of said nanoparticles.

BACKGROUND OF THE INVENTION

Effectiveness of drugs highly depends on drug delivery to the proper organ and cell types, and even on delivery to a specific location within the cell. In order to deliver a therapeutic agent to the desired site within the patient body, targeted drug delivery can be employed. Targeted drug delivery not only increases the effectiveness of the therapeutic agent by delivering it to the designated organ or cell type, but also allows delivering higher doses of the drug, while maintaining the required plasma and tissue drug levels in the body, thereby preventing any damage to the healthy tissue. Targeted drug delivery requires use of delivery vehicles, which have to be biocompatible and biodegradable, to have suitable size and high loading capacity, provide extended circulation time, and be capable of accumulating at required pathological sites in the body.

Pharmaceutical nanotechnology allows the creation of nanocarriers such as nanoparticles, nanocapsules, micellar systems, and conjugates. Nanoparticles are efficient drugs carriers for drug delivery applications. Nanoparticles can pass through the smallest capillary vessels because of their ultra-tiny size. They can penetrate cells and tissue gap to arrive at target organs such as liver, spleen, lung, spinal cord and lymph. Nanoparticles can further be designed to provide controlled release of the active ingredient based on the biodegradability, pH, ion and/or temperature sensibility of the nanoparticle materials. Thus, nanoparticle drug delivery systems can improve the utility of drugs and reduce toxic side effects [Liu Z et al., Adv Drug Deliv Rev. 2008; 60(15):1650-62].

During the formation of nanoparticles the drug is dissolved, entrapped, encapsulated or attached to a nanoparticle matrix. Nanoparticles may be formed by inorganic and organic materials, liposomes, micelles and polymeric materials. Nanoparticles can be designed to control where and when the drug will be released, by strategies that involve incorporation of specific amino acids or peptides [Breunig M et al., European Journal of Pharmaceutics and Biopharmaceutics, 2008; 68(1):112-28].

Numerous strategies for creating nanoparticles combine the use of biopolymers. Among the natural polymeric materials polysaccharides are the most popular polymer for drug delivery applications. Polysaccharides have wide diversity in structure and property due to a large number of reactive groups, a wide range of molecular weight (MW) and varying chemical composition. As natural biomaterials, polysaccharides are highly stable, safe, non-toxic and biodegradable. For example, You et al. used chitosan to prepare a chitosan-alginate core-shell nanoparticle, wherein the positive charges of chitosan interact with negative plasmid [You J et al., International Journal of Nanomedicine. 2006; 1(2): 173-80].

Another kind of polymer that can be used in a formation of nanoparticles is a polypeptide. Polypeptides are promising for preparing bio-related materials due to their excellent biocompatibility and biodegradability. Poly gamma glutamic acid (γ-PGA) is an anionic polypeptide, which is soluble in water, nontoxic, biodegradable and hydrophilic. Wang X. et al., used γ-PGA to prepare ovalbumin-encapsulating nanoparticles for antigen delivery [Wang X et al., J Med Virol. 2008 January; 80(1):11-9]. In another study, nanoparticles composed of chitosan (CS) and γ-PGA were prepared to carry basic fibroblast growth factors (bFGF) to wound tissue. CS/γ-PGA nanoparticles with heparin are pH sensitive and can release bFGF upon the increase in the pH and subsequent deprotonation of the amino groups of chitosan, as the electrostatic interaction between negative carboxylic groups in γ-PGA and positive amino groups in chitosan decreases [Tang D et al., Biomaterials. 2010; 31(35):9320-32].

Another strategy is the use of a polyampholyte—a polyelectrolyte composed of anionic and cationic groups on different monomer units within the same polymer. Polyampholytes that are composed of poly amino acid can create self-assembly nanostructured materials by inter and intra interactions, such as electrostatic interactions, hydrogen bonds and hydrophobic interactions. Charged polyampholyte nanoparticles were prepared from γ-PGA-Arg by intra-/inter-molecular electrostatic interactions when the polymer was dispersed in water [Shen H. et al., Macromolecular Bioscience. 2012; 12(8): 1100-5]

Peptides have a huge potential for drug delivery applications, due to the natural propensity of many peptides for penetrating into the cell. Also peptides are nontoxic and biodegradable. Peptide-based delivery systems have shown the potential to deliver therapeutic proteins, bioactive peptides, small molecules and nucleic acids. Moreover, it is possible to design peptides with unique properties such as amphiphilic structure and a self-assembly capability, allowing them to encapsulate both hydrophobic drugs and hydrophilic proteins and oligonucleotides. For example, nanoparticles made from EAK16-II amphiphilic peptides have shown the ability to stabilize anticancer hydrophobic drug ellipticine (EPT) [Fong S. Y. et al., Advanced functional materials. 2008; 19(1):74-83]. Said peptides have a beta sheet structure that is composed from nanofibers stabilized by hydrogen bonds, ionic complementary and hydrophobic interactions, wherein the hydrophobic residues of the peptide can interact with the hydrophobic drug and the hydrophilic residues can stabilize the drug-peptide complex by hydrogen bonds [Zhang S. et al., Proceedings of the National Academy of Sciences. 1993; 90(8):3334-8].

Nanoparticles can be taken by the reticuleondothelial system (such as liver and spleen) depending on their size, hydrophobicity and surface charge. Hydrophilic nanoparticles have been show to avoid the reticuleondothelial system and found to be circulating in the blood stream for longer periods of time. It has been also shown that nanoparticles should have a particle size of 100 nm or less in order to circulate in the blood stream. Small hydrophilic nanoparticles can thus be beneficially used for delivery of anti-cancer agents to tumors, as particles with longer circulation time have better chances to target tumor cells. Additionally, nanoparticles can extravasate into tumors interstitial space through the gaps between endothelial cells.

The potential of nanoparticles to improve any therapy lies in their ability to deliver payloads directly to the cells of interest and simultaneously enhance stability and pharmacokinetics. However, an equally important consideration is whether the same nanoparticle can deliver the therapeutic payload to the intended target inside the cells.

Mitochondria are promising targets within the cell due to the fact that damage to mitochondria leads to a range of human disorders. Many parameters are regulated by the mitochondria, such as energy production, modulation of oxidation-reduction (redox) status, generation of reactive oxygen species (ROS), cytosolic calcium ($Ca^{2+}$) levels, and initiation of apoptosis. Changes in one of each can lead to damage on biosynthetic pathways, cellular signal transduction pathways, transcription factors and chromatin structure; these processes can shift the cell from differentiated state to proliferating state and eventually lead to cancer. Additionally, mitochondria play an important role in processes related to oxidative damage, calcium metabolism, diabetes and obesity.

Mitochondria have their own DNA (mtDNA). Mutation in mtDNA occurs at a high rate and forms a mixture of normal and mutant mtDNA in cells. An increase in mutant mtDNA compared to normal mtDNA can lead to cancer. Many of mtDNA mutations in cancer are associated with oxidative phosphorylation and the regulation of ROS. Mitochondria of cancer cells are different from normal cells in structure and function. Moreover cancer cells are more sensitive to mitochondrial changes. Based on these differences, mitochondrially-targeted agents can be designed to selectively target tumors.

Due to the complexity in the structure of mitochondria it is necessary to use different strategies to allow drugs and macromolecules get into mitochondria. For successful delivery of carriers into mitochondria, the carrier must overcome few challenges. First, the carrier has to enter the cell and then through the intracellular space into the mitochondria or the nucleus. During these passages the carrier passes several membranes such as plasma, endosome and mitochondria or nucleus membrane.

One way to overcome the membrane barrier is by binding the carrier to cell penetrating peptides (CPPs). CPPs are short peptides that can penetrate the cell membrane alone or attached to bulky cargos such as peptides, proteins, oligonucleotides, pDNA or liposomes. Arginine-rich cell-penetrating peptides (AR-CPPs) were used to induce endosomal escape at natural and acidic pH [El-Sayed A et al., The AAPS journal 2009; 11(1):13-22].

Mitochondria-targeted cytoprotective peptides, which were originally designed by Hazel H. Szeto and Peter W. Schiller, and are hence designated SS peptides, are small, water-soluble, peptides limited to 10 amino acid residues, wherein common to these peptides is an alternating aromatic cationic motif, with the basic amino acid residues (such as Arg and Lys) providing two positive charges. The free amine of the N-terminus of these peptides provides a third positive charge because the C-terminus has been amidated. This aromatic cationic motif allows them to freely penetrate cells despite carrying a 3+ net charge at physiologic pH [H. H. Szeto, Antioxidants & Redox Signaling, Volume 10, Number 3, 2008].

Nanoparticles that overcome the challenges explained hereinabove were developed by Akita et al. and by Yamada and colleagues. Said nanoparticles were composed of DNase covered with two membrane envelopes, a mitochondria-fusogenic lipid envelope (inner) and an endosome-fusogenic lipid envelope (outer) [Akita H. et al., Biomaterials. 2009; 30(15):2940-9, and Yamada Y. et al., Biomaterials. 2012; 33(5):1589-95].

Another approach towards synthesis of the nanoparticles capable of penetrating mitochondria membrane barriers is coupling of biodegradable polymer with a liphophilic cation, which can cross into the mitochondrial matrix space. Marrache et al. synthesized a PLGA-b-PEG copolymer with a single terminal liphophilic triphenylphosphonium (TPP) cation, which is capable of encapsulating various mitochondria-acting drugs and delivering said drugs to the mitochondria [Marrache S. et al., PNAS, 2012; 109(40); 16288-16293].

International Patent Application No. WO 2013/123298 to Marrache et al. is directed to a nanoparticle, comprising a hydrophobic nanoparticle core, a hydrophilic layer surrounding the core and a mitochondrial targeting moiety, wherein the nanoparticle has a diameter of about 200 nanometers or less and has a zeta potential of about 0 mV or greater.

Another challenge that needs to be overcome in systems designed to target the mitochondria is the differences in pH values along the delivery path. The carrier that enters the cell through endocytosis has to be stable in the endosome, where the pH is 5-6, and cytoplasm, and needs to be released together with the drug it carries in the mitochondria. The carrier may also enter the lysosome where the pH is even lower, 4-5, due to endolysosomal acids. Drugs that are not stable in acidic conditions might undergo degradation and hydrolysis in lysosome, which is undesired. The carrier must then escape to the cytoplasm where the pH is neutral and finally reach the mitochondria that are mildly basic. The difference in pH values can influence the stability of particles especially of those that are stabilized by electrostatic interactions.

Ran Mo et el. suggested mitochondria-targeted nanoparticles based on zwitterionic oligopeptide liposomes that overcome this challenge by a multistage pH response. This carrier consists of soy phosphatidylcholine (SPC), cholesterol, and a synthetic smart lipid that carries two amino acid groups (glutamic acid and histidine) and one pH-cleavable group (hexahydrobenzoic amide) as a hydrophilic block, and two stearyl alkane chains as a hydrophobic block [Mo R. et al., Adv Mater. 2012,17; 24(27):3659-65].

There still remains an unmet need for simple and efficient drug carriers adapted to provide intracellular delivery of various active ingredients. Ideal mitochondria-targeted nanoparticles should be capable of encapsulating and protecting the therapeutic agent, penetrating through cellular membranes and being stable in a wide pH range.

SUMMARY OF THE INVENTION

The present invention is directed to peptide-polypeptide co-assembled nanoparticles (NPs) for drug delivery. The self-assembly of the nanoparticles of the present invention is based on electrostatic interactions between positively charged amino groups of the peptide and negatively charged carboxylic groups of the polypeptide. A combination of the polypeptide and peptide allows not only to encapsulate a therapeutically active agent and deliver it to a cell or an organelle within the cell, but also to modify the nanoparticles physical properties, such as particle size, surface charge or the active ingredient loading capacity. These and other physical properties of the nanoparticle can be fine-tuned in order to fit the delivery system to a specific pharmaceutically active agent or to a specific target.

The present invention is based in part on a surprising finding that nanoparticles comprising a designed and synthetic self-assembled peptide co-assembled with a polypeptide can serve as efficient delivery vehicles of amphiphilic and/or charged drugs into the mitochondria. Specific amino acid sequences have been designed in order to induce well-defined secondary structures that may interact spontaneously via various non-covalent bonds to form hierarchically ordered assemblies. Specifically, amphiphilic peptides were designed to be capable of forming a charged β-sheet secondary structure, using periodic alternation of hydrophobic and hydrophilic amino acids. The nanoparticles comprising said charged-amphiphilic peptides and a native polypeptide can be designed to be stable in various pH environments, corresponding to endosomal, physiological and mitochondrial pH. The relative concentration of the components of the nanoparticles and the structure thereof were further varied in order to obtain the desired particle size and the active ingredient loading capacity. It has been further surprisingly found that the surface charge of the designed nanoparticles can be easily altered with peptide coatings, allowing modifying the cell penetration properties of the drug delivery nanoparticles.

As disclosed herein for the first time, the nanoparticles comprising a co-assembled combination of an amphiphilic peptide capable of forming a positively charged β-sheet structure and a polyanionic polypeptide were found to encapsulate amphiphilic and charged chemotherapeutic drugs, extending half-life thereof and enabling their efficient intracellular delivery to the mitochondria, thereby increasing the potency of the anticancer therapy.

Therefore, according to one aspect, the invention provides a co-assembled nanoparticle comprising at least one polypeptide comprising a polyanion; and at least one amphiphilic peptide capable of forming a β-sheet structure, a derivative or a salt thereof, the amphiphilic peptide comprising at least 2 pairs of alternating hydrophobic/hydrophilic amino acid residues, wherein the hydrophilic amino acid residue is positively charged.

According to some embodiments, the at least 2 pairs of alternating hydrophobic/hydrophilic amino acid residues are identical.

In some embodiments, the at least one amphiphilic peptide comprises at least one terminal Pro residue. In additional embodiments, the at least one amphiphilic peptide comprises two terminal Pro residues.

According to some embodiments, the at least one amphiphilic peptide of the co-assembled nanoparticle comprises 2-20 pairs of alternating hydrophobic/hydrophilic amino acid residues. According to further embodiments, the at least one amphiphilic peptide of the co-assembled nanoparticle comprises 4-20 pairs of alternating hydrophobic/hydrophilic amino acid residues. According to yet further embodiments, the at least one amphiphilic peptide of the co-assembled nanoparticle comprises 5-20 pairs of alternating hydrophobic/hydrophilic amino acid residues. According to still further embodiments, the at least one amphiphilic peptide of the co-assembled nanoparticle comprises at least 5 pairs of alternating hydrophobic/hydrophilic amino acid residues.

According to further embodiments, the at least one amphiphilic peptide is 4-40 amino acids in length. According to still further embodiments, the at least one amphiphilic peptide is 7-30 amino acids in length. According to yet further embodiments, the at least one amphiphilic peptide is at least 10 amino acids in length. According to still further embodiments, the at least one amphiphilic peptide is 10-20 amino acids in length. According to yet further embodiments, the at least one amphiphilic peptide is 10-15 amino acids in length. According to still further embodiments, the at least one amphiphilic peptide is 11-15 amino acids in length. According to yet further embodiments, the at least one amphiphilic peptide is 13 amino acids in length. According to additional embodiments, the at least one amphiphilic peptide comprises n hydrophobic residues and n+1 hydrophilic residues, wherein n designates an integer of 2-20.

The hydrophobic amino acid residue can be selected from the group consisting of Trp, Phe, Leu, Ile, Val and Ala. Each possibility represents a separate embodiment of the invention. In some embodiments, the hydrophobic amino acid residue is Phe, Leu or Val. In a certain embodiment, the hydrophobic amino acid residue is Phe.

The hydrophilic amino acid residue can be selected from the group consisting of Lys and Arg. Each possibility represents a separate embodiment of the invention. In a certain embodiment, the hydrophilic amino acid residue is Lys.

According to some embodiments, the at least one amphiphilic peptide comprises an amino acid sequence according to Formula I:

X-(hydrophobic-hydrophilic)$_n$-B       (Formula I)

wherein n designates an integer of 2-20, hydrophobic designates a hydrophobic amino acid residue, hydrophilic designates a hydrophilic amino acid residue, X designates Pro, Pro-hydrophilic amino acid residue or represents the peptide's amino terminus, and B is Pro or represents the peptide's carboxy terminus. According to further embodiments, the at least one amphiphilic peptide comprises an amino acid sequence Pro-Lys-(Phe-Lys)$_n$-Pro, wherein n is an integer of 2-7 (SEQ ID Nos: 2, 4, 6, 8, 10, and 12). According to yet further embodiments, the at least one amphiphilic peptide comprises an amino acid sequence Pro-Lys-(Phe-Lys)$_n$-Pro, wherein n is an integer of 3-7 (SEQ ID Nos: 2, 4, 6, 10, and 12). According to still further embodiments, the at least one amphiphilic peptide comprises an amino acid sequence Pro-Lys-(Phe-Lys)$_n$-Pro, wherein n is an integer of 4-6 (SEQ ID Nos: 2, 4, and 10).

According to various embodiments of the invention, the amphiphilic peptide comprises an amino acid sequence selected from SEQ ID NO:1-SEQ ID NO:12, or a peptide matrix thereof. In certain embodiments, the amphiphilic peptide has an amino acid sequence selected from the group consisting of SEQ ID NO:2, SEQ ID NO:4, SEQ ID NO:6, SEQ ID NO:8, SEQ ID NO:10, and SEQ ID NO:12. In some exemplary embodiments, the amphiphilic peptide has an amino acid sequence selected from SEQ ID NO:1 or SEQ ID NO:2. Thus, in some embodiments, the amphiphilic peptide is FK(FK)$_5$F (SEQ ID NO: 1, also termed herein "FK"). In other embodiments, the amphiphilic peptide is PK(FK)$_5$P (SEQ ID NO: 2, also termed herein "PFK").

The polypeptide of the co-assembled nanoparticle can comprise glutamic acid residues or polyaspartic acid residues. Each possibility represents a separate embodiment of the invention. In further embodiments, the polypeptide comprises glutamic acid residues. In a certain embodiment, the polypeptide is a poly(gamma-glutamic acid). In another embodiment, the polypeptide is a polyaspartic acid.

In some embodiments, the poly(gamma-glutamic acid) has a molecular weight of about 200-500 KDa.

In certain embodiments, the co-assembled nanoparticles comprise an amphiphilic peptide having an amino acid sequence selected from the group consisting of SEQ ID NO:2, SEQ ID NO:4, SEQ ID NO:6, SEQ ID NO:8, SEQ ID NO:10, and SEQ ID NO:12, and poly(gamma-glutamic acid).

In some embodiments, the co-assembled nanoparticles comprise PK(FK)$_5$P and poly(gamma-glutamic acid). In other embodiments, the co-assembled nanoparticles comprise FK(FK)$_5$F and poly(gamma-glutamic acid).

According to some embodiments, the weight ratio between the peptide and the polypeptide in the co-assembled nanoparticle is from about 0.2:1 to about 2:1. In a certain embodiment, said weight ratio is about 1:1. According to further embodiments, the molar ratio between the peptide and the polypeptide in the co-assembled nanoparticle is from about 40:1 to about 200:1. According to yet further embodiments, the ratio between the positive charge of the peptide and the negative charge of the polypeptide is from about 1:10 to about 1:1.

According to some embodiments, the co-assembled nanoparticles of the present invention have a spherical shape. According to additional embodiments, the co-assembled nanoparticles have an isotropically spherical shape.

Preferably, the mean particle size of the co-assembled nanoparticle is above 5 nm. According to some embodiments, the mean particle size is above 10 nm. In further embodiments, the co-assembled nanoparticle has a mean particle size in the range of about 10-100 nm. In still further embodiments, the co-assembled nanoparticle has a mean particle size in the range of about 10-50 nm. In yet further embodiments, the co-assembled nanoparticle has a mean particle size in the range of about 10-20 nm.

In some embodiments, for the co-assembled nanoparticle to provide an intracellular delivery, the outer coating is required. In further embodiments, an outer coating is required, which does not alter the encapsulating properties of the co-assembled nanoparticle.

Thus, in some embodiments, the co-assembled nanoparticles of the invention further comprise an outer coating. The outer coating can comprise at least one amphiphilic peptide comprising at least 2 pairs of alternating hydrophobic/hydrophilic amino acid residues, wherein the hydrophilic amino acid residue is positively charged. According to certain embodiments, the at least one amphiphilic peptide is capable of forming a β-sheet structure.

According to some embodiments, the at least one amphiphilic peptide of the outer coating comprises a sequence of amphiphilic β-sheet extended by hydrophobic amino acid residues. Thus, in certain embodiments, the at least one amphiphilic peptide further comprises a sequence of at least two hydrophobic amino acid residues. According to additional embodiments, the at least one amphiphilic peptide comprises a sequence of four hydrophobic amino acid residues. According to further embodiments, the at least one amphiphilic peptide comprises a sequence of six hydrophobic amino acid residues. According to some embodiments, the at least one amphiphilic peptide of the outer coating comprises an amino acid sequence according to Formula II:

$$Y1_{m1}\text{-(hydrophobic-hydrophilic)}_n\text{-}Y2_{m2} \quad \text{(Formula II)},$$

wherein m$_1$ and m$_2$ designate an integer, which can independently be selected from 1 to 10, n designates an integer of 2-20, hydrophobic designates a hydrophobic amino acid residue, hydrophilic designates a hydrophilic amino acid residue, Y1 designates a hydrophobic amino acid residue, Pro, Pro-hydrophilic amino acid residue or represents the coating peptide's amino terminus, and Y2 designates a hydrophobic amino acid residue, Pro, Pro-hydrophilic amino acid residue or represents the coating peptide's carboxy terminus.

In some embodiments, the outer coating comprises at least one amphiphilic peptide comprising at least 2 pairs of hydrophobic/hydrophilic amino acid residues, wherein the amino acid residues are randomly distributed along the peptide backbone and wherein the hydrophilic amino acid residue is positively charged. In certain such embodiments, the at least one amphiphilic peptide is a scrambled-order peptide corresponding to the peptide of Formula II, wherein the hydrophobic and hydrophilic amino acid residues are randomly distributed along the peptide backbone.

The at least one amphiphilic peptide comprised in the outer coating can be the same peptide comprised in the co-assembled nanoparticle or a different peptide. Each possibility represents a separate embodiment of the invention. In a certain embodiment, the outer coating comprises at least one amphiphilic peptide, which is identical to the at least one amphiphilic peptide forming the co-assembled nanoparticle.

In certain embodiments, the outer coating comprises at least one amphiphilic peptide selected from the group consisting of Pro-Lys-(Phe-Lys)$_n$-Pro (SEQ ID Nos: 2, 4, 6, 10, and 12), a scrambled order Pro-Lys-(Phe-Lys)$_n$-Pro and combinations thereof, wherein m$_1$ is an integer of 1, m$_2$ is an integer of 1 and n is an integer of 3-7. Each possibility represents a separate embodiment of the invention. In further embodiments, the outer coating comprises a peptide selected from the group consisting of (Leu)$_{m1}$-(Phe-Lys)$_n$-Pro (SEQ ID NOs:18, 24, 25, 26, and 27), Pro-Lys-(Phe-Lys)$_n$-(Leu)$_{m2}$ (SEQ ID NOs:19-23) and combinations thereof, wherein m$_1$ is an integer of 2-6, m$_2$ is an integer of 2-6 and n is an integer of 3-7. Each possibility represents a separate embodiment of the invention.

In further embodiments, the outer coating comprises at least one amphiphilic peptide, comprising an amino acid sequence selected from the group consisting of SEQ ID NO:2, SEQ ID NO:4, SEQ ID NO:6, SEQ ID NO:8, SEQ ID NO:10, and SEQ ID NO:12 to SEQ ID NO:17. Each possibility represents a separate embodiment of the invention. In some exemplary embodiments, the outer coating comprises a PK(FK)$_5$P peptide (SEQ ID NO:2) or a KFF-PKKPFKFFKK peptide (SEQ ID NO:16). In further exemplary embodiments, the outer coating comprises a L$_4$(FK)$_3$P (SEQ ID NO:13) or a L$_6$(FK)$_3$P peptide (SEQ ID NO:15).

In some embodiments, the co-assembled nanoparticles comprise PK(FK)$_5$P peptide (SEQ ID NO: 2), a poly-(gamma-glutamic acid) and further comprise an outer coating comprising PK(FK)$_5$P peptide (SEQ ID NO: 2). In other embodiments, the co-assembled nanoparticles comprise PK(FK)$_5$P peptide (SEQ ID NO: 2), a poly-(gamma-glutamic acid) and further comprise an outer coating comprising KFFPKKPFKFFKK peptide (SEQ ID NO: 16). In further embodiments, the co-assembled nanoparticles comprise PK(FK)$_5$P peptide (SEQ ID NO: 2), a poly-(gamma-glutamic acid) and further comprise an outer coating comprising L$_4$(FK)$_3$P peptide (SEQ ID NO: 13). In additional embodiments, the co-assembled nanoparticles comprise PK(FK)$_5$P peptide (SEQ ID NO: 2), a poly-(gamma-glutamic acid) and further comprise an outer coating comprising L$_6$(FK)$_3$P peptide (SEQ ID NO: 15).

According to some embodiments, the co-assembled nanoparticles have a negative surface potential. According to some embodiments, the co-assembled nanoparticles have a positive surface potential. According to further embodiments, the zeta potential of the co-assembled nanoparticles is above about 0 mV. In yet further embodiments, the zeta potential of the co-assembled nanoparticles having an outer coating is above about 0 mV.

In some embodiments, the mean particle size of the co-assembled nanoparticles comprising an outer coating is in the range of about 10-100 nm. In further embodiments, the mean particle size of the co-assembled nanoparticles comprising an outer coating is in the range of about 15-50 nm.

The co-assembled nanoparticles of the present invention can be used for encapsulating a pharmaceutically active ingredient. Thus, according to further embodiments, the co-assembled nanoparticle according to the principles of the present invention comprises a pharmaceutically active ingredient. The pharmaceutically active ingredient can be dissolved, entrapped, encapsulated or attached to the co-assembled nanoparticle. Each possibility represents a separate embodiment of the invention.

The co-assembled nanoparticles can be further used for the delivery of the pharmaceutically active ingredient to a target cell, to a target organ or a target organelle within the target cell. Thus, according to some embodiments, the co-assembled nanoparticle provides encapsulation and/or intracellular delivery of the pharmaceutically active ingredient. In further embodiments, the co-assembled nanoparticles of the present invention are for use in the delivery of the pharmaceutically active ingredient to a target cell, a target organelle or a combination thereof. In certain embodiments, the target organelle is mitochondria.

The present invention further provides an aqueous dispersion comprising a plurality of the co-assembled nanoparticles and an aqueous media in which the nanoparticles are dispersed. In some embodiments, the aqueous media comprises a physiologically acceptable buffer. The buffer can be selected from the group consisting of tris-buffered saline (TBS), phosphate-buffered saline (PBS) and any combination thereof.

In some embodiments, the aqueous dispersion is characterized by a uniform size distribution of the co-assembled nanoparticles. In further embodiments, the mean particle size of the co-assembled nanoparticles is in the range of about 10-100 nm. In some embodiments, the mean particle size of the co-assembled nanoparticles in the aqueous dispersion is in the range of about 10-50 nm. In other embodiments said mean particle size in the range of about 50-100 nm.

In another aspect, the present invention provides a pharmaceutical composition for intracellular delivery, the composition comprising a plurality of the co-assembled nanoparticles according to the principles of the present invention and a pharmaceutically active ingredient or a salt thereof. The pharmaceutically active ingredient can be dissolved, entrapped, encapsulated or attached to the co-assembled nanoparticles. Each possibility represents a separate embodiment of the invention. According to certain embodiments, the pharmaceutical composition comprises co-assembled nanoparticles having an outer coating.

In some embodiments the pharmaceutically active ingredient is amphiphilic. In some embodiments, the pharmaceutically active ingredient is positively charged. In other embodiments the pharmaceutically active ingredient is negatively charged.

In further embodiments, the pharmaceutically active ingredient is selected from the group consisting of anti-cancer agents, mitochondria-acting agents, active proteins and combinations thereof. Each possibility represents a separate embodiment of the invention. The anti-cancer agent may comprise, inter alia, Doxorubicin (DOX), Dequalinium (DQA), salts or combinations thereof. The mitochondria-acting agent may comprise, inter alia, Lonidamine (LND), salts or combinations thereof. In further embodiments, the pharmaceutically active ingredient is selected from the group consisting of Doxorubicin, Dequalinium, Lonidamine, and combinations thereof.

In certain embodiments, the pharmaceutical composition comprises a $PK(FK)_5P$ peptide (SEQ ID NO: 2), poly(gamma-glutamic-acid) and Dequalinium chloride. In other embodiments, the pharmaceutical composition comprises a $PK(FK)_5P$ peptide (SEQ ID NO: 2), poly(gamma-glutamic-acid) and Doxorubicin. In additional embodiments, the pharmaceutical composition comprises a $PK(FK)_5P$ peptide (SEQ ID NO: 2), poly(gamma-glutamic-acid) and Lonidamine.

In certain embodiments, the pharmaceutical composition comprises a plurality of co-assembled nanoparticles comprising a $PK(FK)_5P$ peptide (SEQ ID NO: 2), poly(gamma-glutamic-acid) and Dequalinium chloride. In other embodiments, the pharmaceutical composition comprises a plurality of co-assembled nanoparticles comprising a $PK(FK)_5P$ peptide (SEQ ID NO: 2), poly(gamma-glutamic-acid) and Doxorubicin. In additional embodiments, the pharmaceutical composition comprises a plurality of co-assembled nanoparticles comprising a $PK(FK)_5P$ peptide (SEQ ID NO: 2), poly(gamma-glutamic-acid) and Lonidamine.

In certain embodiments, the pharmaceutical composition comprises a plurality of co-assembled nanoparticles comprising a $PK(FK)_5P$ peptide (SEQ ID NO: 2) and poly(gamma-glutamic-acid), coated with an outer coating comprising a $PK(FK)_5P$ peptide (SEQ ID NO: 2), and Dequalinium chloride. In other embodiments, the pharmaceutical composition comprises a plurality of co-assembled nanoparticles comprising a $PK(FK)_5P$ peptide (SEQ ID NO: 2) and poly(gamma-glutamic-acid), coated with an outer coating comprising a $PK(FK)_5P$ peptide (SEQ ID NO: 2), and doxorubicin. In additional embodiments, the pharmaceutical composition comprises a plurality of co-assembled nanoparticles comprising a $PK(FK)_5P$ peptide (SEQ ID NO: 2) and poly(gamma-glutamic-acid), coated with an outer coating comprising a $PK(FK)_5P$ peptide (SEQ ID NO: 2), and Lonidamine.

The composition of the present invention may further comprise one or more pharmaceutically acceptable excipients some of which are useful for the improvement of the therapeutic effect of the drug and others influencing drug consistence and the final dosage form. The pharmaceutical composition can be formulated in many different forms, depending on the indication and discretion of the medical practitioner. In some embodiments the composition is in a form of dry composition, for example particles, granules or powder. In some embodiments, the dry form is obtained by lyophilization. In other embodiments the pharmaceutical composition is formulated in a liquid form, optionally comprising a physiologically acceptable buffer. The buffer can include, inter alia, tris-buffered saline (TBS), phosphate-buffered saline (PBS) or any combination thereof.

According to some embodiments, the pharmaceutical composition comprising a plurality of the co-assembled nanoparticles and a pharmaceutically active ingredient is for use in the delivery of the pharmaceutically active ingredient to a target cell. In some embodiments, the target cell is a cancer cell. In further embodiments, the pharmaceutical composition is for use in the delivery of the pharmaceutically active ingredient to the target organelle within the target cell. In some embodiments, the target organelle is mitochondria.

The pharmaceutical compositing of the present invention may be beneficially used in the treatment of proliferative diseases. The proliferative disease can be selected from the group consisting of sarcomas, carcinomas, lymphomas and melanomas.

The pharmaceutical compositing of the present invention may further be beneficially used in the treatment of mitochondrial dysfunction. The mitochondrial dysfunction can be associated with a disease, disorder or condition, such as, but not limited to, cancer.

In some embodiments, the present invention provides a method of treating a proliferative disease, said method comprising administering to a subject in need thereof a therapeutically effective amount of the pharmaceutical composition according to the principles of the present invention. In further embodiments, the present invention provides a method of treating a mitochondrial dysfunction, said method comprising administering to a subject in need thereof a therapeutically effective amount of the pharmaceutical composition according to the principles of the present invention.

In another aspect, the present invention provides a method of preparing a co-assembled nanoparticle, the method comprising the following steps: i. providing a liquid solution comprising at least one amphiphilic peptide of 4-40 amino acids comprising at least 2 pairs of alternating hydrophobic/hydrophilic amino acid residues, or a derivative or a salt thereof, capable of forming a β-sheet structure, in a vessel; ii. providing an alkaline solution comprising a polypeptide comprising polyanion; iii. mixing together the peptide solution and the polypeptide solution; iv. acidifying the solution obtained in step iii; and v. stirring for at least 8 hours.

According to some embodiments, the method further comprises a step of mixing a solution comprising a pharmaceutically active ingredient with the peptide solution and/or a polypeptide solution. According to further embodiments, the solution comprising a pharmaceutically active ingredient is mixed with the polypeptide solution prior to mixing with the peptide solution. In additional embodiments, a portion of the solution comprising a pharmaceutically active ingredient is mixed with the polypeptide solution and a portion of the solution comprising a pharmaceutically active ingredient is mixed with the polypeptide solution prior to step iii.

In some embodiments, the method of preparing a co-assembled nanoparticle, further comprises a step of adding a solution comprising an additional amphiphilic peptide of 4-40 amino acids comprising at least 2 pairs of alternating hydrophobic/hydrophilic amino acid residues, or a derivative or a salt thereof. According to some embodiments, said additional peptide is capable of forming a β-sheet structure. Said additional peptide may further comprise a sequence of hydrophobic amino acid residues.

In some embodiments, the method comprises repeating the step of adding the solution comprising the additional peptide. In some embodiments, the method comprises repeating the step of adding the solution comprising the additional peptide at least twice. In other embodiments, the method comprises repeating the step of adding the solution comprising the additional peptide until obtaining a nanoparticle having a positive zeta potential.

In yet another aspect, the present invention provides a kit comprising the co-assembled nanoparticles according to the principles of the present invention and optionally further comprising a physiologically acceptable buffer or excipient and an optional means for delivery of the nanoparticles. According to some embodiments, the co-assembled nanoparticles comprise a pharmaceutically active ingredient. In some embodiments the dry and liquid components may be present in separate containers in the kit, or some of the components may be combined within one container. Each possibility represents a separate embodiment of the invention.

Other objects, features and advantages of the present invention will become clear from the following description.

BRIEF DESCRIPTION OF THE DRAWINGS

FIGS. 1a-1d show experimental peptides used to prepare the co-assembled nanoparticles of the present invention: FIG. 1a—proline capped version—(PK(FK)$_5$P), abbreviated "PFK", corresponding to SEQ ID NO:2; FIG. 1b—free termini version FK(FK)$_5$F, abbreviated "FK", corresponding to SEQ ID NO:1; FIG. 1c—scrambled order peptide KFF-PKKPFKFFKK, abbreviated "rPFK", corresponding to SEQ ID NO:16; and FIG. 1d—scrambled order peptide KFFFK-KFFKFFKK, abbreviated "rFK", corresponding to SEQ ID NO:17.

FIG. 10b shows the fraction of β-sheet relative to random structure ($\theta_{215}/\theta_{202}$) as a function of different loading techniques, as detailed in the description of FIG. 10a.

FIGS. 15a-15f show intracellular observation of PFK (SEQ ID NO:2) coated PFK γ-PGA nanoparticles (FIGS. 15a-15c) and of uncoated PFK γ-PGA nanoparticles (FIGS. 15d-15f) using confocal laser scanning microscopy. FIGS. 15a and 15d show mitochondria stained with MitoTracker Deep Red 633 (red color, seen as grey stain in the figures), FIGS. 15b and 15e show uncoated and coated nanoparticles labeled with FITC (green color, seen as white dots in the figures), which were incubated with Saos2 cells, and FIGS. 15c and 15f show nanoparticles which co-localize with mitochondria, observed as yellow signals (seen as bright dots in the figures, some dots are indicated by arrows) in the merged images (bar=10 μm).

DETAILED DESCRIPTION OF THE INVENTION

Figure 2A:
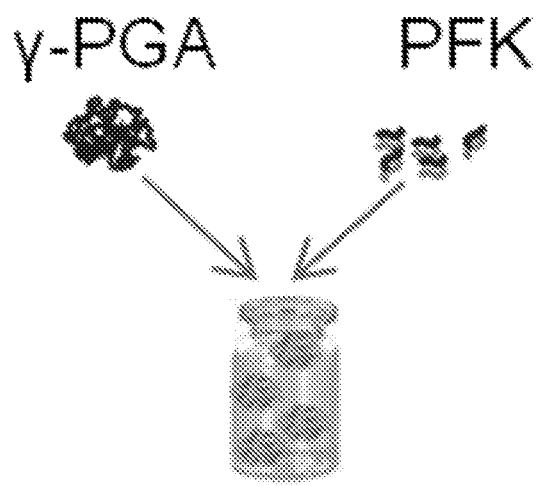
FIG. 2a shows a schematic representation of co-assembled nanoparticles formed from a combination of poly gamma glutamic acid and proline capped peptide (PK(FK)$_5$P) (SEQ ID NO:2) in an aqueous solution.

The present invention is directed to co-assembled peptide-polypeptide nanoparticles adapted for therapeutics delivery. The peptide-based co-assembled nanoparticles are particularly useful in the targeted intracellular delivery of amphiphilic and/or charged drugs. For example, targeted delivery of chemotherapeutic agents to the mitochondria can be carried out using the nanoparticles of the present invention.

Co-Assembled Nanoparticles Composition, Structure and Properties

The co-assembled nanoparticles are based on designed and synthetic self-assembled peptides combined with other polypeptides from natural source. Specific amino acid sequences are designed to induce well-defined secondary structures that may interact spontaneously via various non-covalent bonds to form hierarchically ordered assemblies. The peptides that can be used for the formation of the co-assembled nanoparticles of the present invention are amphiphilic peptides capable of forming a β-sheet structure. Amphiphilic peptides can be designed to adopt a β-sheet secondary structure using, inter alia, periodic alternation of hydrophobic and hydrophilic amino acids. The β-sheet structured peptide is configured to co-assemble with the polypeptide via electrostatic interaction between the peptide and the polypeptide in order to obtain co-assembled nanoparticles. Thus, the peptide and the polypeptide should have opposite electric charges. As such, the amphiphilic peptide may comprise positively charged hydrophilic amino acid residues and the polypeptide may comprise a polyanion. In some embodiments, the polypeptide comprises negatively charged carboxylic groups and the peptide comprises positively charged amino groups, leading to the electrostatic interaction between the positively and the negatively charged amino acid residues.

Thus, in a first aspect, the invention provides a co-assembled nanoparticle comprising at least one polypeptide comprising a polyanion; and at least one amphiphilic peptide capable of forming a β-sheet structure, a derivative or a salt thereof, the amphiphilic peptide comprising at least 2 pairs of alternating hydrophobic/hydrophilic amino acid residues, wherein the hydrophilic amino acid residue is positively charged.

The term "peptide" as used herein is meant to encompass natural, non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, either the L or D isomers may be used.

Conservative substitution of amino acids as known to those skilled in the art is within the scope of the present invention. Conservative amino acid substitution includes replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Also included within the scope of the invention are salts of the peptides, fragments, analogs, and derivatives of the peptides suitable for the co-assembled nanoparticles of the invention. The derivative can be a chemical or a functional derivative.

As used herein the term "salts" refers in some embodiments to both salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprise at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

The salts, analogs and the chemical derivatives of the peptides are preferably used to modify the pharmaceutical properties of the peptides insofar as stability, solubility, etc. are concerned.

The term "amphiphilic" refers to a molecule, including, inter alia, a synthetic peptide or a pharmaceutically active ingredient, possessing both hydrophilic and hydrophobic nature. A compound with such properties is called "amphiphilic".

DeGrado and Lear (W. F. DeGrado, J. D. Lear. J. Am. Chem. Soc., 1985, 107 (25), pp 7684-7689) showed that amphiphilic peptides comprising repetitive dyads of hydrophilic and hydrophobic amino acid residues tend to self assemble into β-pleated sheet structure at air-water interfaces. The assembly of β-sheet peptides into one-dimensional (1D) ribbons is mediated by inter-strand hydrogen bonds along the direction that is normal to the peptide strand. The flexibility of the peptide backbone and the repetitive nature of the hydrophilic-hydrophobic amino acid motif may induce dislocation defects that inhibit the 2D ordered structure. One of the inventors of the present invention obtained 2D order β-strand assemblies at air-water interfaces by using peptides terminated with proline (Pro) residues [Rapaport, H., Kjaer, K., Jensen, T. R., Leiserowitz, L. and D. A. Tirrell. Two-Dimensional Order in beta-sheet Peptide Monolayers. J. Am. Chem. Soc. 122: 12523-12529 (2000)]. Pro was chosen to be the terminal amino acid since it is a potent disrupter of β-sheet structure, such that Pro termini can minimize free motion and dynamic disorder at the ribbon edges due to geometric constrains imposed by the cyclic side chains.

According to some embodiments, the amphiphilic peptide capable of forming a β-sheet structure is 4-40 amino acids in length, 7-30 amino acids, 10-30 amino acids, or 10-20 amino acids in length. Each possibility represents a separate embodiment of the invention. The amphiphilic peptide may comprise one or two terminal Pro residues.

In further embodiments, the amphiphilic peptide capable of forming a β-sheet structure is at least 4 amino acids in length, at least 6 amino acids, at least 8 amino acids, at least 10 amino acids, at least 12 amino acids or at least 13 amino acids in length. Each possibility represents a separate embodiment of the invention. The amphiphilic peptide may comprise one or two terminal Pro residues.

According to some embodiments, the at least 2 pairs of alternating hydrophobic/hydrophilic amino acid residues are identical. According to some embodiments, all pairs of alternating hydrophobic/hydrophilic amino acid residues are identical.

The hydrophobic amino acid residue can be selected from the group consisting of Phe, Leu, Ile, Val, Trp and Ala. In some embodiments, the hydrophobic amino acid residue is Phe, Leu or Val. In a certain embodiment, the hydrophobic amino acid residue is Phe.

The hydrophilic amino acid residue can be selected from the group consisting of Lys and Arg. In a certain embodiment, the hydrophilic amino acid residue is Lys.

According to some embodiments, the at least one amphiphilic peptide comprises an amino acid sequence according to Formula I (presented hereinabove). The amphiphilic peptide may comprise alternating Phe and Lys residues in amino acid sequences of varying lengths. Said peptides may further include proline capped termini. According to further embodiments, the at least one amphiphilic peptide comprises an amino acid sequence Pro-Lys-(Phe-Lys)$_n$-Pro, wherein n is an integer of 2-7 (SEQ ID Nos: 2, 4, 6, 8, 10, and 12). According to yet further embodiments, the at least one amphiphilic peptide comprises an amino acid sequence Pro-Lys-(Phe-Lys)$_n$-Pro, wherein n is an integer of 3-7 (SEQ ID Nos: 2, 4, 6, 10, and 12). According to still further embodiments, the at least one amphiphilic peptide comprises an amino acid sequence Pro-Lys-(Phe-Lys)$_n$-Pro, wherein n is an integer of 4-6 (SEQ ID Nos: 2, 4, and 10). According to yet further embodiments, the at least one amphiphilic peptide comprises an amino acid sequence Pro-Lys-(Phe-Lys)$_n$-Pro, wherein n is an integer of 5 (SEQ ID NO:2).

For example, the amphiphilic peptide may have an amino acid sequence selected from SEQ ID NO:1 to SEQ ID NO:12 or a peptide matrix thereof. The term "matrix", as used herein, refers to a self-assembled molecular system generating nano-scale shapes, possibly involving chemical cross linking. In certain embodiments, the amphiphilic peptide has an amino acid sequence selected from the group consisting of SEQ ID NO:2, SEQ ID NO:4, SEQ ID NO:6, SEQ ID NO:8, SEQ ID NO:10, and SEQ ID NO:12.

Some of the exemplified peptides include peptidic sequences comprising Lys and Phe residues, as presented in FIGS. 1a-1d, including a proline capped version—(PK(FK)$_5$P), abbreviated "PFK" (FIG. 1a) and corresponding to SEQ ID NO:2; free termini version FK(FK)$_5$F, abbreviated "FK" (FIG. 1b) and corresponding to SEQ ID NO:1; and their corresponding scrambled order peptides KFFPKKPFKFFKK, abbreviated "rPFK" (FIG. 1c), corresponding to SEQ ID NO:16, and KFFFKKFFKFFKK, abbreviated "rFK" (FIG. 1d), corresponding to SEQ ID NO:17, wherein only PFK and FK are capable of forming a β-sheet secondary structure.

In certain embodiments, the amphiphilic peptide has an amino acid sequence selected from SEQ ID NO:1 or SEQ ID NO:2. In certain embodiments, the amphiphilic peptide is a SEQ ID NO:2 peptide.

The term "polypeptide", as used in some embodiments, refers to a polypeptide having at least about 1000 amino acid residues. In some embodiments, the term "polypeptide" refers to a polypeptide having at least about 1200 amino acid residues. In further embodiments, the term "polypeptide" refers to a polypeptide having at least about 1500 amino acid residues. In yet further embodiments, the term "polypeptide" refers to a polypeptide having at least about 1800 amino acid residues. In additional embodiments, the term "polypeptide" refers to a polypeptide having from about 1800 to about 10000 amino acid residues. In further embodiments, the term "polypeptide" refers to a polypeptide having from about 1800 to about 4500 amino acid residues.

The polypeptide, suitable for formation of the co-assembled nanoparticles of the present invention comprises a polyanion. The term "polyanion", as defined herein, is meant to include any molecules containing at least two or more negatively charged functional groups.

In some embodiments of the invention, the polypeptide comprises at least 70% negatively charged residues. In further embodiments, the polypeptide comprises at least 80% negatively charged residues. In additional embodiments of the invention, the polypeptide comprises at least 90% negatively charged residues. In certain embodiments, the polypeptide comprises 100% negatively charged residues.

The molecular weight of the polypeptide is typically above 200 KDa, such as, for example about 200-1000 KDa, 200-800 KDa, or 200-500 KDa. Each possibility represents a separate embodiment of the invention.

The polypeptide of the co-assembled nanoparticle can comprise glutamic acid residues. In a certain embodiment, the polypeptide is a g-Polyglutamic acid (poly(gamma-glutamic acid), γ-PGA). γ-PGA is an anionic polypeptide, soluble in water, nontoxic, biodegradable and hydrophilic. γ-PGA is produced by *Bacillus subtilis*.

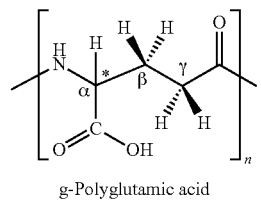

g-Polyglutamic acid

In other embodiments, polypeptide of the co-assembled nanoparticle comprises aspartic acid residues. In some embodiments the polypeptide is polyaspartic acid (PASA). The repeating unit of polyaspartic acid may exist in four different isomeric forms depending on the stereochemistry of starting material (D- and L-aspartic acid) and synthetic procedure leading to a and β links.

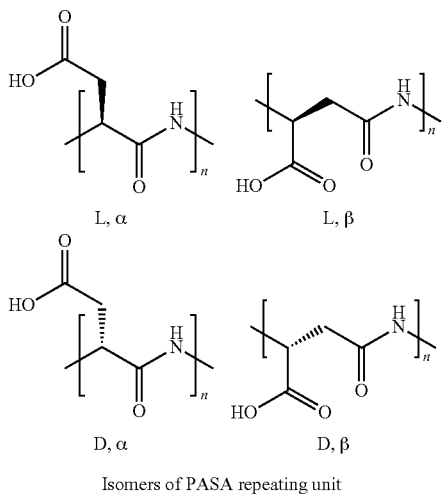

Isomers of PASA repeating unit

In some embodiments, the co-assembled nanoparticle comprises a poly-(gamma-glutamic acid) and at least one amphiphilic peptide capable of forming a β-sheet structure, a derivative or a salt thereof, the amphiphilic peptide comprising at least 2 pairs of alternating hydrophobic/hydrophilic amino acid residues, wherein the hydrophilic amino acid residue is positively charged. In some embodiments, the at least one amphiphilic peptide comprises at least one terminal Pro residue. In additional embodiments, the at least one amphiphilic peptide comprises two terminal Pro residues. In certain embodiments, the co-assembled nanoparticle comprises a poly-(gamma-glutamic acid) and a PK(FK)$_5$P peptide (SEQ ID NO:2).

FIG. 2a depicts a schematic representation of co-assembled nanoparticles formed from a combination of poly (gamma-glutamic acid) and proline capped peptide (PK(FK)$_5$P) (SEQ ID NO:2) in an aqueous solution. The proline capped peptide was found to form a β-sheet secondary structure when assembled with γ-PGA to form nanoparticles. Therefore, according to some embodiments, the co-assembled nanoparticles of the present invention comprise an amphiphilic peptide having a β-sheet secondary structure. In contrast, scrambled order peptides, which do not have alternating pairs of hydrophobic/hydrophilic amino acid residues, did not form a β-sheet secondary structure during co-assembly with γ-PGA. Additionally, when measured in the solution without the polypeptide, PFK peptide (SEQ ID NO:2) did not form a β-sheet structure. The nanoparticles comprising γ-PGA and amphiphilic peptide comprising at least two pairs of alternating hydrophobic/hydrophilic amino acid residues, wherein the hydrophilic residue is positively charged, were found to have a particle size suitable for intracellular delivery. Without wishing to being bound by theory, the most suitable nanoparticles for intracellular delivery have a diameter of 50 nm and spherical shape. [Verma A, Stellacci F., Small. 2010; 6(1):12-21]. Specifically, the proline capped peptide was found to have a mean particle size above 10 nm. The scrambled version of the proline capped peptide was characterized by a smaller mean particle size and a higher particle size distribution. Additionally, the γ-PGA polypeptide, which was not co-assembled with an amphiphilic peptide produced nanoparticles with a mean particle size smaller than 5 nm, which is not suitable for therapeutic agent loading and delivery. Thus, in some embodiments, the co-assembled nanoparticles have a mean particle size above 5 nm. According to some embodiments, the mean particle size of the co-assembled nanoparticle is above 10 nm. In further embodiments, the co-assembled nanoparticle has a mean particle size in the range of about 10-50 nm, preferably 10-20 nm. In certain embodiments, the co-assembled nanoparticle has a mean particle size of about 10-15 nm.

The term "particle size", as used herein, refers to the length of the particle in the longest dimension of the nanoparticle.

The co-assembled nanoparticles were found to be spherical. In contrast, the PFK peptide (SEQ ID NO:2) alone, when not co-assembled with the polypeptide, does not form a spherical particle. Thus, in the currently preferred embodiments, the co-assembled nanoparticles have an isotropically spherical shape. In certain such embodiments, the term "particle size" refers to the diameter of the isotropically spherical nanoparticle.

The term "isotropically spherical" as used herein refers to a particle shape coefficient in the mutually perpendicular planes of no more than about 1.5, or no more than 1.25.

In further embodiments, the co-assembled nanoparticles have a uniform particle size distribution. The term "uniform particle size distribution" refers, in some embodiments, to the variance in the particle sizes of the co-assembled nanoparticles which is less than about 50% of the mean particle size. In another embodiment, the term refers to the variance of less than about 40%, 30%, 20%, or 10%. Each possibility represents a separate embodiment of the invention.

The polypeptide and the peptide weight ratio in the co-assembled nanoparticle can be varied depending of the desired physical properties of the nanoparticle, such as the particle shape, size or the extent of β-sheet conformation of the amphiphilic peptide. Therefore, in some embodiments, the weight ratio of the peptide and the polypeptide is from about 0.2:1 to about 2:1.

The co-assembled nanoparticles comprising the PFK peptide (SEQ ID NO:2) and γ-PGA polypeptide at the weight ratio of 1:1 were found to be isotropically spherical. Furthermore, said particles were characterized by the highest extent of the β-sheet conformation as compared to nanoparticles having other weight ratios of the peptide and the polypeptide, and a particle size, which is particularly suitable for the intracellular delivery. In contrast, substantially lower weight percentages of the peptide as compared to the polypeptide produced unisotropically shaped nanoparticles and substantially higher weight percentages of the peptide than that of the polypeptide led to the formation of nanoparticles having a mean particle size above 20 nm and a less uniform particle size distribution. Additionally, the substantially lower or higher weight percentage of the peptide than that of the polypeptide, decreases the extent of the β-sheet peptide structure formation. Therefore, according to some embodiments, the weight ratio between the peptide and the polypeptide is from about 0.5:1 to about 1.5:1, or from 0.75:1 to 1.75:1, such as, but not limited to, about 1:1. Each possibility represents a separate embodiment of the invention According to further embodiments, the molar ratio between the peptide and the polypeptide in the co-assembled nanoparticle is from about 40:1 to about 200:1, such as, for example, from about 50:1 to about 150:1 or from about 80:1 to about 100:1. Each possibility represents a separate embodiment of the invention. According to yet further embodiments, the ratio between the positive charge of the peptide and the negative charge of the polypeptide is from about 1:10 to about 1:1, such as, for example, from about 1:8 to about 1:2, or from about 1:6 to about 1:4.

The co-assembled nanoparticles of the invention may be present in a liquid form or a solid form. Each possibility represents a separate embodiment of the invention. In the liquid form, the nanoparticles can be dispersed in an aqueous media. In some embodiments, the aqueous media is alkaline. In other embodiments, the aqueous media is acidic. In some embodiments, the aqueous media is neutral. In further embodiments the pH of the aqueous media is 4-8, such as, for example 4-5, 5-6, 6-7 or 7-8. In some embodiments, the co-assembled nanoparticles are dispersed in a physiologically acceptable buffer, such as, but not limited to, a tris-buffered saline.

The solid form of the nanoparticles of the present invention is preferably obtained by lyophilization. The lyophilized nanoparticles can be present in a powder or granular form.

According to some embodiments, the co-assembled nanoparticles of the present invention are stable in various pH environments, corresponding to endosomal, physiological and mitochondrial pH. According to some embodiments, the amphiphilic peptide of the nanoparticle has a reduced tendency to β-sheet conformation with increase in pH. Without wishing to being bound by theory or mechanism of action, it is contemplated that the co-assembled nanoparticle is stable in the endosome (having pH values lower than neutral) and is less stable in the mildly basic pH values at the matrix environment of the mitochondria. Thus, according to some embodiments, the stability of the co-assembled nanoparticles decreases with the increase in the pH from mildly acidic to mildly basic conditions.

The nanoparticles of the present invention may optionally be coated with a shell of peptides or specific lipids capable of enhancing penetration to cell membranes. Thus, in some embodiments, the nanoparticles comprise an outer coating.

For example, the peptidic coating applied to the co-assembled nanoparticle can modify zeta potential of the nanoparticle surface. Modifying zeta potential is particularly important for controlling the nanoparticle penetration through the cellular barriers. Without wishing to being bound by theory or mechanism of action, nanoparticles characterized by a positive zeta potential can penetrate cell membrane more efficiently than nanoparticles with negative zeta potential. Without further wishing to being bound by theory or mechanism of action, the co-assembled nanoparticles according to the principles of the present invention are capable of delivering the pharmaceutically active ingredient to the specific cell or organelle irrespective of the zeta potential of the nanoparticles. Thus, according to some embodiments, the outer coating is positively charged. According to some embodiments, the outer coating is negatively charged.

The outer coating may comprise the same peptide as the peptide present in the co-assembled nanoparticle. In other embodiments, the peptide may be a different peptide.

The peptide, useful for the coating of the nanoparticle may comprise at least one amphiphilic peptide comprising at least 2 pairs of alternating hydrophobic/hydrophilic amino acid residues, wherein the hydrophilic amino acid residue is positively charged. According to some embodiments, the peptide is capable of forming a β-sheet structure. According to other embodiments, the hydrophilic and hydrophobic amino acid residues are randomly distributed along the peptide backbone.

The peptide of the outer coating may further comprise a sequence of hydrophobic amino acid residues. According to some embodiments, the peptide comprises a sequence of at least two hydrophobic amino acid residues. According to other embodiments, the at least one amphiphilic peptide comprises a sequence of at least four hydrophobic amino acid residues. According to additional embodiments, the at least one amphiphilic peptide comprises a sequence of at least six hydrophobic amino acid residues.

According to some embodiments, the coating peptide comprises an amino acid sequence according to Formula II (presented hereinabove). In additional embodiments, the coating peptide is a scrambled-order peptide corresponding to the peptide of Formula II, wherein the amino acid residues are randomly distributed along the peptide backbone.

In some embodiments, the coating peptide comprises an amino acid sequence according to Formula I (presented hereinabove). In other embodiments, the coating peptide is a scrambled-order peptide corresponding to the peptide of Formula I, wherein the amino acid residues are randomly distributed along the peptide backbone.

The hydrophobic amino acid residue can be selected from the group consisting of Trp, Phe, Leu, Ile, Val and Ala. In some embodiments, the hydrophobic amino acid residue is Phe or Leu. In a certain embodiment, the hydrophobic amino acid residue in the alternating hydrophobic/hydrophilic pair is Phe. In another embodiment, the hydrophobic amino acid residue in hydrophobic sequence is Leu.

The hydrophilic amino acid residue can be selected from the group consisting of Lys and Arg. In a certain embodiment, the hydrophilic amino acid residue is Lys.

The at least one amphiphilic peptide comprised in the coating can be the same peptide comprised in the co-assembled nanoparticle or a different peptide. In further embodiments, the outer coating comprises a peptide selected from the group consisting of Pro-Lys-(Phe-Lys)$_n$-Pro, a scrambled order Pro-Lys-(Phe-Lys)$_n$-Pro and a combination thereof, wherein $m_1$ is an integer of 1, $m_2$ is an integer of 1 and n is an integer of 3-7 (SEQ ID Nos: 2, 4, 6, 10, and 12). In further embodiments, the outer coating comprises a peptide selected from the group consisting of (Leu)$m_1$-(Phe-Lys)$_n$-Pro (SEQ ID NO:18), Pro-Lys-(Phe-Lys)$_n$-(Leu)$_{m2}$ (SEQ ID NO:19) and a combination thereof, wherein $m_1$ is an integer of 2-6, $m_2$ is an integer of 2-6 and n is an integer of 3-7.

In further embodiments, the outer coating comprises at least one amphiphilic peptide, comprising an amino acid sequence selected from the group consisting of SEQ ID NO:1 to SEQ ID NO:17. In further embodiments, the outer coating comprises at least one amphiphilic peptide, having an amino acid sequence selected from SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, or SEQ ID NO:17. In some embodiments, the outer coating comprises a combination of said amphiphilic peptides.

In some exemplary embodiments, the outer coating comprises a PK(FK)$_5$P peptide (SEQ ID NO:2), or a KFFPK-KPFKFFKK peptide (SEQ ID NO:16). In further exemplary embodiments, the outer coating comprises a L4(FK)$_3$P (SEQ ID NO:13) or a L6(FK)$_3$P peptide (SEQ ID NO:15). Each possibility represents a separate embodiment of the invention.

In some embodiments, the co-assembled nanoparticles comprise a peptide having an amino acid sequence selected from the group consisting of SEQ ID NO:2, SEQ ID NO:4, SEQ ID NO:6, SEQ ID NO:8, SEQ ID NO:10, and SEQ ID NO:12 and poly(gamma-glutamic-acid); and further comprise an outer coating comprising a peptide, having an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, SEQ ID NO:17, and combinations thereof. Each possibility represents a separate embodiment of the invention.

In some embodiments, the co-assembled nanoparticles comprise $PK(FK)_5P$ peptide (SEQ ID NO:2), poly-(gamma-glutamic acid) and further comprise an outer coating comprising $PK(FK)_5P$ peptide. In other embodiments, the co-assembled nanoparticles comprise a $PK(FK)_5P$ peptide, poly-(gamma-glutamic acid) and further comprise an outer coating comprising a KFFPKKPFKFFKK peptide (SEQ ID NO:16). In further embodiments, the co-assembled nanoparticles comprise a $PK(FK)_5P$ peptide, poly-(gamma-glutamic acid) and further comprise an outer coating comprising a $L_4(FK)_3P$ peptide (SEQ ID NO:13). In additional embodiments, the co-assembled nanoparticles comprise a $PK(FK)_5P$ peptide, poly-(gamma-glutamic acid) and further comprise an outer coating comprising a $L_6(FK)_3P$ peptide (SEQ ID NO:15).

According to some embodiments, the outer coating comprises one layer of the amphiphilic peptide. According to other embodiments, the outer coating comprises two or more layers of the amphiphilic peptide. In certain embodiments, the outer coating comprises three layers of the amphiphilic peptide. Said layers can be applied to the co-assembled nanoparticles in different coating steps. According to particular embodiments, a portion of the coating peptide infiltrates the nanoparticle during the coating step.

Figure 2B:
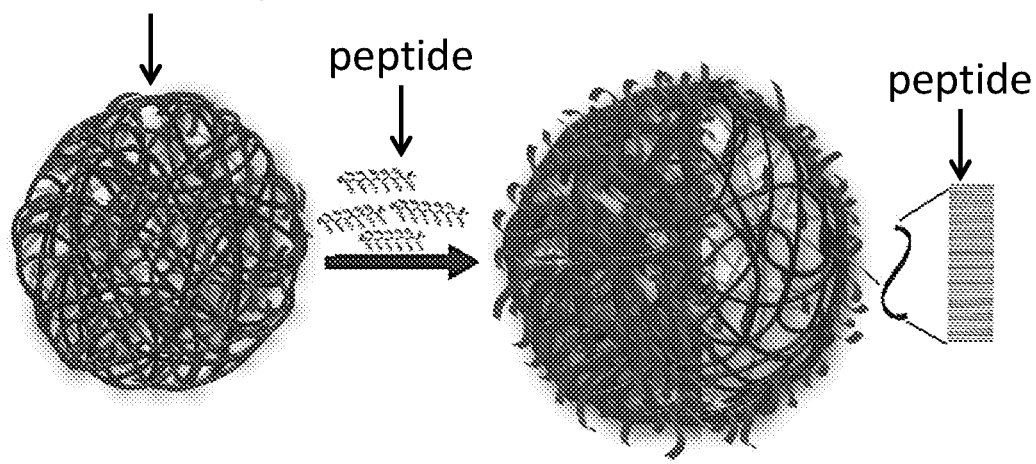
FIG. 2b shows a schematic representation of co-assembled nanoparticles formed from a combination of poly gamma glutamic acid and proline capped peptide (PK(FK)$_5$P) (SEQ ID NO:2), wherein the nanoparticle is coated with an outer coating comprising PK(FK)$_5$P peptide (SEQ ID NO:2).

FIG. 2b shows a schematic representation of a co-assembled nanoparticle having an outer coating comprising a $PK(FK)_5P$ peptide (SEQ ID NO:2). Without wishing to being bound to theory or mechanism of action it is believed that $PK(FK)_5P$ interacts electrostatically with the negatively charged polypeptide. Positively charged $PK(FK)_5P$ peptide at the surface of the nanoparticle can be assembled in a bilayer structure, wherein one side of such bilayer structure stabilizes the negative charge of the nanoparticle surface and the other side exposes positive charges to the surrounding solution. Thus, according to some embodiments, the peptide comprised in the outer coating has a bilayer structure.

The co-assembled nanoparticle comprising an outer coating can also be seen as a core-shell nanoparticle, wherein the co-assembled peptide-polypeptide constitute the core and the outer coating constitutes the shell.

The outer coating may include a cell penetrating peptide. In some embodiments, the outer coating comprises a lipid, a lipophilic cation, a cell penetrating peptide or any combination thereof. In some embodiments, the co-assembled nanoparticle further comprises mitochondrial localization peptidic sequences (MLS). Further information on cell penetrating peptides and MLS can be found in Meade, B. R. and Dowdy, S. F. (2007), Adv. Drug. Delivery Rev. 59, 134-140 and in H. H. Szeto, Antioxidants & Redox Signaling, Volume 10, Number 3, 2008, which are incorporated by reference herein in their entirety.

In some embodiments, the co-assembled nanoparticles have a negative zeta potential. In further embodiments, the co-assembled nanoparticles have a zeta potential in the range of −50 mV to about—1 mV. In other embodiments, the co-assembled nanoparticles have a positive zeta potential.

In some embodiments, the co-assembled nanoparticles having an outer coating have a zeta potential of above about 0 mV. In further embodiments, the nanoparticles having an outer coating have a zeta potential of at least about 1 mV. In other embodiments, the nanoparticles having an outer coating have a zeta potential of at least about 5 mV. In further embodiments, the nanoparticles having an outer coating have a zeta potential of at least about 10 mV.

In some embodiments, the mean particle size of the co-assembled nanoparticles having an outer coating is in the range of about 5-100 nm, such as, for example 10-100 nm, 20-100 nm, 30-100 nm, 40-100 nm, 50-100 nm, 60-100 nm, 10-80 nm, 10-70 nm, 10-60 nm, or 10-50 nm. Each possibility represents a separate embodiment of the invention.

Co-Assembled Nanoparticles Comprising a Pharmaceutically Active Ingredient

The co-assembled nanoparticles of the present invention may further comprise a pharmaceutically active ingredient or a salt or ester thereof. According to some embodiments, the co-assembled nanoparticle is capable of encapsulating a pharmaceutically active ingredient. Thus, in some embodiments, the co-assembled nanoparticles comprise a pharmaceutically active ingredient encapsulated, dissolved, dispersed or entrapped within the nanoparticle or attached to a nanoparticle. Each possibility represents a separate embodiment of the invention. According to further embodiments, the pharmaceutically active ingredient is not bonded to the nanoparticles. According to yet further embodiments, the pharmaceutically active ingredient is not chemically bonded to the nanoparticles. According to still further embodiments, the pharmaceutically active ingredient is not bonded to the amphiphilic peptide. According to yet further embodiments, the pharmaceutically active ingredient is not chemically bonded to the amphiphilic peptide. According to further embodiments, the co-assembled nanoparticle provides intracellular delivery of the pharmaceutically active ingredient.

Thus, in another aspect, there is provided a pharmaceutical composition comprising a plurality of the assembled nanoparticles of the invention and a pharmaceutically active ingredient or a salt or ester thereof. It is to be understood explicitly that the nanoparticles of the invention are capable of encapsulating any pharmaceutically active ingredient. However, the co-assembled nanoparticles of the present invention are specifically useful in the encapsulation of amphiphilic and/or charged pharmaceutically active ingredients. Said nanoparticles are further configured to provide targeted intracellular delivery of said amphiphilic and/or charged pharmaceutically active ingredients. Said pharmaceutically active ingredient can be positively charged or negatively charged. Each possibility represents a separate embodiment of the invention. Without wishing to being bound by theory or mechanism of action, the presence of the negatively charged groups of the anionic polypeptide and the positively charged groups of the peptides enables interaction of the co-assembled nanoparticle with the positively or negatively charged pharmaceutically active ingredient, thus providing encapsulation thereof by the co-assembled nanoparticle.

Figure 3:
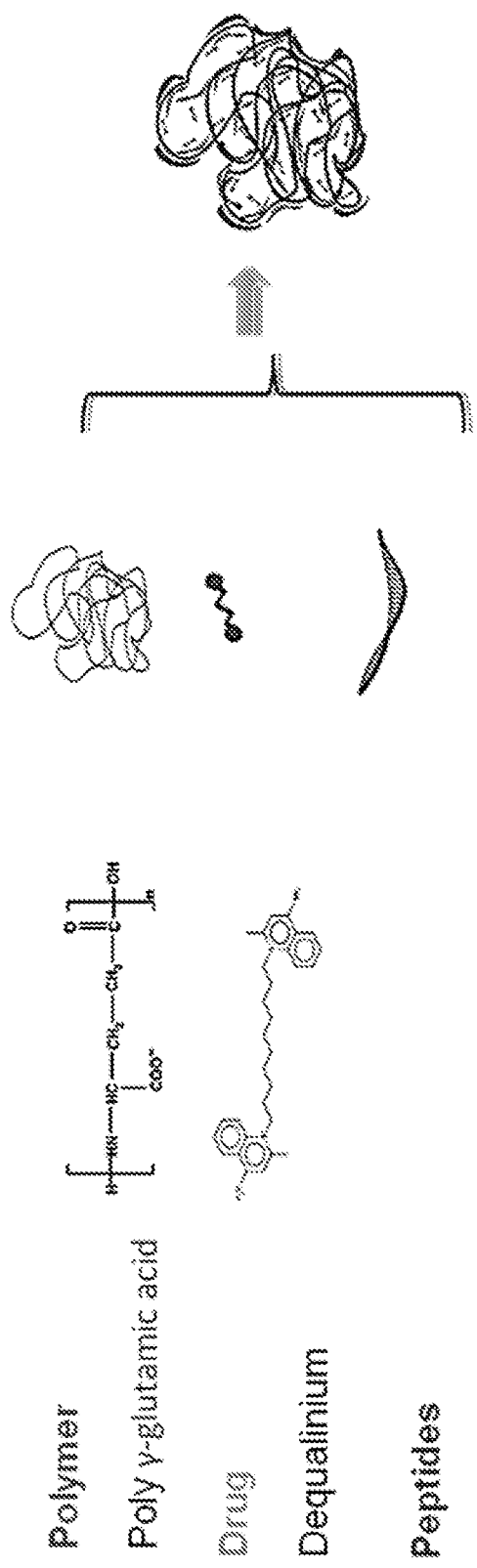
FIG. 3 shows a schematic representation of a co-assembled nanoparticle formed from a combination of poly gamma glutamic acid, proline capped peptide (PK(FK)$_5$P) (SEQ ID NO:2) and a pharmaceutically active ingredient (Dequalinium).

FIG. 3 depicts a schematic representation of a co-assembled nanoparticle formed from a combination of poly (gamma-glutamic acid), proline capped peptide ($PK(FK)_5P$) (SEQ ID NO:2) and a pharmaceutically active ingredient (Dequalinium).

In some embodiments, the pharmaceutically active ingredient comprises an anti-cancer reagent. As used herein, the phrase "anti-cancer reagent" refers to any type of reagent that may be used in the treatment of cancer and/or cancer related conditions. The anti-cancer reagent may include any naturally occurring or synthetically produced molecule that is capable of affecting directly or indirectly the growth and/or viability of cancer cells, cancer tumor, and/or cancer related conditions and symptoms. The pharmaceutical compositions of the present invention may comprise at least one anti-cancer reagent selected from the group consisting of a chemical molecule, a synthetic chemical molecule, a chemotherapeutic drug, a biologically therapeutic drug, and a naturally occurring, modified, recombinant or chemically synthesized protein or peptide. The anti-cancer reagent may be cytotoxic (toxic to cells) and/or cytostatic (suppress cell growth) and/or antiproliferative to the cancer cells and may exert its effect on cancer cells directly and/or indirectly. According to some embodiments, the anti-cancer reagent may be administered alone and/or in combination and/or before and/or after one or more additional cancer treatments. The additional cancer treatment may include such treatments as, but not limited to: chemotherapy (use of drugs to affect the cancer cells), radiotherapy (use of high-energy radiation of various sources to affect the cancer cells); biological therapy (a therapy which helps the immune system fight cancer); surgical procedures (surgical removal of the cancerous tumor); gene therapy; bone marrow transplantation; any other therapy known in the art, or any combination thereof. In particular embodiments, the anti-cancer reagent comprises a chemotherapeutic drug.

Non limiting examples of chemotherapeutic drugs may include such drugs as, but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

In other embodiments, the pharmaceutically active ingredient comprises a mitochondria-acting agent. Various diseases can occur due to mitochondrial defects. Mitochondrial disease can occur due to genomic defects in the nucleus or mitochondria. The wide varieties of diseases results from defective protein in the electron transport system of the mitochondria. The defective proteins can be any of the 13 that encode in the mitochondria or those that encode in the nucleus. During the electron transfer through the electron transfer complex, oxygen radicals are formed, this causes the oxidative stress. Oxidative stress occurs when the net amount of ROS exceeds the antioxidant amount. Hence oxidative stress is a result of increase in ROS, decrease in antioxidant or both. ROS forms in various oxidation pathways and can cause cellular dysregulation. ROS can react with cellular macromolecules and enhance the process of lipid peroxidation, cause DNA damage and/or induce protein and nucleic acid modifications. There are two types of antioxidants, enzymatic such as superoxide dismutases (SOD), catalase (CAT) and glutathione peroxidase (GPX) and non-enzymatic such as vitamin C, vitamin E, β-carotene. Oxidative stress associated with many physiological complications including metabolic syndrome related manifestations such as atherosclerosis, hypertension and type two diabetic. Oxidative stress maybe early event of theses chronic diseases. Anti-oxidants and different drugs used to reduce the free radicals and defense the cell from oxidation damage. Thus, the mitochondria-acting agent may comprise an antioxidant or a mitochondrial uncoupler that acts to separate oxidative phosphorylation from ATP synthesis.

In some embodiments, the pharmaceutically active ingredient comprises an active protein.

A pharmaceutically active ingredient combining anti-cancer and mitochondria-acting properties can beneficially be used in the pharmaceutical compositions of the present invention. Thus, in some embodiments, the pharmaceutical composition includes a mitochondrial acting anti-cancer agent. The mitochondrial acting anti-cancer agent may be, for example, (i) a modulator of the BCL-3 protein family, such as compounds that act on BCL-XL, BCL-2, BCL-W, MCL1, or the like; (ii) metabolic inhibitors such as compounds that affect, HK, affect HK2-VDAC interaction, PDK inhibitors, affect LDH-A, affect fatty acid synthase, affect ATP citrate lyase, acetyl-CoA carboxylase inhibitors, or the like; (iii) VDAC-targeting or ANT-targeting agents; (iv) ROS regulators such as SOD inhibitors, GSH inhibitors, GPX inhibitors, or the like; (v) HSP90 inhibitor; or (vi) the like. Examples of specific mitochondrial acting anti-cancer agents include Lonidamine (LND), Dequalinium chloride (DQA), a-tocopheryl succinate (a-TOS), dichloroacetate, A-385358, ABT-263, ABT-737, AT-101, 2-amino-6-bromo-4-(1-cyano-2-ethoxy-2-oxoethyl)-4H-chromene-3-carboxylate (HA14-1), oblimersen, obatoclax, gossypol, methyl jasmonate, dichloroacetate, HK2 peptide, LDH-A shRNA, orlistat, SB-204990, soraphen A, 4-(N-(s-glutathionylacetate)aminophenylarsenoxide (GSAO), clodronate, PK11 195, menadione, β-lapachone, CD437, gamitrinibs, 8-(2-chloro-3,4,5-trimethyoxybenzyl)-2-fluoro-9-(pent-4-nyl)-9H-purin-6-amine (PU24Fc1), (8-(6-bromobenzo[d][1,3]dioxol-5-ylthio)-9-(pent-4-ynyl)-9H-purin-6-amine (PU-H58), 8-(6-iodobenzo [d] [1,3] dioxol-5-ylthio)-9-(3-isopropylamio)propyl-9H-purin-6-amine (PU-H71), shepherdin, reservatrol, 2-methoxyestradiol, tetrathiomolybdate (ATN-224), buthioninesulphoximine, dimethylamino-parthenolide (DMAPT), parthenolide, imexons, mangafodipir, menadione, motexafin gadolinium, PEITCs, elescomol (STA-4783), all-trans-retinoic acid, 6-[3-(l-adamantyl)-4-hydroxyphenyl]-2-napthalene carboxylic acid (CD437), (E)-3-(4'-hydroxy-3'-adamantylbiphenyl-4yl) acrylic acid (ST1926), 3-bromopyruvate, butyric acid, resveratrol, 2-deoxy-D-glucose, arsenite trioxide, betulinic acid, and the like.

In certain embodiments, the pharmaceutical composition comprises a plurality of the co-assembled nanoparticles and a pharmaceutically active ingredient selected from the group consisting of Dequalinium chloride, Doxorubicin, Lonidamine and salts or esters thereof.

Dequalinium chloride (DQA) is a cationic, lipophilic mitochondrial poison, which selectively targets the mitochondrial membrane of certain epithelial carcinoma cells, in which it inhibits cellular energy production.

Lonidamine (LND) is a negatively charged and mildly amphiphilic molecule. Lonidamine is a powerful anti spermatogenic agent which affects the energy metabolism of normal and neoplastic cells in characteristically different ways. In both types of cells, this compound strongly inhibits oxygen consumption. However, Lonidamine evokes an increase in aerobic lactate accumulation, as would be expected in normal differentiated cells. In contrast, in both experimental and human tumors, both the aerobic and anaerobic lactate productions are strongly inhibited by Lonidamine. Preliminary results suggested that this effect might be related to an inhibition of mitochondrially bound hexokinase, which is present in considerable amounts in the outer mitochondrial compartment of neoplastic cells.

Doxorubicin (DOX) or more specifically a hydrochloride salt of doxorubicin, is an anthracycline antibiotic with antineoplastic activity. Doxorubicin, isolated from the bacterium *Streptomyces peucetius* var. *caesius*, is the hydroxylated congener of daunorubicin. Doxorubicin intercalates between base pairs in the DNA helix, thereby preventing DNA replication and ultimately inhibiting protein synthesis. Additionally, doxorubicin inhibits topoisomerase II which results in an increased and stabilized cleavable enzyme-DNA linked complex during DNA replication and subsequently prevents the ligation of the nucleotide strand after double-strand breakage.

In some embodiments, the pharmaceutical composition comprises a plurality of co-assembled nanoparticles comprising a peptide having an amino acid sequence selected from the group consisting of SEQ ID NO:2, SEQ ID NO:4, SEQ ID NO:6, SEQ ID NO:8, SEQ ID NO:10, and SEQ ID NO:12, and poly(gamma-glutamic-acid), having an outer coating comprising a peptide, having an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, SEQ ID NO:17, and combinations thereof; and Dequalinium chloride. Each possibility represents a separate embodiment of the invention.

In some embodiments, the pharmaceutical composition comprises a plurality of co-assembled nanoparticles comprising a peptide having an amino acid sequence selected from the group consisting of SEQ ID NO:2, SEQ ID NO:4, SEQ ID NO:6, SEQ ID NO:8, SEQ ID NO:10, and SEQ ID NO:12, and poly(gamma-glutamic-acid), having an outer coating comprising a peptide, having an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, SEQ ID NO:17 and combinations thereof; and doxorubicin. Each possibility represents a separate embodiment of the invention.

In some embodiments, the pharmaceutical composition comprises a plurality of co-assembled nanoparticles comprising a peptide having an amino acid sequence selected from the group consisting of SEQ ID NO:2, SEQ ID NO:4, SEQ ID NO:6, SEQ ID NO:8, SEQ ID NO:10, and SEQ ID NO:12, and poly(gamma-glutamic-acid), having an outer coating comprising a peptide, having an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, SEQ ID NO:17 and combinations thereof; and Lonidamine. Each possibility represents a separate embodiment of the invention.

In certain embodiments, the pharmaceutical composition comprises a plurality of co-assembled nanoparticles comprising a $PK(FK)_5P$ peptide (SEQ ID NO:2), poly(gamma-glutamic-acid) and Dequalinium chloride. In other embodiments, the pharmaceutical composition comprises a plurality of co-assembled nanoparticles comprising a $PK(FK)_5P$ peptide, poly(gamma-glutamic-acid) and doxorubicin. In additional embodiments, the pharmaceutical composition comprises a plurality of co-assembled nanoparticles comprising a $PK(FK)_5P$ peptide, poly(gamma-glutamic-acid) and Lonidamine.

According to particular embodiments, the pharmaceutical composition according to the principles of the present invention comprises a plurality of co-assembled nanoparticles comprising a $PK(FK)_5P$ peptide (SEQ ID NO:2) and poly(gamma-glutamic-acid), coated with an outer coating comprising a $PK(FK)_5P$ peptide, and Dequalinium chloride. In other embodiments, the pharmaceutical composition comprises a plurality of co-assembled nanoparticles comprising a $PK(FK)_5P$ peptide and poly(gamma-glutamic-acid), coated with an outer coating comprising a $PK(FK)_5P$ peptide, and doxorubicin. In additional embodiments, the pharmaceutical composition comprises a plurality of co-assembled nanoparticles comprising a $PK(FK)_5P$ peptide and poly(gamma-glutamic-acid), coated with an outer coating comprising a $PK(FK)_5P$ peptide, and Lonidamine.

According to particular embodiments, the pharmaceutical composition according to the principles of the present invention comprises a plurality of co-assembled nanoparticles comprising a $PK(FK)_5P$ peptide (SEQ ID NO:2) and poly(gamma-glutamic-acid), coated with an outer coating comprising a $L_4(FK)_3P$ peptide (SEQ ID NO:13), and Dequalinium chloride. In other embodiments, the pharmaceutical composition comprises a plurality of co-assembled nanoparticles comprising a $PK(FK)_5P$ peptide and poly(gamma-glutamic-acid), coated with an outer coating comprising a $L_4(FK)_3P$ peptide, and doxorubicin. In additional embodiments, the pharmaceutical composition comprises a plurality of co-assembled nanoparticles comprising a $PK(FK)_5P$ peptide and poly(gamma-glutamic-acid), coated with an outer coating comprising a $L_4(FK)_3P$ peptide, and Lonidamine.

According to particular embodiments, the pharmaceutical composition according to the principles of the present invention comprises a plurality of co-assembled nanoparticles comprising a $PK(FK)_5P$ peptide (SEQ ID NO:2) and poly(gamma-glutamic-acid), coated with an outer coating comprising a $L_6(FK)_3P$ (SEQ ID NO:15) peptide, and Dequalinium chloride. In other embodiments, the pharmaceutical composition comprises a plurality of co-assembled nanoparticles comprising a $PK(FK)_5P$ peptide and poly(gamma-glutamic-acid), coated with an outer coating comprising a $L_6(FK)_3P$ peptide, and doxorubicin. In additional embodiments, the pharmaceutical composition comprises a plurality of co-assembled nanoparticles comprising a $PK(FK)_5P$ peptide and poly(gamma-glutamic-acid), coated with an outer coating comprising a $L_6(FK)_3P$ peptide, and Lonidamine.

According to particular embodiments, the pharmaceutical composition according to the principles of the present invention comprises a plurality of co-assembled nanoparticles comprising a $PK(FK)_5P$ peptide (SEQ ID NO:2) and poly(gamma-glutamic-acid), coated with an outer coating comprising a KFFPKKPFKFFKK peptide (SEQ ID NO:16), and Dequalinium chloride. In other embodiments, the pharmaceutical composition comprises a plurality of co-assembled nanoparticles comprising a $PK(FK)_5P$ peptide and poly(gamma-glutamic-acid), coated with an outer coating comprising a KFFPKKPFKFFKK peptide, and doxorubicin. In additional embodiments, the pharmaceutical composition comprises a plurality of co-assembled nanoparticles comprising a $PK(FK)_5P$ peptide and poly(gamma-glutamic-acid), coated with an outer coating comprising a KFFPKKPFKFFKK peptide, and Lonidamine.

In some embodiments, the co-assembled nanoparticles comprising a pharmaceutically active ingredient have a negative zeta potential. In further embodiments, the nanoparticles comprising a pharmaceutically active ingredient have a zeta potential in the range of −50 mV to about—1 mV.

In other embodiments, the co-assembled nanoparticles comprising a pharmaceutically active ingredient have a positive zeta potential.

In some embodiments, the nanoparticles comprising a pharmaceutically active ingredient and having an outer coating have a zeta potential of above about 0 mV. In further embodiments, said nanoparticles have a zeta potential of at least about 1 mV. In other embodiments, said nanoparticles have a zeta potential of at least about 5 mV. In further embodiments, said nanoparticles have a zeta potential of at least about 10 mV.

In some embodiments, the mean particle size of the co-assembled nanoparticles comprising a pharmaceutically active ingredient is in the range of about 5-100 nm, such as, for example 5-80 nm, 5-70 nm, 5-60 nm, or 5-50 nm. Each possibility represents a separate embodiment of the invention.

In some embodiments, the mean particle size of the co-assembled nanoparticles comprising a pharmaceutically active ingredient and having an outer coating is in the range of about 5-100 nm, such as, for example 10-100 nm, 20-100 nm, 30-100 nm, 40-100 nm, 50-100 nm, 60-100 nm, 10-80 nm, 10-70 nm, 10-60 nm, or 10-50 nm. Each possibility represents a separate embodiment of the invention.

According to some embodiments, the pharmaceutically active ingredient is positively charged. In certain such embodiments, a positive to negative charge ratio between the pharmaceutically active ingredient and the polypeptide is from about 4:1 to about 1:2000. In certain embodiments, the pharmaceutically active ingredient is Dequalinium.

According to some embodiments, the pharmaceutically active ingredient is negatively charged. In certain such embodiments, a weight ratio between the peptide and the pharmaceutically active ingredient is from about 50:1 to 1:5. In further embodiments, the weight ratio is from about 5:1 to about 1:2. In particular embodiments, the weight ratio is from about 3:1 to about 1:1. In other embodiments, the weight ratio is from about 50:1 to about 25:1. In particular embodiments, the nanoparticles comprising said weight ratio of the peptide and the pharmaceutically active ingredient are kept at a pH of above about 7. In certain embodiments, the pharmaceutically active ingredient is Lonidamine.

According to some embodiments, the co-assembled nanoparticle provides controlled release of the pharmaceutically active ingredient. The release of the pharmaceutically active ingredient can be controlled, inter alia, by pH. According to some embodiments, the release of the pharmaceutically active ingredient increases with increase of the pH from mild acidic to mild basic conditions. In certain embodiments, co-assembled nanoparticle releases above about 70% of the pharmaceutically active ingredient at a pH value of above about 8 within 24 hours of the dissolution experiment. According to further embodiments, the released amount is above about 80%. In some embodiments, the pH value is about 8.5.

In other embodiments, the co-assembled nanoparticle releases below about 70% of the pharmaceutically active ingredient at a pH value of below about 6 within 24 hours of the dissolution experiment. According to further embodiments, the released amount is about 65%. In some embodiments, the pH value is about 5. In certain embodiments, the co-assembled nanoparticle releases about 50% of the pharmaceutically active ingredient at a pH value of about 5 and about 70% of the pharmaceutically active ingredient at a pH value in the range of about 7.4 to about 8.5 within about 3 hours of the dissolution experiment. In further embodiments, the co-assembled nanoparticle releases about 50% of the pharmaceutically active ingredient at a pH value of about 5 within about 3 hours of the dissolution experiment and at a pH value in the range of 7.4 to about 8.5 within about 1 hour. In some embodiments, the pharmaceutically active ingredient is Lonidamine.

According to some embodiments, the co-assembled nanoparticle provides controlled release of at least 10% of the pharmaceutically active ingredient. According to yet further embodiments, the co-assembled nanoparticle provides controlled release of at least 20% of the pharmaceutically active ingredient. According to still further embodiments, the co-assembled nanoparticle provides controlled release of the pharmaceutically active ingredient for at least 5 hours, such as, for example, 10 hours, 12 hours or 24 hours. In some embodiments, the pharmaceutically active ingredient is selected from Lonidamine or Dequalinium.

The co-assembled nanoparticles comprising a pharmaceutically active ingredient were found to form spherical particles with a mean particle size in the range of about 10 to about 20 nm. The co-assembled nanoparticles of the present invention were capable of accommodating large amounts of the therapeutically active ingredient.

In another embodiment, the pharmaceutical composition according to embodiments of the present invention may further comprise one or more pharmaceutically acceptable excipients. The excipients may influence the drug consistency and the final dosage form such as, for example, a solid or a liquid dosage form. In some embodiments, the excipient comprises a physiologically acceptable buffer, including, inter alia, tris-buffered saline.

The pharmaceutical compositions of the present invention may be used in the intracellular delivery of various pharmaceutically active agents. Said compositions are particularly useful in the intracellular delivery of amphiphilic active agents. In some embodiments, the co-assembled nanoparticles comprising the pharmaceutical active agent can be targeted to a specific organelle within the cell. In certain embodiments, said nanoparticles are mitochondria-targeted. In other embodiments, the co-assembled nanoparticles comprising the pharmaceutical active agent may be used to deliver the active agent to a specific type of cell, for example a cancer cell.

Thus, in some embodiments, the pharmaceutical compositions of the invention are for use in the treatment of proliferative diseases. In these embodiments, the proliferative disease may be selected from the group consisting of sarcomas, carcinomas, lymphomas and melanomas. Said carcinoma can include, but is not limited to, the carcinoma of breast prostate or colon. The term "treatment", as used in some embodiments, refers to slowing down or inhibiting the cell proliferation in a tumor. The present invention further provides a method of treatment of a proliferative disease, the method comprising administering to a subject in need thereof a therapeutically effective amount of the pharmaceutical composition comprising a plurality of co-assembled nanoparticles and a pharmaceutically active ingredient.

In other embodiments, the pharmaceutical compositions of the invention are for use in the treatment of mitochondrial dysfunction. The mitochondrial dysfunction may be associated with a disease or a disorder such as, but not limited to, metabolic syndrome, atherosclerosis, cancer, neurodegenerative diseases, neuromuscular disorders, cardiovascular disorders or type-two diabetes. Examples of neurodegenerative diseases that may be associated with mitochondrial dysfunction include, inter alia, Alzheimer's disease, ischemic injury, Parkinson diseases and stroke. Cancer that may be associated with mitochondrial dysfunction includes, inter alia, cancer of breast, prostate, colon, melanoma and lymphoma. The present invention, therefore, provides a method of treatment of a mitochondrial dysfunction, the method comprising administering to a subject in need thereof a therapeutically effective amount of the pharmaceutical composition comprising a plurality of co-assembled nanoparticles and a pharmaceutically active ingredient.

As can be understood herein the treatment as described according to the present invention may be achieved by using an effective amount of the pharmaceutical composition comprising the co-assembled nanoparticles and a pharmaceutically active ingredient.

The terms "effective amount", "therapeutically effective amount" or "dosing" are used herein interchangeably and mean any amount necessary to achieve a selected result, which may involve the amount of the pharmaceutical composition necessary for treating proliferative diseases, for example, killing the cancerous or otherwise abnormal cells or slowing their growth or treating mitochondrial dysfunction.

The therapeutic effective amount, or dosing, is dependent on severity and responsiveness of the disease state to be treated, with the course of treatment lasting one hour to several hours, or until a cure is effected or a diminution of the disease state is achieved. Dosing may be provided to a person in need in a regimen comprising dosing of one daily or multiple daily administrations. Persons of ordinary skill can readily determine optimum dosages, dosing methodologies and repetition rates, depending on the pharmaceutically active ingredient used and the condition to be treated.

The terms "disease", "disorder" and "condition" are used herein interchangeably.

As used herein to describe the present invention, "malignant", "cancer", "tumor", "malignancy", "proliferative", "hyperproliferative" all relate equivalently to a hyperplasia of a tissue or an organ.

According to some embodiments, the pharmaceutical compositions according to the principles of the present invention may be administered to a patient, for example, by systemic administration or topical administration.

The term "systemic administration" is to be referred as a route of administration comprising enteral administration comprising for example oral, rectal, sublingual or buccal administration or parenteral administration which may comprise for example piercing the skin or mucous membrane.

The term "topical administration" is to be referred as a route of administration comprising application to the surface of a body part.

In some embodiments, the route of administration may involve, for example, intravenous (i.v.), intramuscular (i.m.), intraperitoneal (i.p.), transdermal, transmucosal, intra-tumor, intragastric, intranasal or orally for example by tablets, capsules, lozenges or drops, or topical administration for example by creams, dermal patches and the like or any combination thereof.

In some embodiments, the pharmaceutical compositions may be delivered to the circulation through the digestive system, via intragastric or oral administration. In some embodiments, the pharmaceutical compositions may be administrated by injection or infusion.

In some embodiments, the pharmaceutical composition may be administered directly to the target of interest. In some embodiments, the administration may be in close proximity to the tumor to be treated, for example, by injection.

In another aspect of the present invention, there is provided a use of the co-assembled nanoparticles as described hereinabove in the preparation of a pharmaceutical composition. In some embodiments, the pharmaceutical composition may be used for medical treatment as described hereinabove.

In yet another aspect, the present invention provides a kit comprising the co-assembled nanoparticles according to the principles of the present invention or the pharmaceutical composition comprising same, and optionally further comprising a physiologically acceptable buffer or excipient and an optional means for delivery of the nanoparticles.

In some embodiments the dry and liquid components may be present in separate containers in the kit, or some of the components may be combined within one container. Each possibility represents a separate embodiment of the invention.

In some embodiments, the physiologically acceptable buffer has pH values of between 4.5 and 8; for example, physiological pH values of about 7.3 to 7.4.

In yet another aspect of the present invention there is provided an injectable solution comprising the aqueous dispersion of the co-assembled nanoparticles or pharmaceutical composition comprising the same as described hereinabove. In some embodiments, there is provided a sterile syringe comprising the solution. The syringe may be for example disposable and thus used once or manufactured for a multi-use routine.

Methods of Preparation of the Co-Assembled Nanoparticles

According to some embodiments, the present invention provides a method of manufacturing a co-assembled nanoparticle, the method comprising the following steps:

(i). providing a liquid solution comprising at least one amphiphilic peptide of 4-40 amino acids comprising at least 2 pairs of alternating hydrophobic/hydrophilic amino acid residues, or a derivative or a salt thereof, wherein the hydrophilic amino acid residue is positively charged and the peptide is capable of forming a β-sheet structure, in a vessel;

(ii). providing an alkaline solution comprising a polypeptide comprising a polyanion;

(iii). mixing together the peptide solution and the polypeptide solution;

(iv). acidifying the solution obtained in step iii; and (v). stirring the solution obtained in step iv for at least 8 hours.

In some embodiments, the method comprises a preceding step of synthesizing the amphiphilic peptides and further purifying said amphiphilic peptides by high performance liquid chromatography. According to some embodiments, the peptide of (i) is provided in a powder form. According to some embodiments, the amphiphilic peptide comprises an amino acid sequence according to Formula I, as presented hereinabove. According to further embodiments, the at least one amphiphilic peptide comprises an amino acid sequence Pro-Lys-(Phe-Lys)$_n$-Pro, wherein n is an integer of 3-7 (SEQ ID Nos: 2, 4, 6, 10, and 12). In a certain embodiment, the polypeptide is g-Polyglutamic acid.

In some embodiments, the polypeptide solution of (ii) has a pH range of about 12-13.5. The alkaline solution is typically an aqueous solution of sodium hydroxide (NaOH).

The mixing step may be performed by means of a magnetic stirrer. The mixing step may further be performed at a room temperature. The phrase "room temperature" as used herein, denotes a temperature of 22±5° C. Typically, equal volumes of the peptide solution and the polypeptide solution are mixed in the mixing step. In additional embodiments, the peptide solution and the polypeptide solution are mixed in a weight ratio of the peptide to the polypeptide of about 0.2:1 to about 2:1. In certain embodiments, the weight ratio between the peptide and the polypeptide is 0.75:1 to 1.25:1.

Solution comprising the mixture of peptide and the polypeptide is typically acidified to a pH of about 7-8. The solution may be further stirred according to step v at a room temperature. The solution of step v may further be centrifuged to separate large aggregates from the solution. The centrifugation step may be followed by a filtering step, wherein the supernatant of the solution is passed through a syringe driven filter unit.

In further embodiments, the solution is concentrated by centrifugal filtration and the solution that does not pass the filter membrane is resuspended in a physiologically acceptable buffer.

According to some embodiments, the method further comprises a step of providing a solution comprising a pharmaceutically active ingredient. In further embodiments, the method comprises a step of mixing the solution comprising a pharmaceutically active ingredient with the peptide solution and/or the polypeptide solution. The solution comprising a pharmaceutically active ingredient can be mixed with the peptide solution prior to mixing the polypeptide solution with the peptide solution. In some embodiments, the peptide solution is mixed with the pharmaceutically active ingredient solution for at least 8 hours prior to mixing with the polypeptide solution (step iii). The solution comprising a pharmaceutically active ingredient can be mixed with the polypeptide solution prior to mixing the polypeptide solution with the peptide solution. In some embodiments, the polypeptide solution is mixed with the pharmaceutically active ingredient solution for at least 8 hours prior to mixing with the peptide solution (step iii). Alternatively, the solution comprising a pharmaceutically active ingredient can be mixed with the peptide solution and the polypeptide solution following the stirring step (step v). In additional embodiments, a portion of the solution comprising a pharmaceutically active ingredient is mixed with the polypeptide solution and a portion of the solution comprising a pharmaceutically active ingredient is mixed with the polypeptide solution prior to the mixing step (step iii). The mixing of the polypeptide solution with the pharmaceutically active ingredient solution and of the peptide solution with the pharmaceutically active ingredient solution is typically performed for at least 8 hours. According to some embodiments, the pH of a solution comprising the mixture of the peptide, the polypeptide and the pharmaceutically active ingredient is adjusted to about 7-8.

In some embodiments the pharmaceutically active ingredient is amphiphilic. In additional embodiments, the pharmaceutically active ingredient is charged. In further embodiments, the pharmaceutically active ingredient is positively charged. In certain such embodiments, the pharmaceutically active ingredient solution can be mixed with the polypeptide solution at concentrations allowing to reach a positive to negative charge ratio of about 4:1 to about 1:2000. In other embodiments the pharmaceutically active ingredient is negatively charged. In certain such embodiments, the peptide can be mixed with the pharmaceutically active ingredient at a weight ratio of about 50:1 to about 8:1.

The pharmaceutically active ingredients useful in the method of the present invention include, inter alia, anti-cancer agents or mitochondria-acting agents, such as, but not limited to doxorubicin (DOX), Dequalinium (DQA) or Lonidamine, salts, esters and combinations thereof.

In some embodiments, the method of preparing a co-assembled nanoparticle, further comprises a step of adding a solution comprising an additional amphiphilic peptide of 4-40 amino acids comprising at least 2 pairs of alternating hydrophobic/hydrophilic amino acid residues, or a derivative or a salt thereof to obtain an outer coating. Said additional peptide may further comprise a sequence of hydrophobic amino acid residues. According to some embodiments, the additional peptide comprises an amino acid sequence according to Formula II, as presented hereinabove. According to some embodiments, the additional peptide comprises is a scrambled-order peptide corresponding to the peptide of Formula II. According to other embodiments, the additional peptide comprises an amino acid sequence according to Formula I, as presented hereinabove. According to some embodiments, the additional peptide comprises is a scrambled-order peptide corresponding to the peptide of Formula I.

In some embodiments, the method comprises repeating the step of adding the solution comprising the additional peptide. In certain embodiments, the method comprises repeating the step of adding the solution comprising the additional peptide at least twice. In other embodiments, the method comprises repeating the step of adding the solution comprising the additional peptide until obtaining a nanoparticle having a positive zeta potential. Therefore, according to some embodiments, the outer coating comprises one layer of the additional amphiphilic peptide or two or more layers of said peptide. Each possibility represents a separate embodiment of the invention. Repeating the step of adding the solution comprising the additional peptide can be preceded by separating the additional peptide, which did not form a coating, from the reaction solution by centrifugal filtration.

As used herein and in the appended claims the singular forms "a", "an," and "the" include plural references unless the content clearly dictates otherwise. Thus, for example, reference to "a sample" includes a plurality of such samples and so forth. It should be noted that the term "and" or the term "or" are generally employed in its sense including "and/or" unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in the specification and the appended claims, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: Preparation and Characterization of the Co-Assembled Peptide-Polypeptide Nanoparticles All peptides were synthesized and then purified by high performance liquid chromatography to 95% (Genscript). Four amphiphilic and cationic peptides, thirteen residues in length, having different secondary structure were screened to select the one most suitable for generating the nanoparticles (NPs). A proline capped version—(PK(FK)$_5$P), also termed PFK, corresponding to SEQ ID NO:2; free termini version FK(FK)$_5$F, also termed FK, corresponding to SEQ ID NO:1; and their corresponding scrambled ordered peptides, rPFK (KFFPKKPFKFFKK), corresponding to SEQ ID NO:16; and rFK (KFFFKKFFKFFKK), corresponding to SEQ ID NO:17. PKF peptide has been previously used by some of the inventors of the present invention in the peptide-assisted assembly of Au fiber films [T. P. Vinod, Sh. Zarzhitsky, A. Morag, L. Zeiri, Y. Levi-Kalisman, H. Rapaport and R. Jelinek. Nanoscale, 2013, 5, 10487-10493]. An FITC N-termini PFK peptide was incorporated into nanoparticles to enable fluorescence measurements.

Polypeptide γ-PGA was purchased from Wako Chemicals (200-500 KDa, Tokyo, Japan). Lonidamine was purchased from Abcam (Cambridge, USA). Centrifugal filtration tubes were purchased from Sartorius stedim (vivaspin 6 30,000 MWCO), syringe driven filter units purchased from Merck Millipore (Millex GV 0.22 µm). Unless otherwise specified, all reagents were purchased from Sigma-Aldrich (Rehovot, Israel) and were of the highest available purity. All solutions were prepared with deionized water (DIW) (18.2 MΩ·cm, Direct Q-5 Merck Millipore, Billerica, Mass.).

Peptide-polypeptide NPs were prepared using self-assembly methods under magnetic stirring at room temperature. The polypeptide γ-PGA, 1 mg/ml, can be dissolved in aqueous solution of NaOH (pH 12.9). Peptides solutions were prepared by dissolving a dry powder of the stock peptide (95% purity, synthesized by Genscript) at 1 mg/ml concentration, in DIW. 2 ml of the solution was supplemented with equal volume of the peptide solution and stirred (magnetic stirrer) at room temperature. The polypeptide-peptide solution was then acidified by aliquots of 0.1N HCl to pH 7.4 (at this point the solution becomes slightly turbid) and then left stirring at room temperature overnight.

Figure 4:
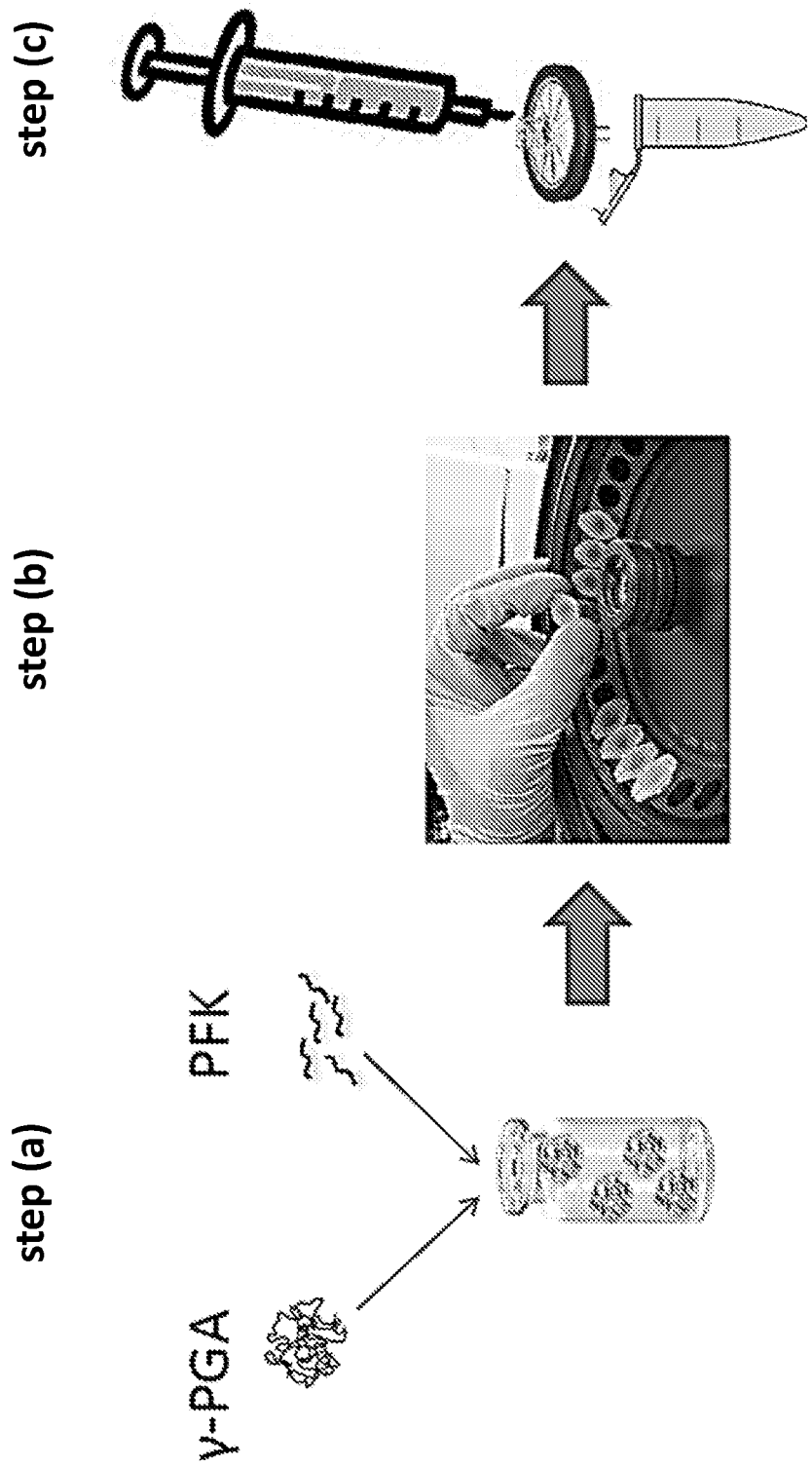
FIG. 4 shows a schematic representation of the nanoparticles preparation process, including: step (a)—aqueous solutions of peptide and γ-PGA are stirred overnight leading to peptide-polypeptide self-assembled forms in a range of sizes, step (b)—large assemblies are removed using centrifuge and step (c)—filtration through 0.22 μm pores.

Large aggregates were then separated from the solution using centrifuge at 4,100 rpm for 20 min. Following the centrifugation, the supernatant was passed through a syringe driven 0.22 µm pore filter unit. FIG. 4 shows a schematic representation of the nanoparticles preparation procedure.

CD measurements were performed to characterize secondary structure of peptides in the NPs solution. Spectra in the range of 190-260 nm were recorded at room temperature on CD spectropolarimeter (J-715, Jasco, Tokyo, Japan), using a 1-mm quartz cuvette.

Figure 5A:
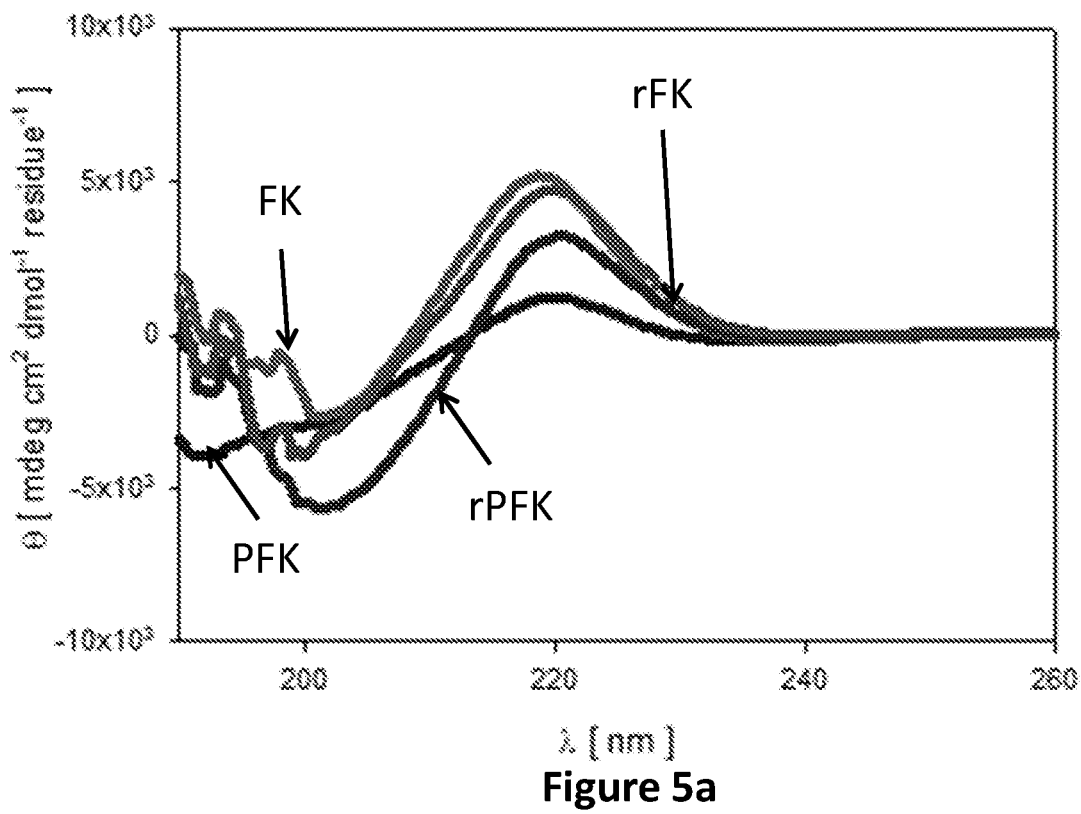
FIG. 5a shows circular dichroism (CD) spectra of 0.5 mg/ml PFK (SEQ ID NO:2), FK (SEQ ID NO:1), rPFK (SEQ ID NO:16) and rFK peptide (SEQ ID NO:17) solutions.
Figure 5B:
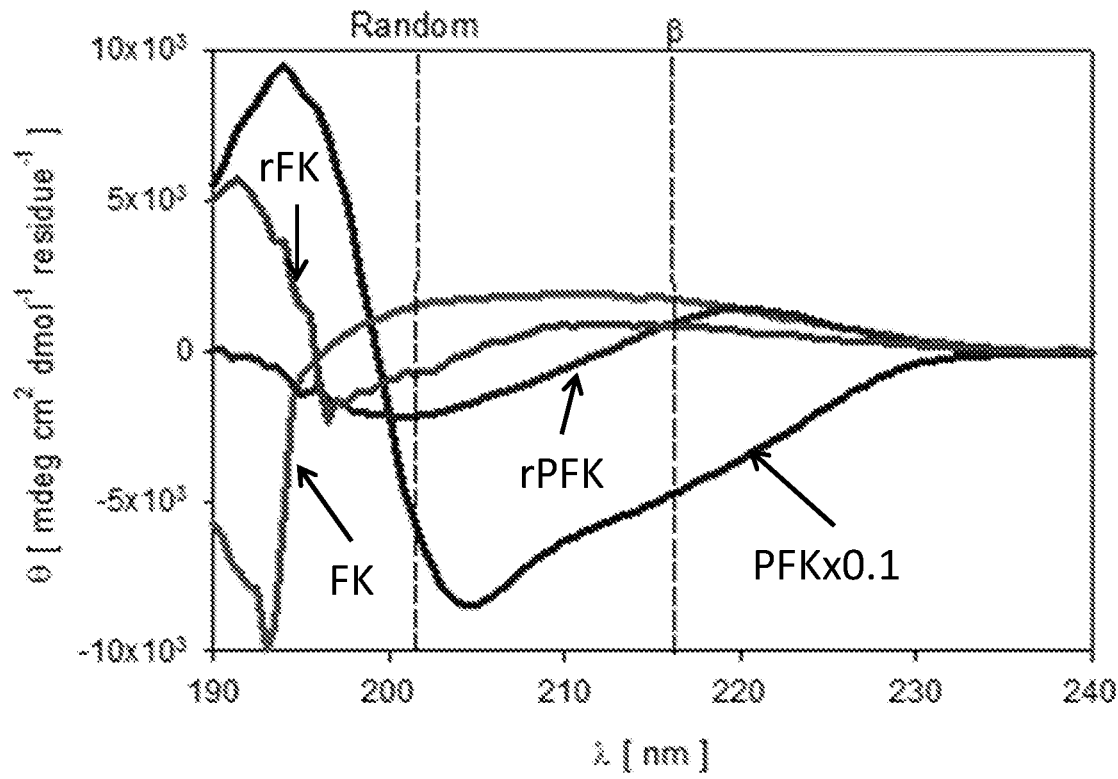
FIG. 5b shows CD spectra of nanoparticles comprising PFK (SEQ ID NO:2), FK (SEQ ID NO:1), rPFK (SEQ ID NO:16) and rFK (SEQ ID NO:17) peptides co-assembled with γ-PGA at a weight ratio of 1:1 (γ-PGA:peptide).
Figure 5C:
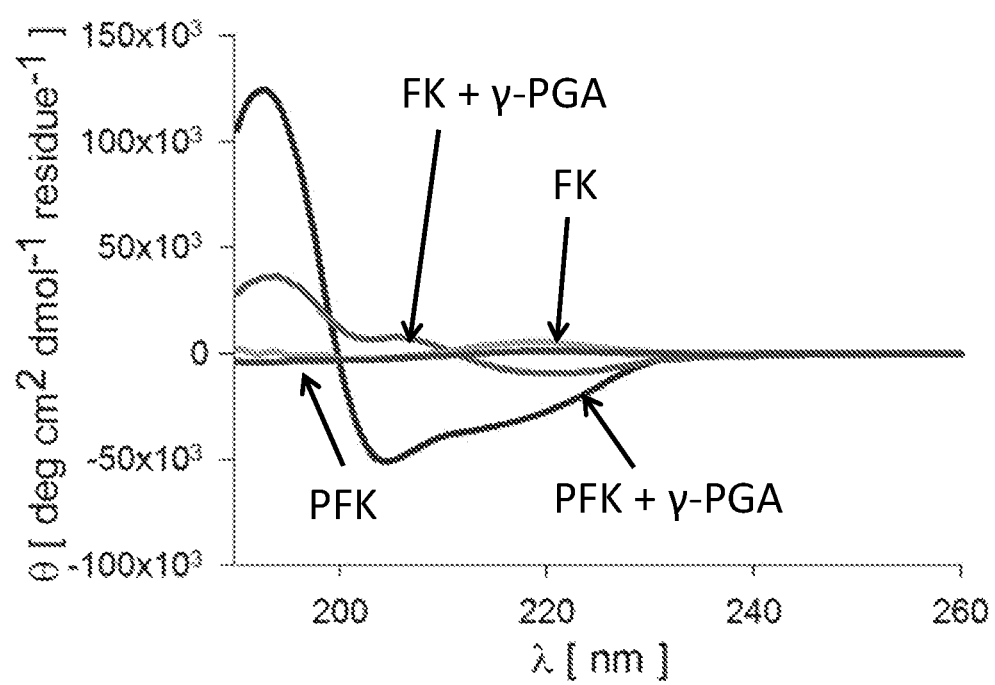
FIG. 5c shows CD spectra of PFK (SEQ ID NO:2) and FK (SEQ ID NO:1) peptides as is, and supplemented with γ-PGA at pH 7.4 (1:1 (w:w)).

All four peptides appeared unfolded in 0.5 mg/ml aqueous solutions, according to a positive CD peak at around 220 nm and a negative one at 200 nm (FIG. 5a and FIG. 5c (PFK and FK peptides). The peptides that exhibited the most pronounced shift to β-sheet structure, on mixing with γ-PGA (0.25:0.25 mg/ml) were PFK (SEQ ID NO:2) and FK (SEQ ID NO:1) (FIG. 5b and FIG. 5c). Between these two, in the PFK (SEQ ID NO:2) mixture a deeper negative absorption at 215 nm (FIG. 5c) was obtained suggesting more influence of the polypeptide on induction of β-sheet formation by PFK peptide compared to peptide FK (SEQ ID NO:1). The CD spectrum of FK in presence of γ-PGA, appears to show a negative absorption at 215 nm overlaid with and a positive absorptions in the 205-210 nm range. Positive CD absorptions in this range most probably correspond to Phe-Phe side chains, stacking interactions which cannot be stabilized in β-sheet assemblies. Therefore the CD pattern of FK in presence of γ-PGA indicates two coexisting states of FK peptide, in β-sheets and in other unknown conformation stabilized by Phe-Phe side chain interactions. The control peptide rPFK in presence of the polypeptide showed almost no change in its CD pattern whereas rFK showed primarily the Phe-Phe side chain type of absorption (FIG. 5b).

NPs diameter was measured by dynamic light scattering (DLS) (CGS-3 LSE-5003, ALV, Langen, Germany) at different angles of the detector (90, 60 and 30 degrees) and by Small angle X-ray scattering (SAXS) (SAXLAB's GANE-SHA 300 XL, Skovlunde, Denmark) Sealed Tube Generator: Cu-Ka 0.154 nm (Genix 3D) equipped with a 2D detector (Pilatus 300k). Surface charge was measured by Zetasizer (Zetasizer Nano ZS, Malvern, Worcestershire, UK) and subsequently the data was analyzed using the Smoluchowski model.

PFK (SEQ ID NO:2) and γ-PGA that were co-assembled in 1:1 w/w ratio showed homogeneous size in DLS measurements, 11.4±2 nm with a negative surface charge of −49.3±2 mV (table 1)), significantly larger from those measured for pure γ-PGA (4.7±2 nm). PFK/γ-PGA NPs have a mean particle size, which is suitable for intracellular delivery. NPs formed in similar manner with the other three peptides, FK (SEQ ID NO:1), rPFK (SEQ ID NO:16) or rFK (SEQ ID NO:17), in 1:1 w/w ratio with γ-PGA were found to be in general smaller in size (Table 1).

TABLE 1

Mean particle sizes and zeta potential values of γ-PGA and Peptide/γ-PGA NPs (n = 9).

| Peptide | SEQ ID NO: | $R_h$* [nm] | ζ [mV] |
|---|---|---|---|
| γ-PGA | — | 4.7 ± 2 | −28 ± 7 |
| PFK | 2 | 11.4 ± 2 | −49.3 ± 2 |
| FK | 1 | 7.41 ± 1.7 | −43.71 ± 9.2 |
| rPFK | 16 | 9.57 ± 6 | −25.26 ± 8.79 |
| rFK | 17 | 6.45 ± 1.2 | −38.78 ± 3.92 |

*$R_h$ represents the most common radius that measured at 90° using DLS.

Based on the results described herein PFK/γ-PGA NPs were selected for future research.

Example 2: Preparation of the Co-Assembled Peptide-Polypeptide Nanoparticles with Varying Weight Ratios of the Peptide and Polypeptide The peptide selected based on the described above screening, PFK (SEQ ID NO:2), was mixed at different ratios with γ-PGA to verify the best combination that generated isotropically shaped NPs at appropriate size range. The nanoparticles were prepared and characterized according to the procedures and techniques described in Example 1. PFK and γ-PGA were mixed at 0.2:1, 1:1, 2:1 w/w ratios by adding 1 ml of γ-PGA solution (1 mg/ml) to 1 ml PFK peptide solutions at different concentrations (0.2, 1.2 mg/ml) resulting in final concentrations of 0.5 mg\ml γ-PGA and 0.1, 0.5, 1 mg/ml PFK.

Figure 6A:
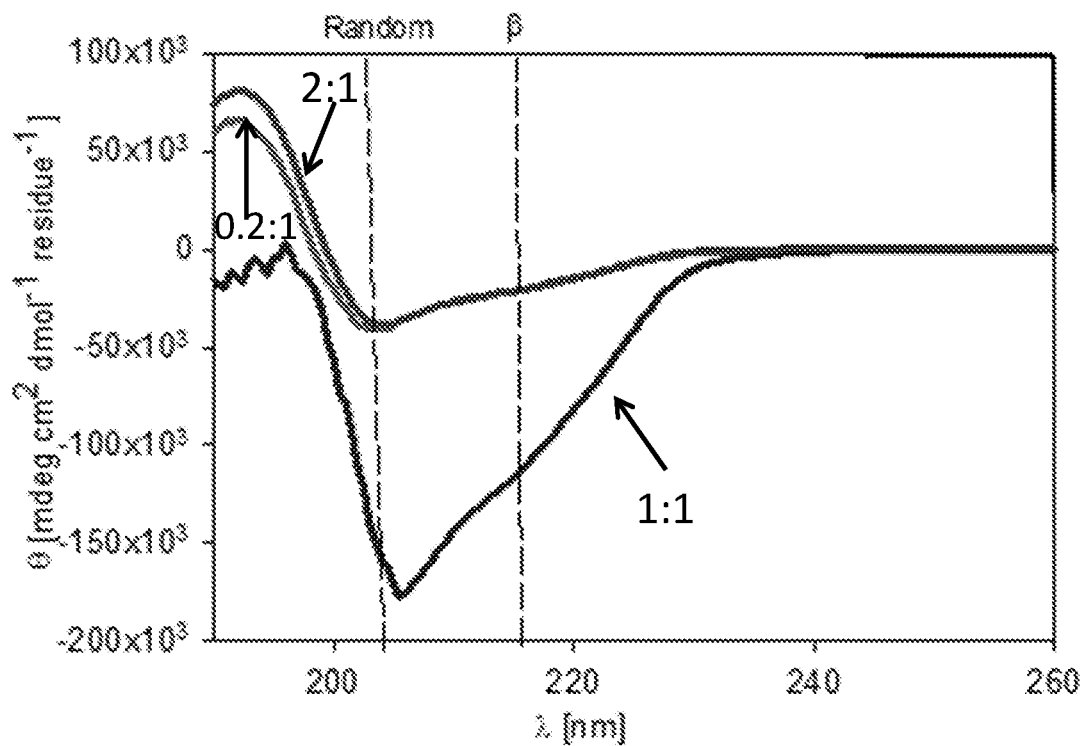
FIG. 6a shows a CD spectra of nanoparticles with different PFK (SEQ ID NO:2): γ-PGA weight ratios.
Figure 6B:
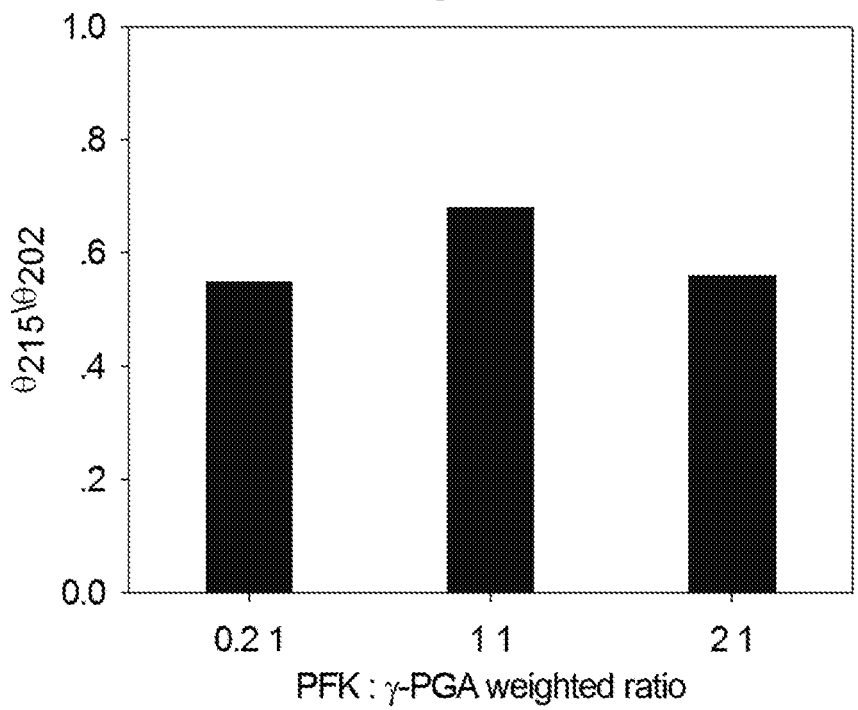
FIG. 6b shows the fraction of β-sheet relative to random structure (0215/0202), as a function of PFK (SEQ ID NO:2): γ-PGA weight ratios.
Figure 7A:
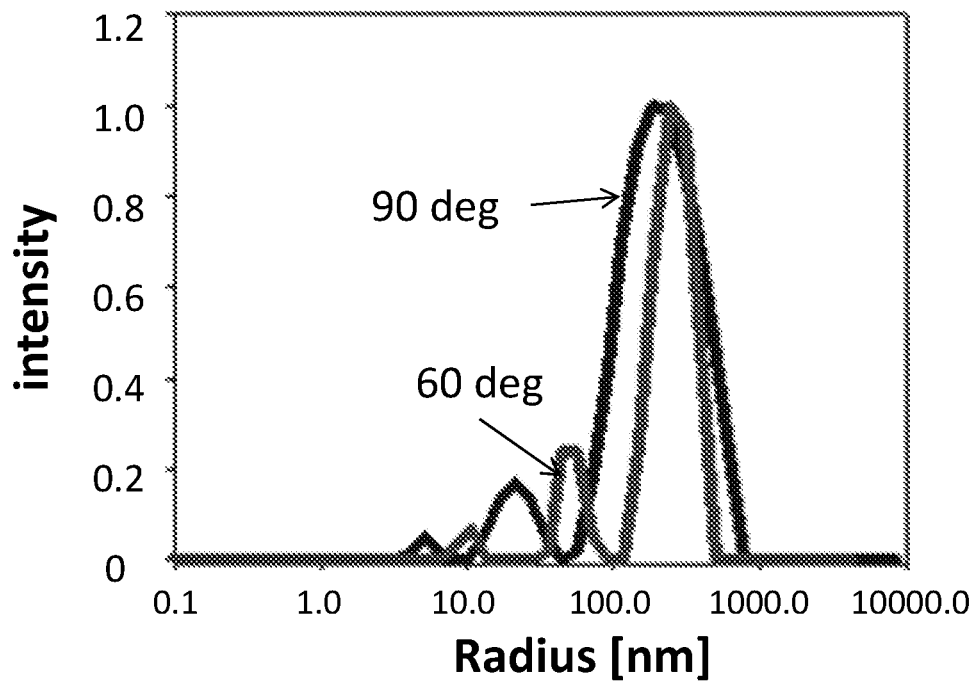
FIG. 7a shows the nanoparticles radius ($R_h$) based on the dynamic light scattering (DLS) measurements of nanoparticles with 0.2:1 PFK (SEQ ID NO:2): γ-PGA weight ratio
Figure 7B:
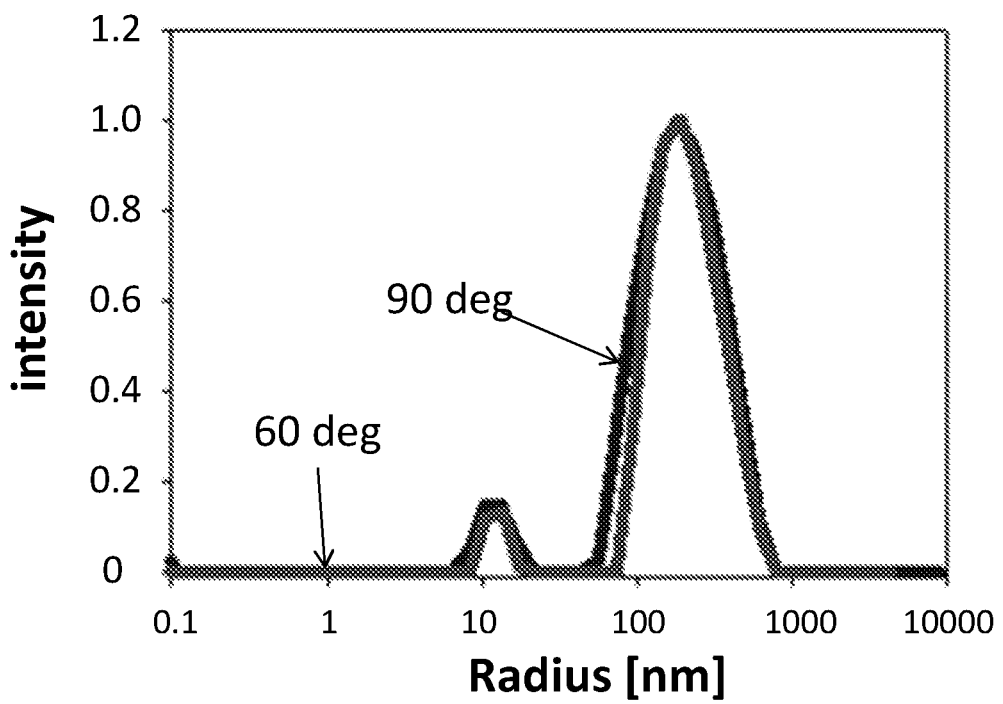
FIG. 7b shows $R_h$ based on DLS measurements of nanoparticles with 1:1 PFK (SEQ ID NO:2): γ-PGA weight ratio
Figure 7C:
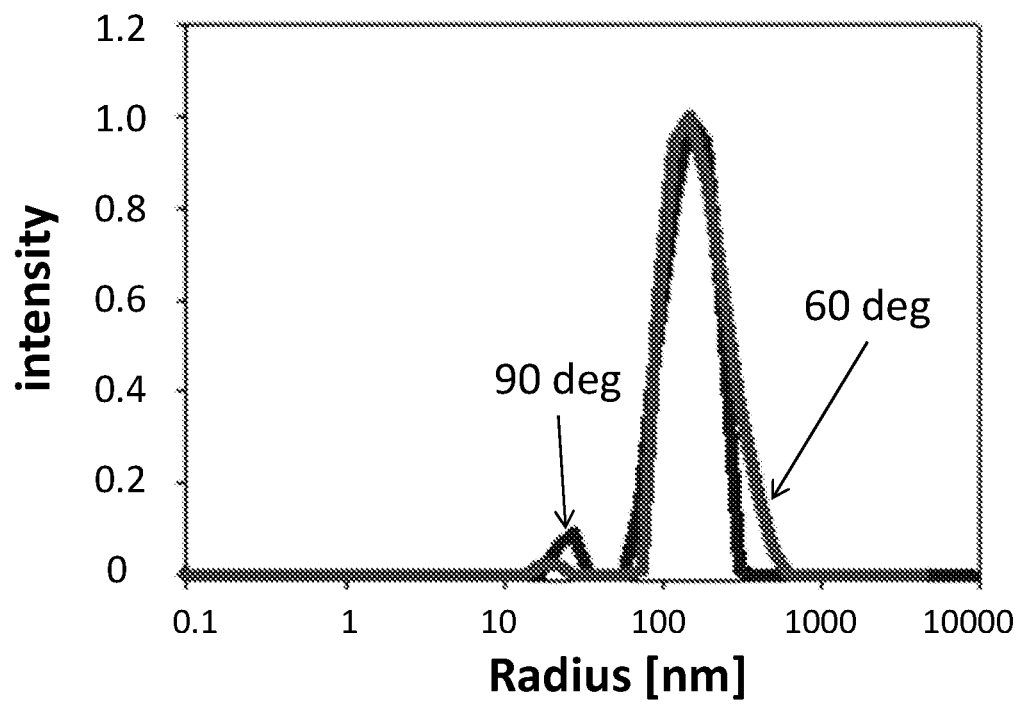
FIG. 7c shows $R_h$ based on DLS measurements of nanoparticles with 1:2 PFK (SEQ ID NO:2): γ-PGA weight ratio
Figure 7D:
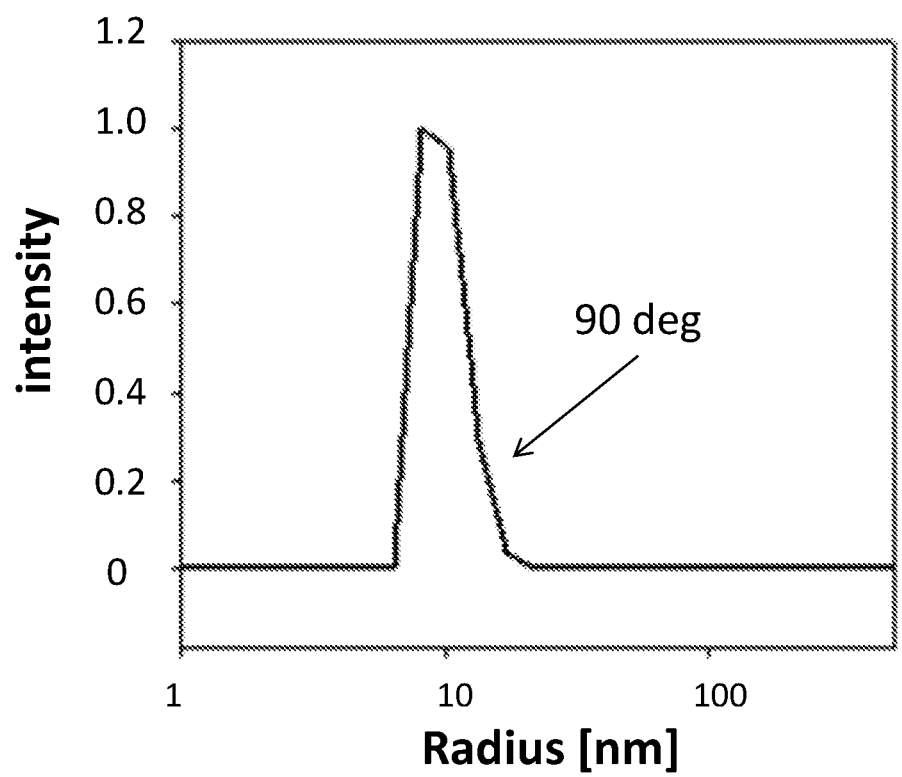
FIG. 7d shows the most common radius of nanoparticles with 1:1 PFK (SEQ ID NO:2): γ-PGA weight ratio based on DLS measurements.

The ellipticity absorption curves measured with 0.2:1 and 2:1 (w:w) PFK: γ-PGA were similar, whereas the 1:1 (w:w) PFK: γ-PGA exhibited generally deeper spectrum (FIG. 6a). The ratio of the absorption at 215 nm relative to that at 202 nm (0215/0202) was used to estimate the extent of peptides in the β-sheet conformation, relatively to the unfolded structure. Data suggest the highest ratio when the NPs formed with 1:1 PFK: γ-PGA weight ratio (FIG. 6b).

Particle sizes and zeta potential values of the nanoparticles formed with different weight ratios of the peptide and the polypeptide are presented in Table 2.

TABLE 2

Mean particle sizes and zeta potential values of
PFK (SEQ ID NO: 2)/γ-PGA NPs with different weight ratios (n = 3).

|  | Radius [nm] | ζ [mV] |
|---|---|---|
| PFK | Non spherical NPs | 11.6 ± 5 |
| 0.2:1 | Non spherical NPs | −53.4 ± 2 |
| 1:1 | 11.45 ± 2 | −49.2 ± 2 |
| 2:1 | 20.6 ± 3.4 | −41.0 ± 0.3 |

*$R_h$ represents the most common radius that measured at 90° using DLS.

NPs diameter was measured by dynamic light scattering (DLS) at different angles of the detector. While 0.2:1 PFK/γ-PGA NPs have different radii when DLS measured at different angles, 1:1 and 2:1 PFK/γ-PGA NPs have same radii, suggesting isotropic shape (FIGS. 7a-7d).

TABLE 3

Mean particle sizes measured using DLS ($R_h$) and SAXS ($R_g$) (n = 3).

| $R_g/R_h$ | $R_g$ [nm] | $R_h$ [nm] |
|---|---|---|
| 0.85 | 9.75 ± 1.2 | 11.45 ± 2 |

Similar results were obtained by SAXS which indicated an average gyration of radius ($R_g$) equal to 9.75±1.2 nm. The ratio between $R_g$ and $R_h$, 0.855, as presented in table 3 supports the formation of spherical NPs (values close to 0.773, 1.8 and 2 are attributed to spherical shape, polydispersed linear coil, and a rod-like linear chain NPs respectively).

Considering CD and DLS results 1:1 (w/w) PFK/γ-PGA NPs were selected as the optimal NPs for intracellular drug delivery.

Figure 8A:
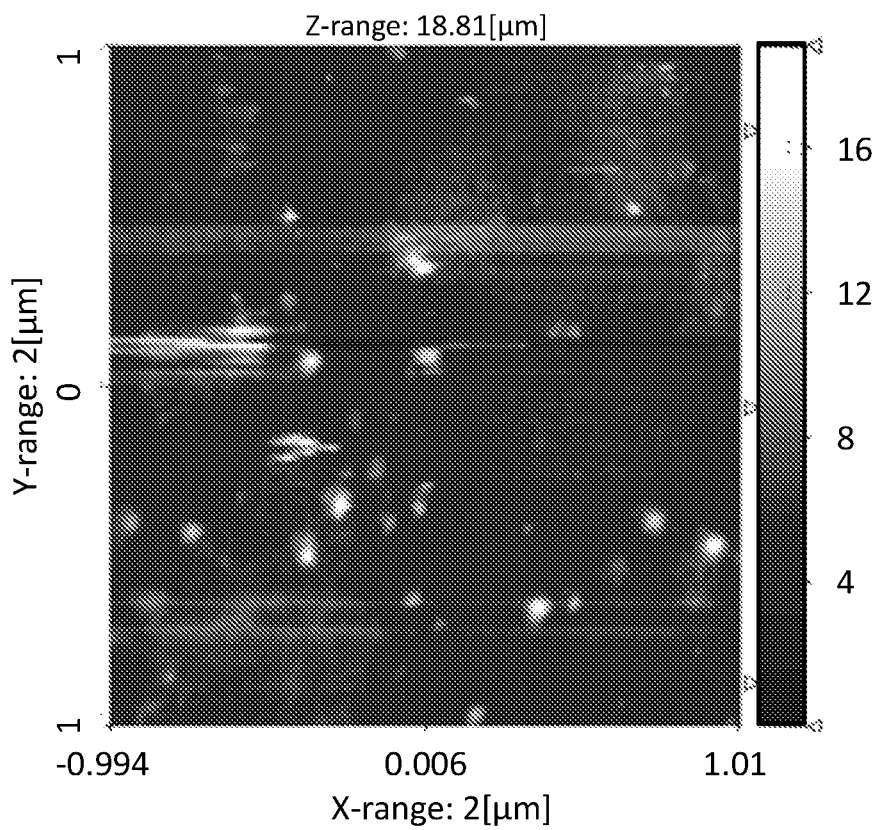
FIG. 8a shows nanoparticles with a ratio of 1:1 (w:w) PFK (SEQ ID NO:2): γ-PGA characterized by atomic force microscopy (AFM).

Self-assembled NPs were further imaged by atomic force microscopy (AFM) on mica substrate using Dimension 3100SPM, Digital Instruments Veeco, New York, USA. 10 μl of NPs solution was deposited on freshly cleaved mica substrate, 10 μl of 10 mM $NiCl_2$ was added in order to enhance the adhesion of NPs to mica surface. Atomic force microscopy images were taken at room temperature using the tapping mode. NPs solution deposited on mica substrate, as evaluated by atomic force microscopy scans, appeared to be spherical in shape (FIG. 8a) with average radii of 9.6±3.0 nm.

Figure 8B:
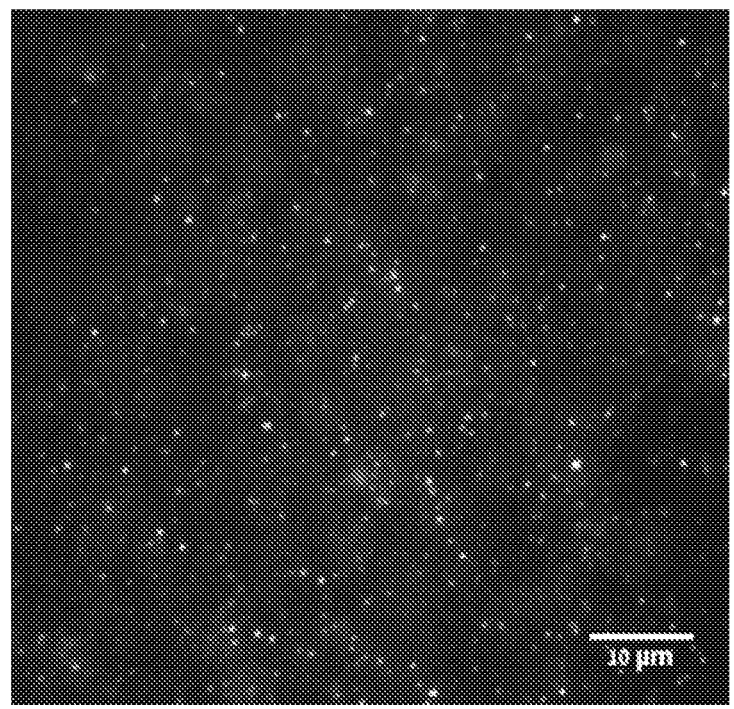
FIG. 8b shows nanoparticles with a ratio of 1:1 (w:w) PFK (SEQ ID NO:2): γ-PGA characterized by total internal reflection fluorescence microscope (TIRFM). NPs are labeled with FITC.

Self-assembled NPs were also imaged in a solution by Total internal reflection fluorescence microscope (TIRFM), using Axioplan2 Zeiss objective 60× oil, 1.45NA (Zeiss, Berlin, Germany). Images were acquired with EMCCD ixon3 camera (Andor technology, Belfast, UK). NPs were prepared as described above but with 10% weight of peptide replaced with PFK labeled with FITC (N-termini). An aqueous γ-PGA 4 ml solution was added to an aqueous PFK (10% PFK-FITC) 4 ml solution as describe before. The solution was then filtered using centrifugal filtration tubes with 30,000 MWCO membrane at 4100 rpm for 30 min to get rid of free peptide. The NPs which did not pass the filter were resuspended in DIW. The TIRFM micrograph of the 1:1 PFK:γ-PGA nanoparticles is presented in FIG. 8b.

Example 3: Co-Assembled Peptide-Polypeptide Nanoparticles Stability Over Time PFK (SEQ ID NO:2):γ-PGA (1:1 w/w) NPs prepared as described in Example 1 were left in solution for one month under different conditions: solution refrigerated, solution in freezer or first freeze dried then lyophilized and kept in freezer. Samples were characterized by DLS as described hereinabove.

The NPs remained substantially unchanged when stored for more than one month at different conditions, as presented in Table 4.

TABLE 4

Mean particle sizes of PFK (SEQ ID NO: 2)/
γ-PGA NPs stored for about a month.

|  | Radius [nm] |
|---|---|
| Fresh NPs solution | 11.45 |
| Freezer | 11.6 |
| Refrigerator | 9.85 |
| Lyophilized and freeze-dried | 6.54 |

*$R_h$ represents the most common radius that measured at 90° using DLS.

Example 4: Co-Assembled Peptide-Polypeptide Nanoparticles Stability in Physiologically Acceptable Buffer In order to examine the stability of PFK (SEQ ID NO:2):γ-PGA (1:1 w/w) NPs in physiological-like conditions, NPs were prepared as described in Example 1 and then concentrated using centrifugal filtration (pore size 30 KDa) at 4,100 rpm for 30 min, and material which did not pass the filter was resuspended in 2 ml TBS (pH 7.4, 150 mM NaCl).

The most common size of NPs at 90° was $R_h$=18.97±6.9 nm and zeta potential was −37.71±1.9.

Figure 9A:
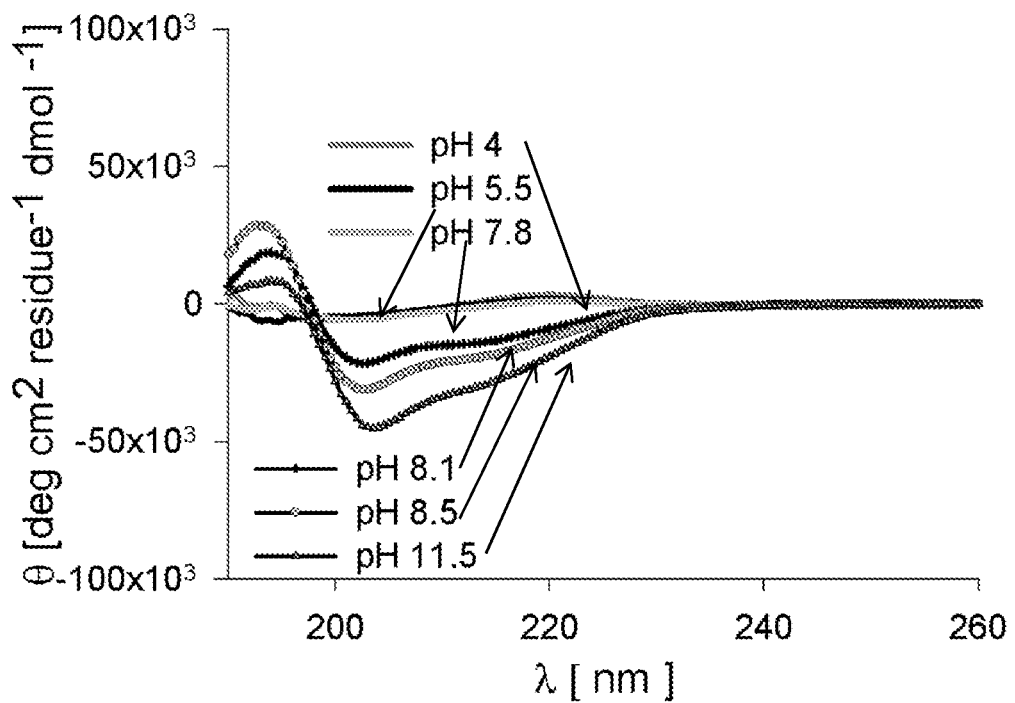
FIG. 9a shows CD spectra of 0.5 mg/ml PFK (SEQ ID NO:2) at pH values of 4, 5.5, 7.8, 8.1, 8.5, and 11.5.
Figure 9B:
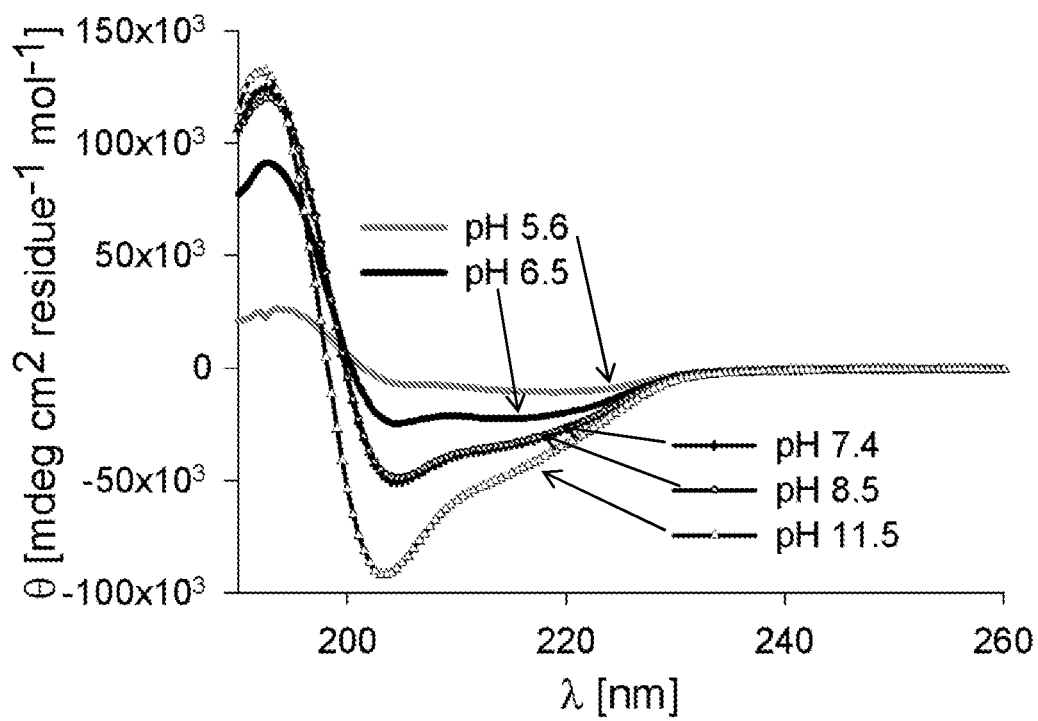
FIG. 9b shows CD spectra of 0.125 mg/ml PFK (SEQ ID NO:2) with 0.125 mg/ml γ-PGA at pH values of 5.6, 6.5, 7.4, 8.5, and 11.5.
Figure 9C:
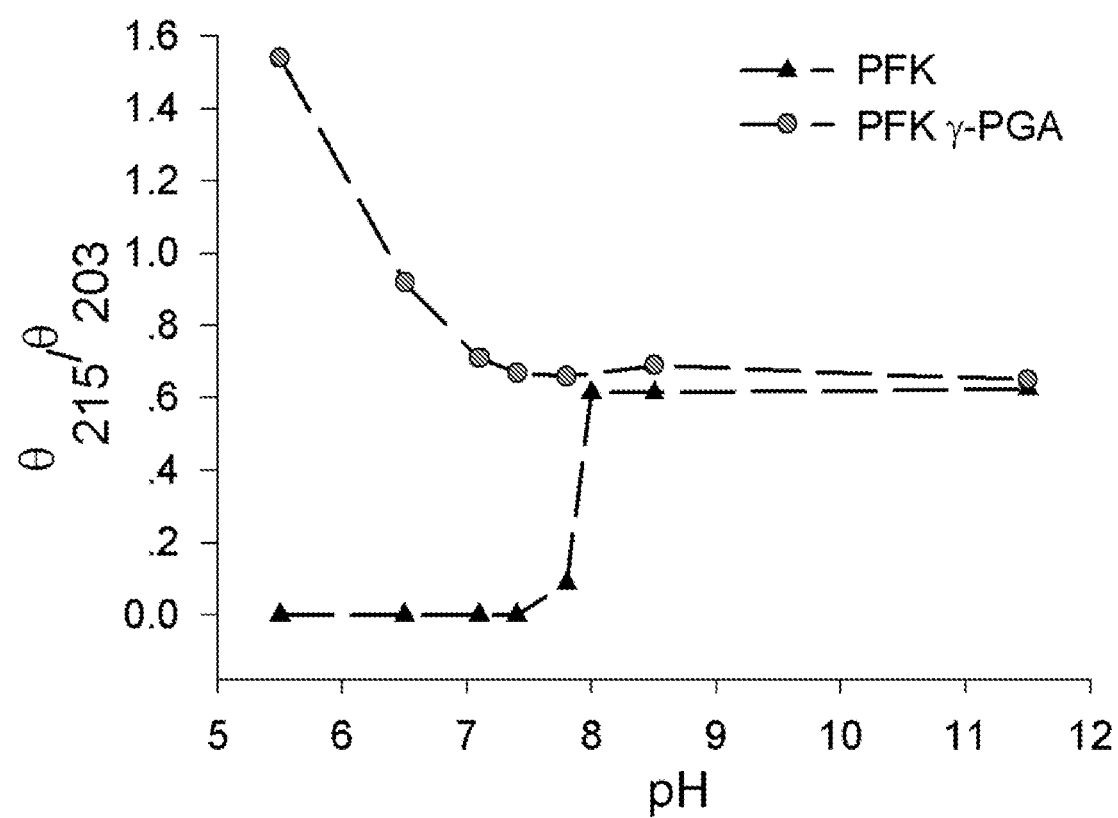
FIG. 9c shows the fraction of β-sheet relative to random structure assessed by $\theta_{215}/\theta_{203}$, as a function of pH for PFK (SEQ ID NO:2) (▲) and PFK (SEQ ID NO:2) with γ-PGA (●).

Example 5: Co-Assembled Peptide-Polypeptide Nanoparticles Stability at Different pH Values The influence of pH on the secondary structure of PFK peptide (SEQ ID NO:2) and its 1:1 w/w mixture with γ-PGA was further studied by CD measurements. PFK (SEQ ID NO:2) solutions adjusted to pH 4-7.8 exhibited absorbance spectra typical of unfolded conformation, with positive and negative peaks at 220 and 203 nm, respectively. At pH values >8.1 the spectra indicated coexistence of β-sheet and unfolded structures (FIG. 9a). The 1:1 w/w PFK (SEQ ID NO:2) and γ-PGA mixture (FIG. 9b) showed throughout this range of pH values the CD spectra corresponding to the coexisting unfolded and β-sheet conformation. The ratio between the molar ellipticity at wavelength 215 nm indicative of β-sheet conformation and that at 203 nm corresponding to the unfolded structure ($\theta_{215}/\theta_{203}$) were extracted from the CD spectra to provide a measure for the relative extent of these two states as function of pH (FIG. 9c). PFK exhibited a steep increase in $\theta_{215}/\theta_{203}$ value at pH~8 in accordance with increased tendency to β-sheet structure at the higher pH values. Interestingly, PFK in the presence of γ-PGA showed the opposite trend in $\theta_{215}/\theta_{203}$ as function of pH, indicative of reduced tendency to β-sheet conformation with increase in pH. Without wishing to being bound by theory, this result may be rationalized by the γ-PGA stabilizing effect on PFK through electrostatic interactions which result in higher extent of the peptide in β-sheet structure, in pH 5-8 range (γ-PGA pKa=2.19). These results were considered supportive of the design concept of the co-assembled NPs, which were sought to be stable at pH values lower than neutral to render the NPs stable in the endosome and disintegrate in the mildly high pH values at the matrix environment of the mitochondria.

Example 6: Preparation of the Co-Assembled Peptide-Polypeptide Nanoparticles Comprising a Pharmaceutically Active Ingredient (DQA)

DQA was incorporated into NPs at different stages of the preparation procedure described in Example 1 in order to optimize the drug loading of the nanoparticle that was further evaluated by DLS, CD and zeta potential measurements.

Stock solutions of 1.5 mg/ml of PFK (SEQ ID NO:2) and γ-PGA and $3*10^{-3}$ mM DQA were used in screening of the optimal drug loading method:

1) PFK, DQA and γ-PGA (1 ml of each stock solution) were mixed all together. The solution is then acidified by aliquots of 0.1 N HCl to pH 7.4. The mixed solution was stirred over two nights and then centrifuged at 4,100 rpm for 20 min and passed through syringe driven 0.22 filtered μm filter.
2) PFK and DQA, 1 ml stock solution of each, were first mixed together using magnetic stirrer over night. 1 ml γ-PGA was added, the mixed solution is then acidified by aliquots of 0.1 N HCl to pH 7.4. The mixed solution was stirred overnight and then centrifuged at 4,100 rpm for 20 min and passed through syringe driven 0.22 filtered μm filter.
3) PFK and γ-PGA (1 ml of each stock solution) were first mixed together. Then the PFK γ-PGA solution was acidified by aliquots of 0.1 N HCl to pH 7.4 and left stirring at room temperature overnight. PFK γ-PGA solution was combined with 1 ml DQA stock solution following the same procedure as above.
4) γ-PGA and DQA (1 ml of each stock solution) were first mixed together and then combined with 1 ml PFK stock solution following the same procedure as above.

Figure 10A:
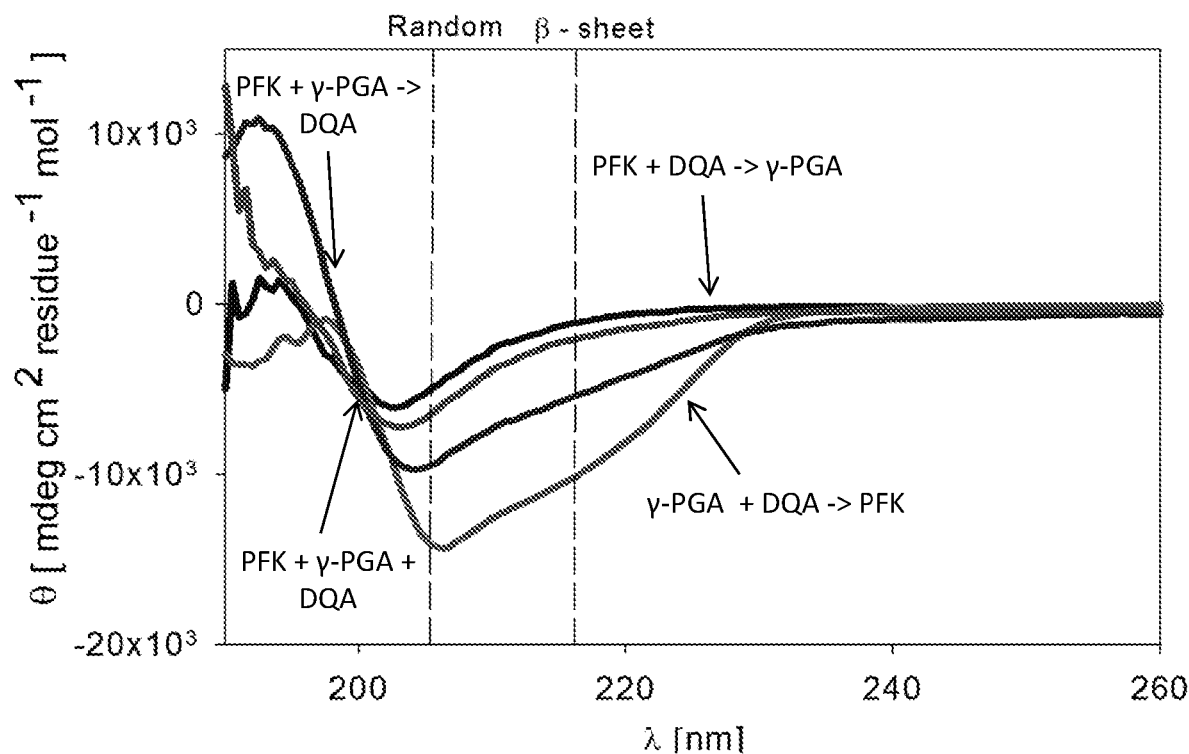
FIG. 10a shows CD spectra of nanoparticles loaded with DQA using different loading techniques, including 1) PFK (SEQ ID NO:2)+DQA+γ-PGA, wherein all the components are mixed together; PFK+DQA→γ-PGA, wherein PFK and DQA are first mixed together and then γ-PGA is added; PFK+γ-PGA→DQA, wherein PFK and γ-PGA are first mixed together and then DQA is added; and γ-PGA+DQA→PFK, wherein γ-PGA and DQA are first mixed together and then PFK is added.
Figure 10B:
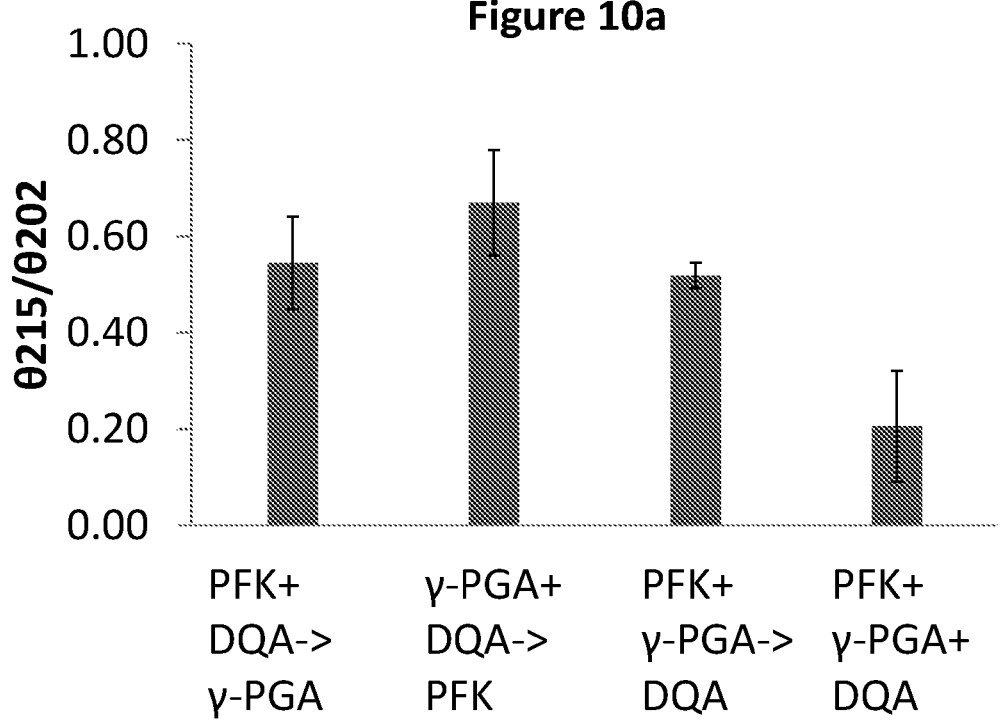

Table 5 summarizes the particle sizes and zeta potential values of the nanoparticles obtained according to the above-described procedures. NPs loaded with DQA that were prepared by mixing γ-PGA and DQA under stirring overnight and then adding PFK (γ-PGA+DQA→PFK) have a deeper absorbance in CD indicating a higher extent of β-sheet secondary structure as compared to the unfolded structure (FIGS. 10a-10b). Moreover NPs are in a size that is suitable for intracellular delivery (Table 5).

TABLE 5

Mean particle sizes and zeta potential values of PFK (SEQ ID NO: 2)/ γ-PGA NPs loaded with DQA (n = 9).

| | Radius ($R_h$) [nm] | ξ [mV] |
|---|---|---|
| PFK + DQA -> γ-PGA | 6.6 ± 1.2 | −26 ± 14.8 |
| γ-PGA + DQA -> PFK | 15.6 ± 5.7 | −46.8 ± 0.7 |
| PFK + γ-PGA -> DQA | 7.4 ± 2.9 | −31.1 ± 3.7 |
| PFK + γ-PGA + DQA | 10.7 ± 5.7 | −23.3 ± 24.7 |

* $R_h$ represents the most common radius that was measured at 90° using DLS.

The initial concentration of the DQA solution (3 mM) and γ-PGA solution (1.5 mg/ml) were chosen to provide a 1:1 positive:negative charge ratio between the therapeutically active ingredient and γ-PGA. However, despite said corresponding concentrations of the encapsulating polypeptide and the drug, only a relative low percent of DQA that was mixed with γ-PGA was found to be loaded into the nanoparticle. Namely, only 0.0092±0.004 mM (n=3) DQA was measured in the NPs solution. These results led to the development of an additional method in which DQA is added to both the peptide and the polypeptide:

5) γ-PGA 1 ml stock solution was mixed with 0.5 ml, 3 mM DQA whereas in a separate vial PFK 1 ml stock solution was mixed with 0.5 ml, 3 mM DQA. Both solutions were allowed to stir overnight, then combined together and adjusted to pH 7.4 with 1 N HCl aliquoting. This mixed solution was left stirred overnight. NPs with size below 220 nm were collected using centrifuge at 4,100 rpm for 20 min, then supernatants were filtered using syringe driven filter units with 0.22 μm pores.

In the NPs prepared according to method 5, the DQA concentration within NPs solution increased to 0.062±0.02 mM. Additionally, the particle size of the NPs obtained according to said method was found to be specifically suitable for the intracellular delivery. The mean particle size ($R_h$) was measured to be 17.83±4.56 nm. Zeta potential (ζ) was −46.3±7.9 mV.

Figure 11:
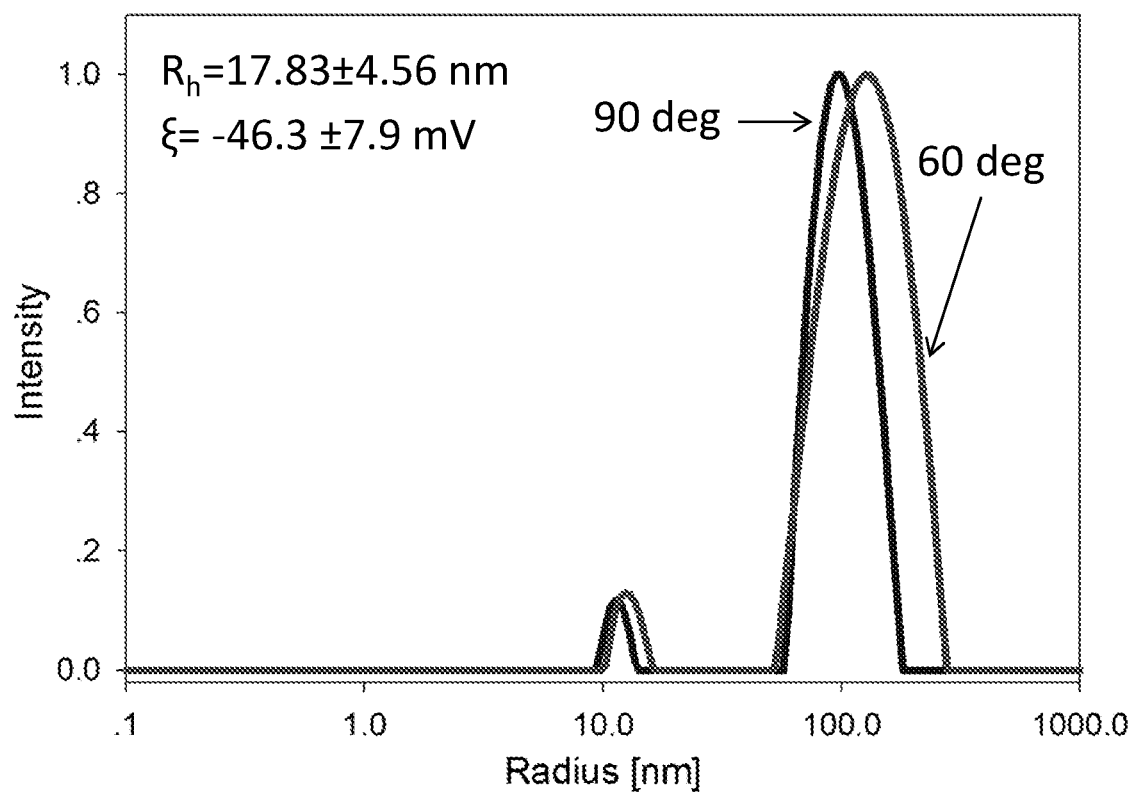
FIG. 11 shows $R_h$ based on DLS measurements of nanoparticles loaded with DQA using the improved loading technique.

The shape of the nanoparticles loaded with DQA was found to be similar to the shape of unloaded particles. Particularly, the loaded nanoparticles were found to be isotropically spherical, as suggested by the results of DLS measurements at different angles, which revealed the same radii, irrespective of the measurement angle (FIG. 11).

Example 7: Preparation of the Co-Assembled Peptide-Polypeptide Nanoparticles Comprising Varying Concentrations of the Pharmaceutically Active Ingredient (DQA)

Figure 12:
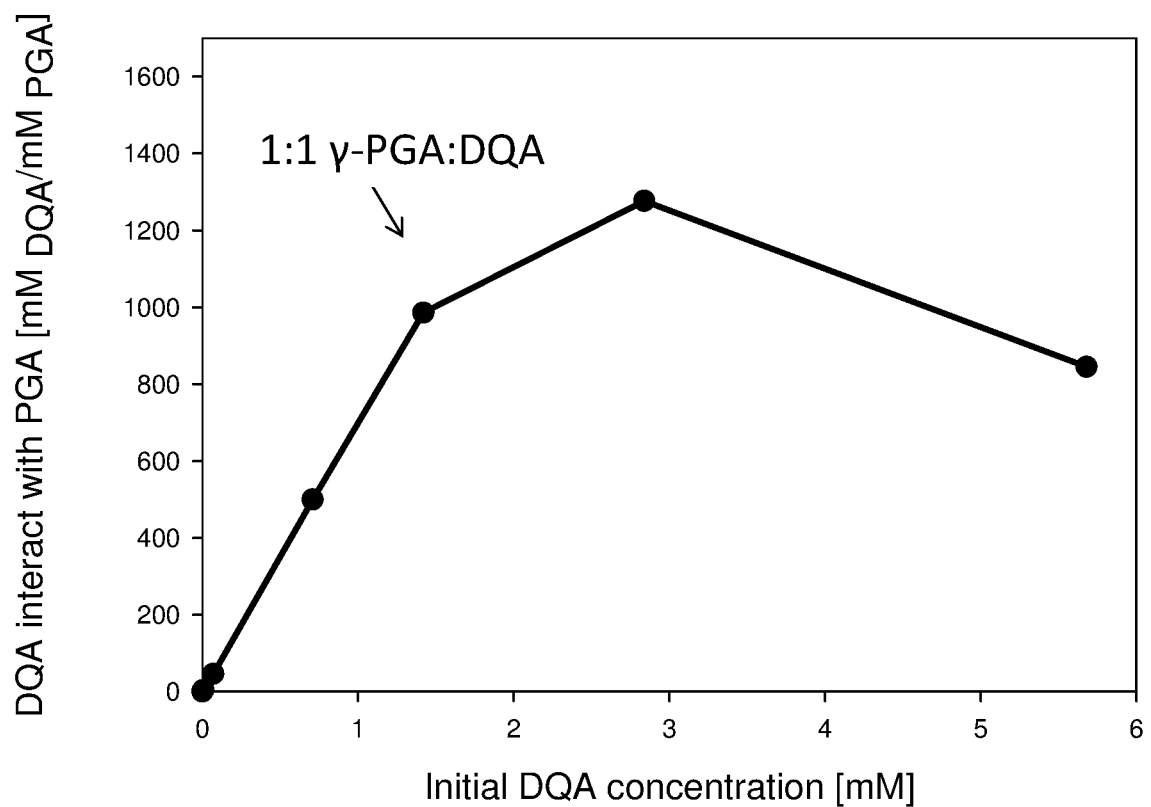
FIG. 12 shows DQA loading capacity; DQA interacts with γ-PGA as a function of initial DQA concentration, wherein 1:1 ratio refers to positive charge of DQA relative to negative charge of γ-PGA.

In order to estimate the amount of DQA that can adsorb or encapsulate, 3 ml of DQA solutions at concentrations of 5.68, 2.84, 1.42, 0.71, $7.1\times10^{-2}$, $7.1\times10^{-3}$, $7.1\times10^{-4}$ mM were mixed with 3 ml γ-PGA 1 mg/ml solution to reach ratios of positive to negative charge (+:−) of 4:1, 2:1, 1:1, 1:2, 1:20, 1:200, 1:2000 between DQA and γ-PGA respectively. 1N HCl aliquots were added to decrease pH to 7.4 and the solution was stirred overnight. Then free DQA was separated from DQA that interacted with γ-PGA using centrifugal filtration with 30,000 MWCO membrane at 4,100 rpm for 30 min. DQA concentration was determined using absorption measurements at 330 nm. FIG. 12 shows DQA loading capacity.

Example 8: The Pharmaceutically Active Ingredient (DQA) Release from the Co-Assembled Peptide-Polypeptide Nanoparticles NPs loaded with DQA, prepared according to method 5 of Example 5 (a total of 5 ml of all components), were separated from free DQA using centrifugal filtration with 30,000 MWCO membrane at 4,100 rpm for 30 min. The nanoparticles were then resuspended in 1 ml DIW. DQA concentration in NPs was measured using microplate-reader (BioTek instruments, Winoosky, Vt.) at 330 nm. The release of DQA from NPs was performed by dialysis against TBS (pH 7.4 150 mM NaCl). A volume of 1 ml of the DQA loaded NPs was mixed with the release medium (1:1, v/v), sealed in a dialysis tube (Spectra Por 6, 1 KDa MWCO), and immersed in 20 ml TBS. A volume of 1 ml of the release medium was sampled at 0.5, 2.5, 3, 6, 21.5 and 24 hr. After each sampling, the same volume of fresh release medium was immediately supplemented into the release tank. The DQA content in the release medium was determined by microplate-reader at 330 nm.

Figure 13:
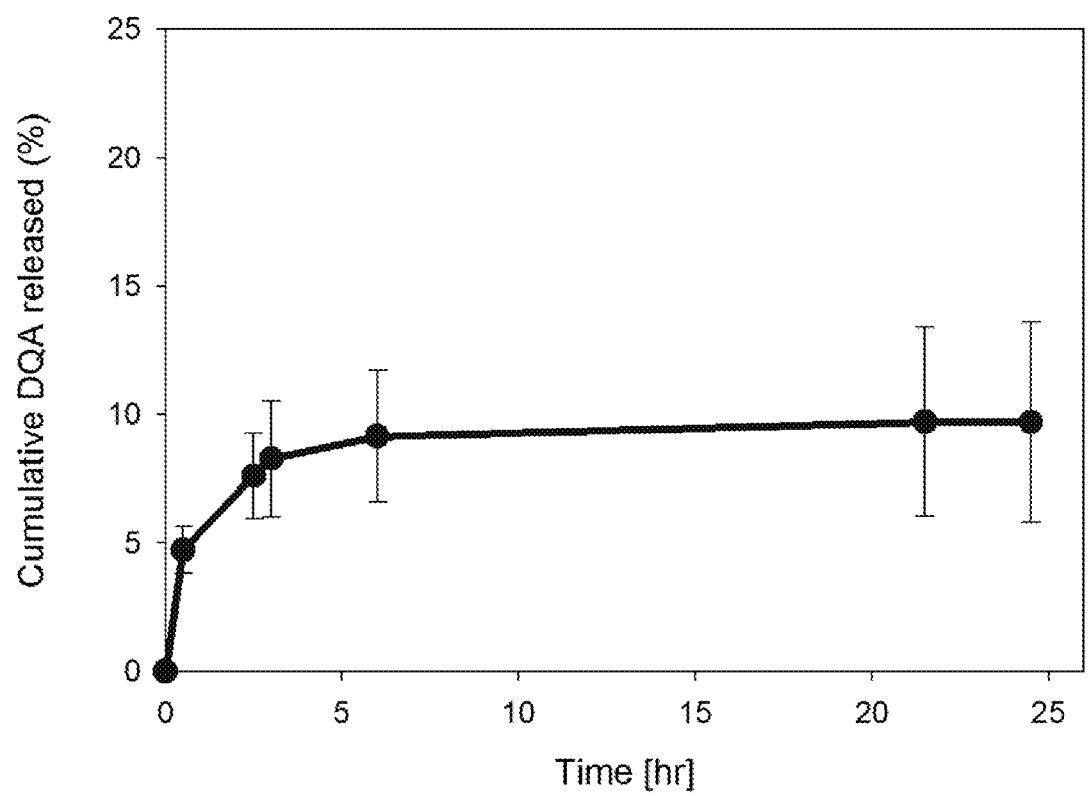
FIG. 13 shows cumulative DQA, released from nanoparticles over time in the release medium of TBS pH 7.4 150 mM NaCl.

FIG. 13 represents a cumulative concentration of DQA released from NPs over 24 hours. The results suggest a controlled release of DQA at pH 7.4.

Example 9: Preparation of the Co-Assembled Peptide-Polypeptide Nanoparticles Coated by Additional Peptide Zeta potential of γ-PGA/PFK NPs is negative, which can decrease the efficiency of NPs penetration through cell membrane. Thus, NPs were coated with different positively charged peptides.

1:1 γ-PGA/PFK NPs were prepared as described in Example 1. 1 ml of the NPs solution was supplemented 1 ml, 0.1 or 0.5 mg/ml of an additional peptide aqueous solution and allowed to stir for 3 hr. The peptides that were screened as coatings were: PFK (SEQ ID NO:2), rPFK (SEQ ID NO:16), $L_4(FK)_3P$ (SEQ ID NO:13), $L_6(FK)_3P$ (SEQ ID NO:15). Coated NPs were characterized by DLS and zetasizer (table 6). Peptides $L_4(FK)_3P$ (SEQ ID NO:13) and $L_6(FK)_3P$ (SEQ ID NO:15), were synthesized and then purified by high performance liquid chromatography to 78% purity By Caslo.

NPs enhanced coating with PFK (SEQ ID NO:2) was also tested. NPs that were coated with PFK (SEQ ID NO:2) as described above were separated from free soluble PFK (SEQ ID NO:2) using centrifugal filtration with 30,000 MWCO membrane at 4,100 rpm for 30 min. 1 ml of the coated NPs was again supplemented with fresh 0.1 mg/ml, 1 ml PFK (SEQ ID NO:2) solution under stirring. This refreshment coating procedure (including the coating and the separation of non coated PFK) was repeated for 2 additional times.

TABLE 6

Mean particle sizes and zeta potential values of NPs coated with the different positively charged peptides (n = 4).

| NPs coated with: | SEQ ID NO: | Conc. of coating solution [mg/ml] | $R_h$ [nm] | ξ [mV] |
|---|---|---|---|---|
| NPs | — | — | 11.45 ± 2 | −44.65 ± 3.7 |
| PFK | 2 | 0.1 | 9.8 ± 0.23 | −33.52 ± 3.11 |
|  |  | 0.5 | 52.2 ± 50.63 | −35.42 ± 4.5 |
| PFK within TBS[b] | 2 | 0.5 | 2254 ± 332 | −28.7 ± 0.54 |
| rPFK | 16 | 0.1 | 11.04 ± 7.77 | −37.26 ± 7.03 |
|  |  | 0.5 | 9.72 ± 1.03 | −36.0 ± 2.69 |
| $L_4(FK)_3P$ [a] | 13 | 0.1 | 13.7 ± 5.6 | −40.77 ± 10.12 |
|  |  | 0.5 | 90.96 ± 25.5 | −38.28 ± 0.54 |
| $L_6(FK)_3P$ [a] | 15 | 0.1 | 25.7 ± 9 | −39.05 ± 1.27 |
|  |  | 0.5 | 1942 ± 0 | −40.5 ± 0.42 |

[a] These peptides are characterized by a hydrophobic "tail" of Leu amino acids and a "head" composed of the b-sheet inducer Phe-Lys dyads. These were tested here in terms of their ability to generate a positive charge coating.
[b] TBS induces the β sheet secondary structure PFK was found to be optimal for coating NPs among the peptides that were examined, nevertheless NPs zeta potential remained negative even when PFK coating concentration was increased (Table 6).

NPs that were subjected to a 0.1 mg/ml PFK solution while repeatedly refreshing the coating solution, were found to become coated with a positively charged surface layer as suggested by the measured positive zeta potential of said nanoparticles (Table 7).

TABLE 7

Mean particle sizes and zeta potential values (n = 4) of NPs coated with PFK (SEQ ID NO: 2).

| NPs coated with: | Rh [nm] | ξ [mV] |
|---|---|---|
| PFK | 9.8 ± 0.23 | −33.52 ± 3.11 |
| PFK repeated addition | 24.4 ± 10 | 11.8 ± 1.1 |

Figure 14:
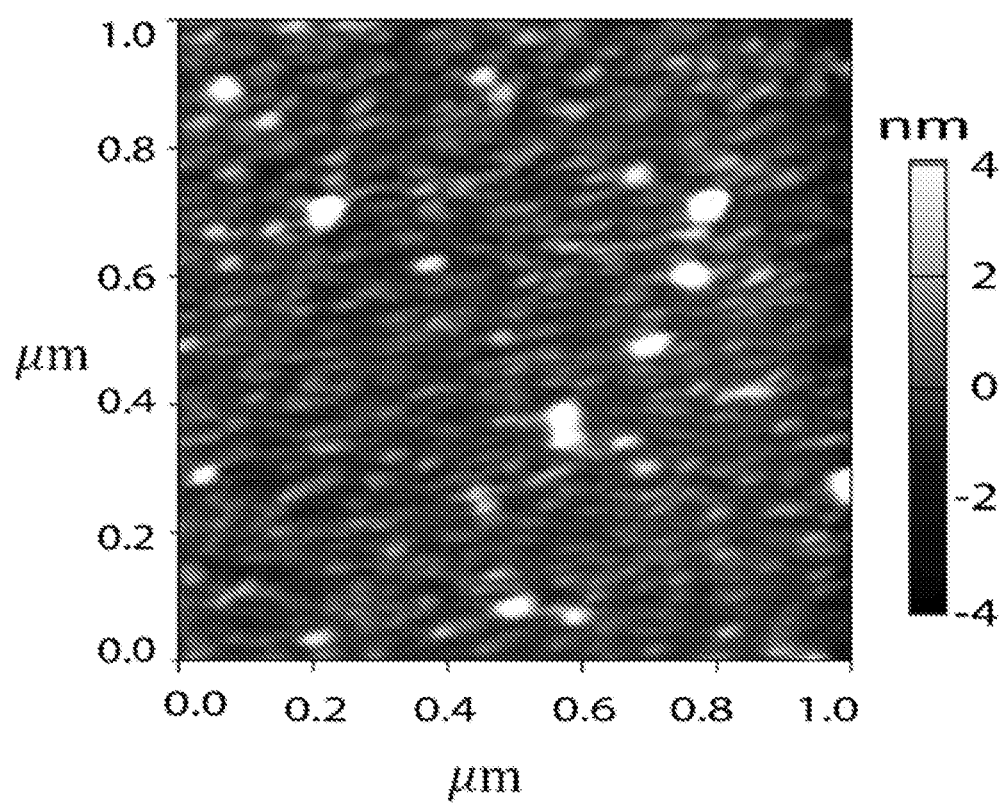
FIG. 14 shows co-assembled nanoparticles coated with an outer coating comprising a PFK peptide (SEQ ID NO:2) characterized by AFM scanning in liquid in tapping mode.

FIG. 14 shows AFM scan of the NPs coated by repeated addition of PFK. Coated NPs appeared to be spherical in shape with an average radius of 19.1±3.9 nm.

Example 10: Localization of the Co-Assembled Peptide-Polypeptide Nanoparticles within Cells The cellular uptake and co-localization of the NPs obtained according to the procedure described in Example 1 composed of γ-PGA and PFK (SEQ ID NO:2) (negatively charged NPs) and same particles coated with PFK (positively charged NPs), obtained according to the procedure described in Example 9, within the mitochondria, were evaluated in human osteosarcoma cell line, Saos2, by confocal microscopy (FIGS. 15a-15f).

Saos2 cells ($3 \times 10^5$ cells/well) were cultured in a confocal dish with DMEM complete medium, under an atmosphere of 5% $CO_2$/air at 3TC for 4 h. Medium was then replaced with medium containing labeled γ-PGA and PFK (SEQ ID NO:2) (negatively charged NPs) and same particles coated with PFK (SEQ ID NO:2) (positively charged NPs), prepared as described above but with 30% weight of peptide replaced with PFK (SEQ ID NO:2) labeled with FITC (FIGS. 15b and 15e, wherein white dots represent green color). Then the NPs were separated from the aqueous solution using centrifugal filtration tubes with 30,000 MWCO membrane at 3000 g for 30 min. The NPs which did not pass the filter were resuspended in phenol red-free complete media. The cells were then incubated under an atmosphere of 5% $CO_2$/air at 37.0 overnight. Then the medium was replaced with fresh medium containing MitoTracker Deep Red 633 (final concentration 100 nM), and the cells were incubated for 40 min to allow the mitochondria to be stained (FIGS. 15a and 15d, wherein grey stain represents red color). Cells were then washed with PBS and the medium replaced with fresh phenol red free medium and then observed by Spinning-disc Confocal System (Axiovert-200M microscope, Zeiss, Germany, equipped with Piezo Z-Axis head).

The coated NPs (FIGS. 15a-15c) showed yellow clusters (represented by the brightest dots and shown by arrows), indicating that green labeled NPs were co-localized with red stained mitochondria (FIG. 15c). The uncoated NPs (FIGS. 15d-15f) showed only green clusters indicating that the NPs were not co-localized within the mitochondria (FIG. 15f). Without wishing to being bound by theory, these results support the assumption that the PFK coating and the positive zeta-potential of the coated NPs were essential for targeting to mitochondria.

Example 11: Preparation of Uncoated and Coated Co-Assembled Peptide-Polypeptide Nanoparticles Comprising Pharmaceutically Active Ingredient (LND)

Lonidamine (LND) that is a negatively charged mildly amphiphilic molecule, was assumed to have favorable interactions with PFK (SEQ ID NO:2) under certain pH conditions and thus was used here to demonstrate the capacity of the NPs to carry a drug to the mitochondria. The NPs assembly procedure was adjusted to enable the incorporation of the drug by intermolecular interactions.

NPs loaded with LND (LND-NPs) were prepared by first mixing 1 ml of 0.5 mg/ml PFK (SEQ ID NO:2) with the same volume of 0.15 mg/ml LND aqueous solution. This LND and PFK solution was stirred using a magnetic stirrer overnight. One ml of 0.5 mg/ml γ-PGA was added to this solution followed by adjusting the pH to 7.4. The three components solution was stirred overnight then centrifuged at 3000 g for 20 min and lastly passed through a syringe driven 0.22 µm filter, to yield the LND-NPs solution.

LND-NPs average radius was found by DLS to be 8.6±2.4 nm with a negative surface zeta potential −24.1±6.9 mV (table 8).

The LND-NPs were further subjected to PFK coating (SEQ ID NO:2) in order to enhance their potential intracellular uptake and specific targeting to mitochondria PFK. In this system the peptide coating was applied with a concentrated PFK solution in one step to minimize the time the drug leakage off the LND-NPs, to the coating solution. Specifically, coated NPs loaded with LND were prepared by adding 1 ml of 2 mg/ml PFK aqueous solution (SEQ ID NO:2), intended to form the outer NP peptide coating (as described in Example 9) to 1 ml of the LND-NPs.

These NPs, (coated NPs), exhibited a larger average radius 13.7±5.4 nm, as compared to LND-NPs and had a positive surface charge of 15.1±5.8 mV (table 8).

TABLE 8

DLS and Zeta potential results of NPs loaded with LND and control NPs (n = 5).

|  | $R_h$ [nm] | $\xi$ [mV] |
| --- | --- | --- |
| LND-NPs | 8.6 ± 2.4 | −24.1 ± 6.9 |
| Coated LND-NPs | 13.7 ± 5.4 | 15.1 ± 5.8 |
| Control NPs | 5.9 ± 0.9 | −46.0 ± 3.6 |
| Control coated NPs | 46.7 ± 19.4 | 2.7 ± 2.3 |

A drug-free version of the LND-NPs was prepared in the same manner as LND-NPs. One ml of 0.5 mg/ml PFK (SEQ ID NO:2) was mixed with the same volume of 1 mM NaOH (representing the LND solution). The PFK and NaOH solution was then stirred using a magnetic stirrer overnight. This solution was supplemented with 1 ml γ-PGA, then acidified to pH 7.4 by aliquots of 0.1 M HCl. This solution was next stirred overnight, then centrifuged at 3000 g for 20 min and passed through a syringe driven 0.22 filtered µm filter, to yield the final drug deficient control for the LND-NPs solution. The drug deficient version of coated LND-NPs was prepared with 1 ml of drug deficient control for the LND-NPs, supplemented with 1 ml of 2 mg/ml PFK (SEQ ID NO:2) aqueous solution. Mean particle sizes a surface potentials of coated and uncoated control NPs are also presented in table 8.

The peptide and polypeptide contents of the LND-deficient, control coated NPs and coated LND-NPs were quantified by thermogravimetric measurements. The coated LND-NPs and the control coated NPs were prepared as described above, 3 ml of the NPs solutions were frozen in liquid nitrogen and then lyophilized (Free Zone Triad Cascade Benchtop Freeze Dry System, Labconc, Kansas, USA). The lyophilized powders were analyzed by thermogravimetric measurements (TGA, TA Instruments Q500, New Castle, Del., USA) with samples flushed by nitrogen at a flow rate of 90 ml/min and heated at 10° C./min to 1000° C. The coated LND-NPs and drug deficient coated NPs weight percentages were then calculated from the thermograms.

Figure 16A:
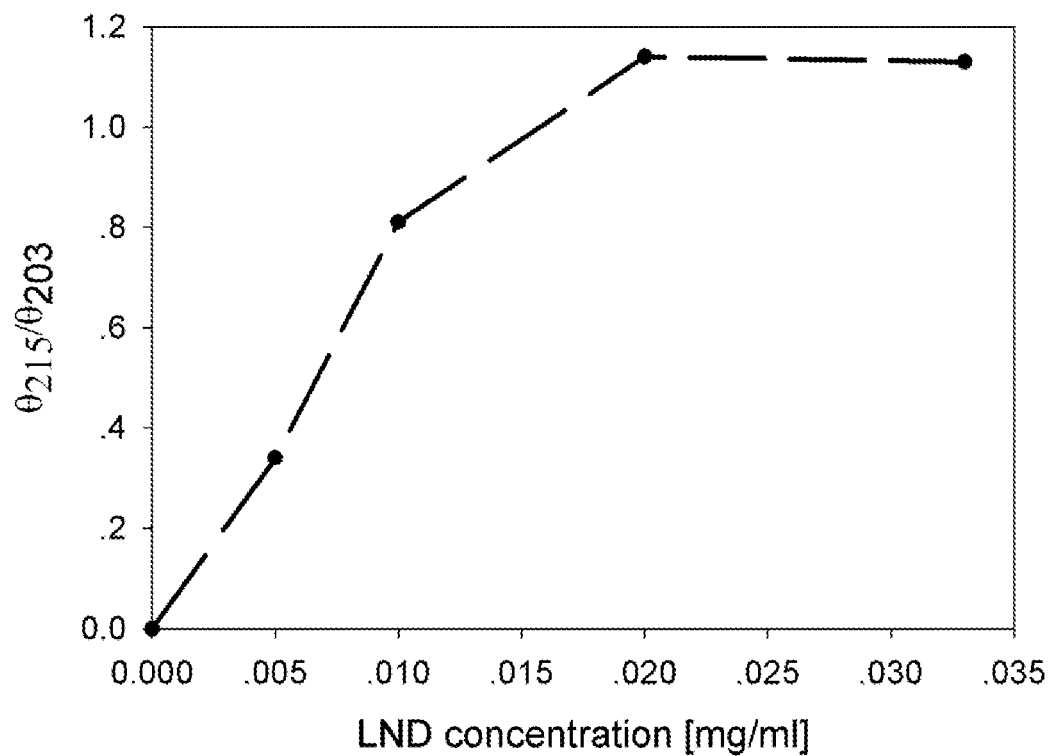
FIG. 16a shows fraction of β-sheet relative to unfolded structure ($\theta_{215}/\theta_{203}$) of 0.25 mg/ml PFK (SEQ ID NO:2) with LND as a function of LND concentration.
Figure 16B:
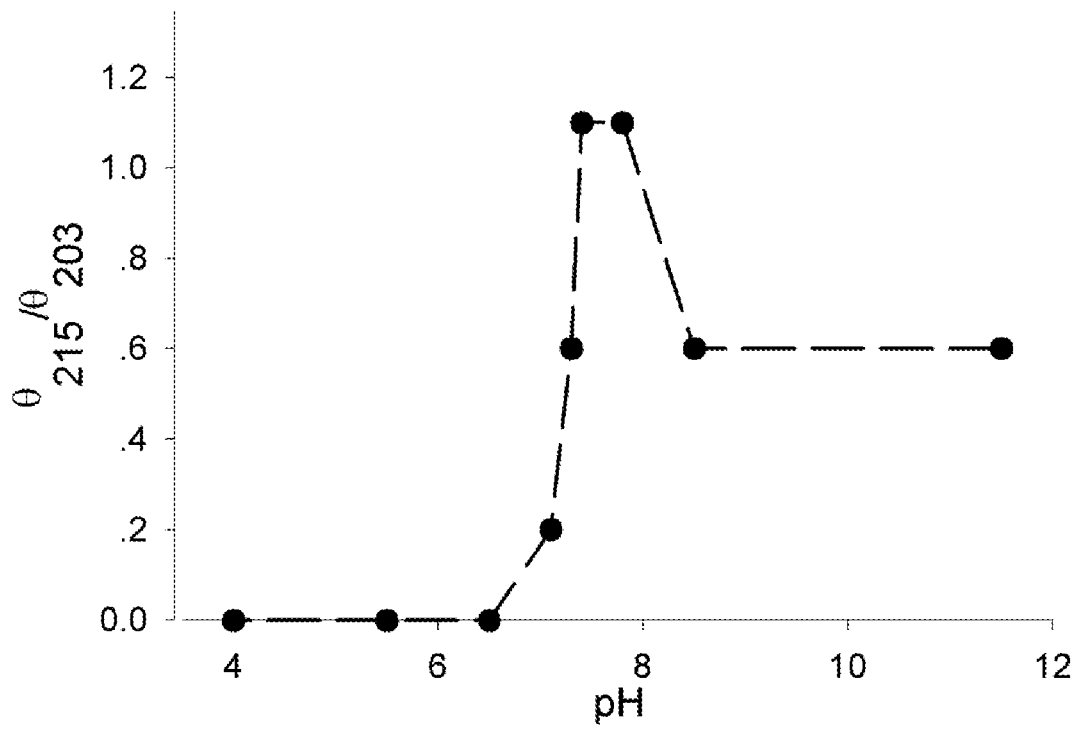
FIG. 16b shows fraction of β-sheet relative to unfolded structure ($\theta_{215}/\theta_{203}$) of 0.25 mg/ml PFK (SEQ ID NO:2) with 0.03 mg/ml LND as a function of pH.

The effect of LND concentration on PFK secondary structure (SEQ ID NO:2) was assessed by CD measurements, with the assumption that the LND interactions with the peptide will induce the later to assume the β-sheet conformation. PFK which exhibits unfolded structure at 0.5 mg/ml on mixing with LND at the range of concentrations examined (0.005-0.03 mg/ml) showed a negative absorbance at 215 nm, attributed to β-sheet secondary structure. The molar ellipticity absorption curves show a generally deeper spectrum with increased LND concentrations and increase in the $\theta_{215}/\theta_{203}$ ratio (FIG. 16*a*). The effect of pH on the conformation of PFK with LND was also assessed by CD measurements with the assumption that stable interactions would induce the peptide's β-sheet conformation. PFK and LND mixtures (0.25 and 0.03 mg/ml respectively) at pH 6.5 and 7.1 showed a positive peak at 220 nm, indicating unfolded secondary structure whereas at pH >7.4 the two distinct peaks at 215 nm and 203 nm, corresponding to β-sheet and unfolded structure were observed. This ratio then decreased at higher pH values suggesting that the β-sheet conformation and therefore the overall stability obtained by the interactions between these two components is most favorable at pH 7.4-7.8 (FIG. 16*b*). Based on these results it was hypothesized that the LND will be maintained within the NPs under mildly acidic pH conditions where the PFK and γ-PGA are co assembled, and will be released off at mildly basic pH where the NPs would become destabilized along with the weakening of the interactions between the drug and the peptide.

Example 12: The Pharmaceutically Active Ingredient (LND) Release from the Coated Co-Assembled Peptide-Polypeptide Nanoparticles Solution of coated LND-NPs, 1 ml sealed in dialysis tube (spectrapor 6 analysis membrane 1 KDa), was soaked in 5 ml of a release medium, stirred by magnetic stirrer at room temperature. The released LND was measured at 0.5, 1, 3, 6, and 24 hr (each time point was tested by three different dialysis tubes). Three different release media were tested: Tris buffer saline (TBS) at pH 7.4 and 8.5 (pH adjusted by aliquots of 1 M HCl) and citrate-saline buffer at pH 5. The LND content in coated LND-NPs solution remaining in the dialysis tube, was measured by spectrophotometer at a wavelength of 300 nm. The LND released from the LND-NPs is represented in percentages according to the formula: $(C_0-C_t/C_0)*100$, $C_0$ and $C_t$ are the concentrations of LND in the LND-NPs, at the beginning of the measurement and at the sampling time, respectively.

Figure 17:
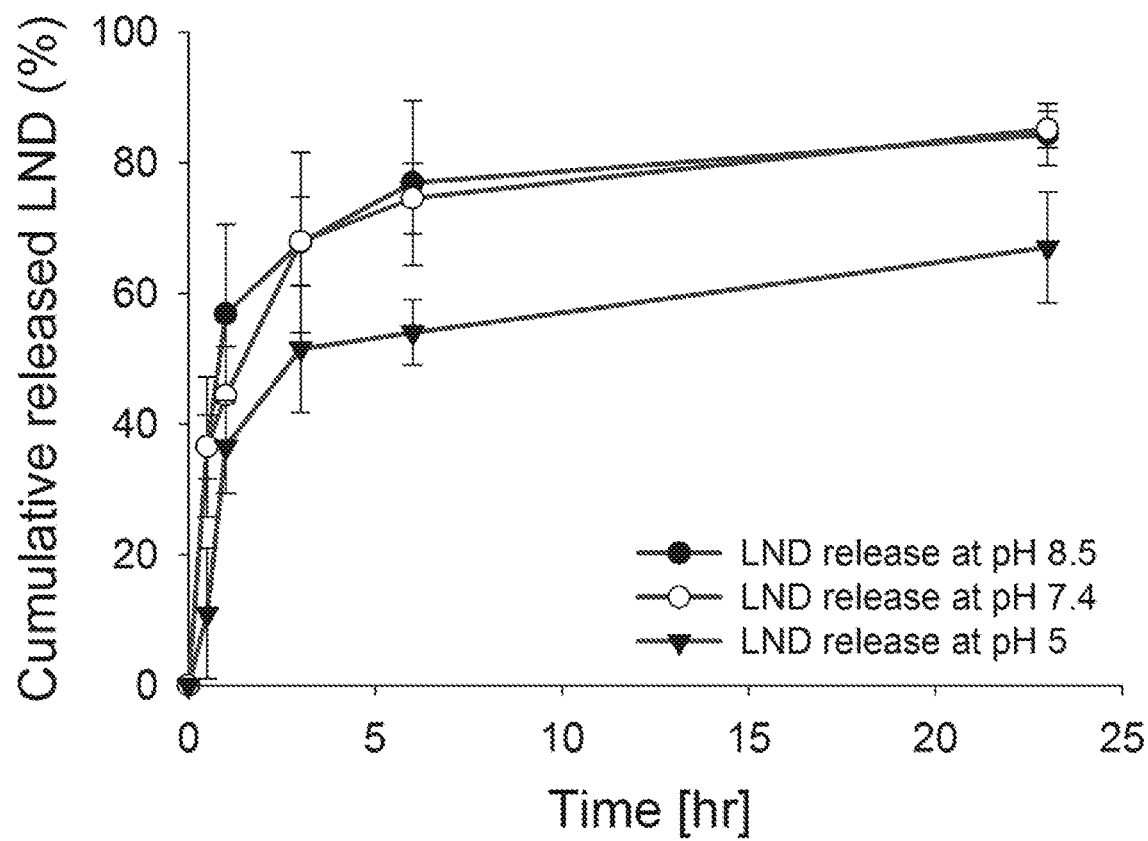
FIG. 17 shows cumulative releases of LND from the PFK (SEQ ID NO:2) coated γ-PGA-PFK nanoparticles comprising LND, at pH values of 5 (●), 7.4 (○), and 8.5 (▼).

The ability of LND-NPs to deliver the LND to the mitochondria was tested at pH=5, 7.4 and 8.5 corresponding to pH values representing endosome, cytoplasm and mitochondria, with the assumption that the drug should be withheld by the NPs under the mildly acidic conditions of the endosome and be released at the slightly basic pH of the mitochondria matrix (FIG. 17). Cumulative release measurements indicated that the drug release at pH 5 was indeed lower than that under natural and basic conditions (FIG. 17). There was ~65% release at pH 5 within 24 h compare to ~85% at pH 7.4 and 8.5, pointing to the strong effect of electrostatic interactions on stabilizing the LND within the NPs.

Example 13: Cytotoxicity of NPs Loaded

The cytotoxicity of coated nanoparticles was assessed by monitoring the viability of Saos2 cells in presence of the NPs. All cell cultured were carried in air supplemented with 5% $CO_2$ at 37° C. In 24 wells plate, $3*10^4$ cells/well were seeded, in DMEM complete medium and cultured for 4 h. The cells were supplemented with different concentrations of LND-NPs, control NPs, or free LND and cultured overnight. Cells viability was determined by XTT assay following the manufacturer instructions (Life Technologies, California, USA). The XTT solution was added to the wells and cells were incubated for 4 hr after which the absorbance of the samples was measured at 490 nm, by a microplate-reader (BioTek instruments, Winoosky, Vt.). Cells viability is reported as percentage compared to untreated cultured cells.

ATP Assay:

Cellular ATP levels were measured using a fluorometric ATP assay kit (ATP assay kit, Sigma-Aldrich) according to the manufacturer instructions. Briefly, Saos2 cells ($3*10^4$) were cultured for 4 h, in 24 wells plate with DMEM complete medium. Cells were cultured overnight in media supplemented with either coated LND-NPs, control coated NPs, or free LND (0.12 mg/ml NPs, 2.9 µM LND). Cells were then washed with PBS and lysed with 50 µL of ATP assay buffer, according to the manufacturer instructions. In 96-well plates, 50 µL of each supernatant was mixed with 50 µL ATP reaction mix. After 30 min incubation fluorescence was recorded by a microplate-reader (BioTek instruments, Winoosky, Vt.) at Ex=535 and Em=587 nm. ATP levels are represented as normalized values compared to untreated cells.

Figure 18A:
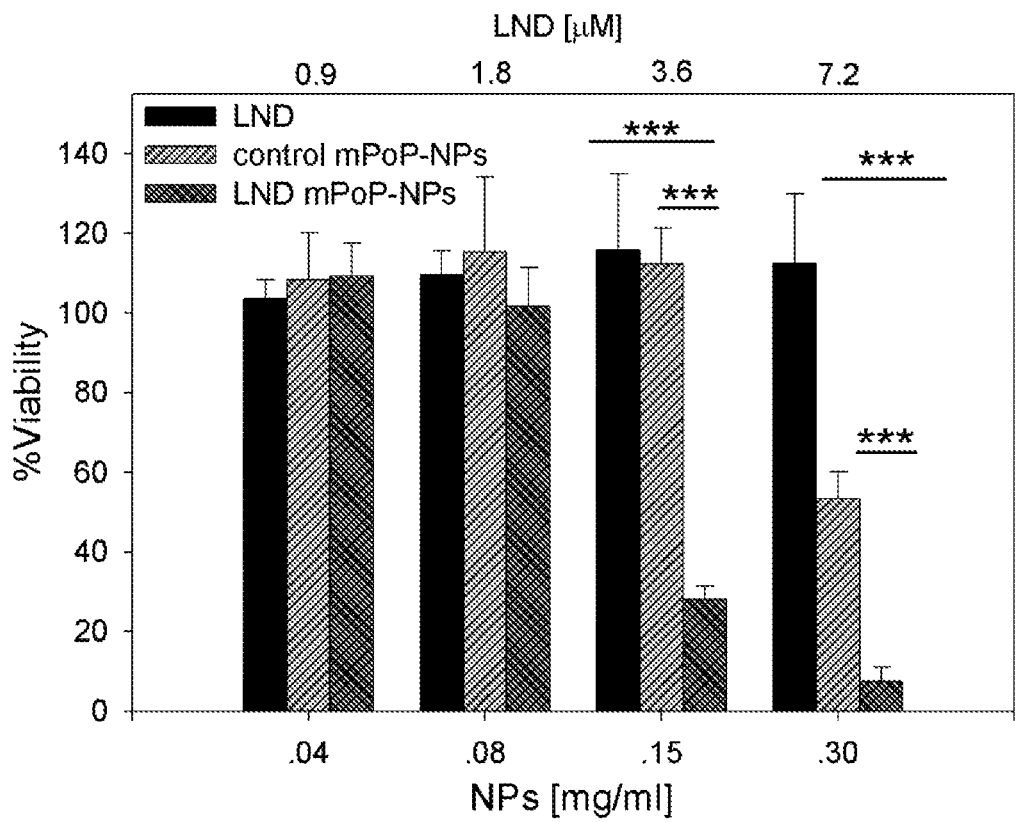
FIG. 18a shows cell viability of Saos2 human osteosarcoma cancer cells in the presence of the PFK (SEQ ID NO:2) coated γ-PGA nanoparticles comprising LND (checker board bar), control PFK coated γ-PGA-PFK nanoparticles (diagonal stripes bar), and free LND (solid color bar) at different concentrations following overnight incubation. Cell viability was normalized by setting the viability of untreated cells as 100%.
Figure 18B:
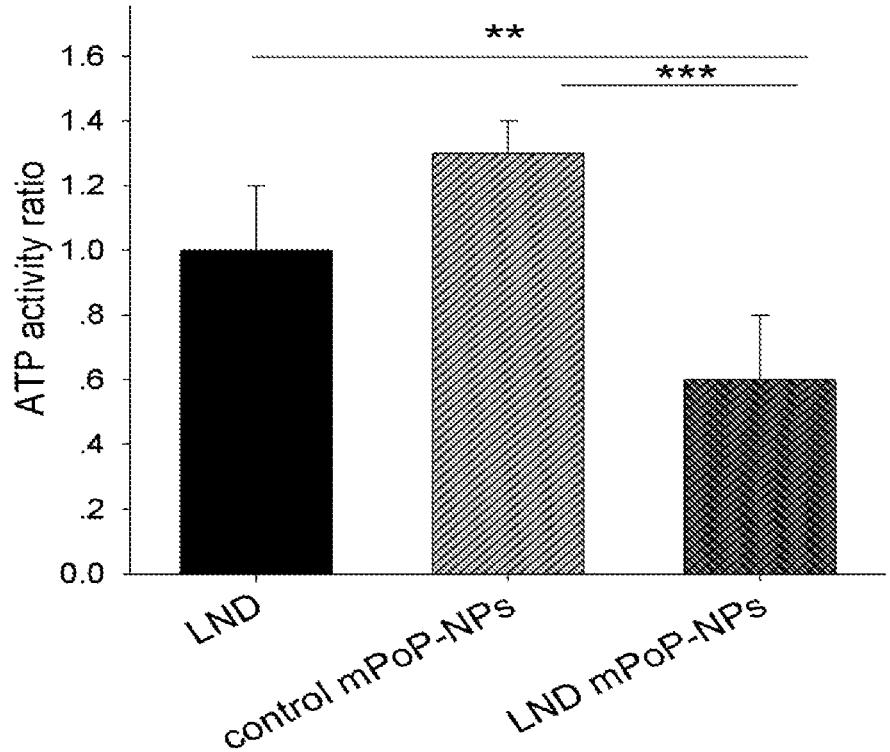
FIG. 18b shows ATP activity ratio of Saos2 cells treated with the PFK (SEQ ID NO:2) coated γ-PGA-PFK nanoparticles comprising LND (checker board bar), control PFK coated γ-PGA nanoparticles (diagonal stripes bar), and free LND (solid color bar) (2.9 μM LND, 0.12 mg/ml NPs). $P<0.05$ *$P<0.001$, (n=5).

The results of the cytotoxicity of coated LND-NPs, control coated NPs, or free LND are presented in FIG. 18a. A significant decrease in the cell viability was observed for cells treated with coated LND-NPs with $IC_{50}=3.7\pm0.6$ µM, that is 350 times lower than the $IC_{50}$ value of free LND measured with the Saos2 cultures to be 1.3 mM (results not shown). This indicates that the coated LND-NPs significantly enhanced drug efficacy but possibly also elicited toxicity induced by the coated NPs properties. Indeed, the control coated NPs also had an effect on cell survival however at higher NPs concentrations; at NPs concentration 0.15 mg/ml cells survival was 28.2 and 107.3%, for coated LND-NPs and for control coated NP treatments, respectively. In order to assess the effect of LND on ATP production in Saos2 cells, ATP levels where measured in cells supplemented with free LND, coated LND-NPs and control coated NPs (FIG. 18b). Coated LND-NPs lead to a significant decrease in ATP levels compared with the free LND and control coated NPs.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A co-assembled nanoparticle comprising:
   at least one polypeptide comprising a polyanion; and
   at least one amphiphilic peptide capable of forming a β-sheet structure, a derivative or a salt thereof, the amphiphilic peptide comprising at least 2 pairs of alternating hydrophobic/hydrophilic amino acid residues, wherein the hydrophilic amino acid residue is positively charged.

2. The co-assembled nanoparticle of claim 1, wherein the at least one amphiphilic peptide comprises at least one terminal Pro residue.

3. The co-assembled nanoparticle of claim 1, wherein the at least one amphiphilic peptide is 4-40 amino acids in length.

4. The co-assembled nanoparticle of claim 1, wherein the hydrophobic amino acid residue is selected from the group consisting of Phe, Leu, Ile, Val, Trp and Ala and the hydrophilic amino acid residue is selected from the group consisting of Lys and Arg.

5. The co-assembled nanoparticle of claim 4, wherein the hydrophobic amino acid residue is Phe and the hydrophilic amino acid residue is Lys.

6. The co-assembled nanoparticle of claim 1, wherein the at least one amphiphilic peptide comprises an amino acid sequence according to Formula I:

X-(hydrophobic-hydrophilic)$_n$-B        (Formula I)

wherein n designates an integer of 2-20, hydrophobic designates a hydrophobic amino acid residue, hydrophilic designates a hydrophilic amino acid residue, X designates Pro, Pro-hydrophilic amino acid residue or represents the peptide's amino terminus, and B is Pro or represents the peptide's carboxy terminus.

7. The co-assembled nanoparticle of claim 6, wherein the at least one amphiphilic peptide comprises an amino acid selected from the group consisting of SEQ ID NO:2, SEQ ID NO:4, SEQ ID NO:6, SEQ ID NO:10, and SEQ ID NO:12.

8. The co-assembled nanoparticle of claim 1, wherein the polypeptide comprises at least 70% polyanion.

9. The co-assembled nanoparticle of claim 1, wherein the polypeptide is a poly(gamma-glutamic acid).

10. The co-assembled nanoparticle of claim 1, wherein the weight ratio between the peptide and the polypeptide is from about 0.2:1 to about 2:1.

11. The co-assembled nanoparticle of claim 1, further comprising an outer coating.

12. The co-assembled nanoparticle of claim 11, wherein the outer coating comprises at least one amphiphilic peptide comprising at least 2 pairs of alternating hydrophobic/hydrophilic amino acid residues, wherein the hydrophilic amino acid residue is positively charged.

13. The co-assembled nanoparticle of any one of claim 11, wherein the outer coating comprises at least one amphiphilic peptide comprising an amino acid sequence according to Formula II:

Y1m$_1$-(hydrophobic-hydrophilic)n-Y2m$_2$        (Formula II)

wherein m$_1$ and m$_2$ designate an integer, which can independently be selected from 1 to 10, n designates an integer of 2-20, hydrophobic designates a hydrophobic amino acid residue, hydrophilic designates a hydrophilic amino acid residue, Y1 designates a hydrophobic amino acid residue, Pro, Pro-hydrophilic amino acid residue or represents the coating peptide's amino terminus, and Y2 designates a hydrophobic amino acid residue, Pro, Pro-hydrophilic amino acid residue or represents the amphiphilic peptide's carboxy terminus.

14. The co-assembled nanoparticle of claim 11, wherein the outer coating comprises at least one amphiphilic peptide, which is identical to the at least one amphiphilic peptide forming the co-assembled nanoparticle.

15. The co-assembled nanoparticle of claim 1, having a spherical shape; or a mean particle size in the range of about 10-100 nm; or a zeta potential above about 0 mV.

16. A pharmaceutical composition for the intracellular delivery comprising a plurality of the co-assembled nanoparticles of claim 1 and a pharmaceutically active ingredient selected from the group consisting of chemotherapeutic agents, mitochondria-acting agents, active proteins and combinations thereof.

17. The pharmaceutical composition of claim 16, wherein the pharmaceutically active ingredient is selected from the group consisting of Doxorubicin, Dequalinium, Lonidamine, and combinations thereof.

18. A method of treating a proliferative disease or mitochondrial dysfunction, said method comprising administering to a subject in need thereof a therapeutically effective amount of the pharmaceutical compositing of claim 16.

19. A method of preparing the co-assembled nanoparticle of claim 1, the method comprising the following steps:

(i) providing a liquid solution comprising at least one amphiphilic peptide of 4-40 amino acids comprising at least 2 pairs of alternating hydrophobic/hydrophilic amino acid residues, or a derivative or a salt thereof, capable of forming a β-sheet structure, in a vessel;

(ii) providing an alkaline solution comprising a polypeptide comprising polyanion;

(iii) mixing together the peptide solution and the polypeptide solution;

(iv) acidifying the solution obtained in step iii;

(v) stirring for at least about 8 hours; and optionally further comprising a step of adding a solution comprising an additional amphiphilic peptide of 4-40 amino acids comprising at least 2 pairs of alternating hydrophobic/hydrophilic amino acid residues, or a derivative or a salt thereof, capable of forming a β-sheet structure, wherein said step is repeated at least twice.

20. The method of claim 19, further comprising a step of mixing a solution comprising a pharmaceutically active ingredient with the peptide solution and/or a polypeptide solution, wherein a portion of the solution comprising a pharmaceutically active ingredient is mixed with the polypeptide solution and a portion the solution comprising a pharmaceutically active ingredient is mixed with the polypeptide solution prior to step iii.

* * * * *

SEQUENCE LISTING

```
<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Phe Lys Phe Lys Phe Lys Phe Lys Phe Lys Phe Lys Phe
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Pro Lys Phe Lys Phe Lys Phe Lys Phe Lys Phe Lys Pro
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Phe Lys Phe Lys Phe Lys Phe Lys Phe Lys Phe
1               5                   10

<210> SEQ ID NO 4
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Pro Lys Phe Lys Phe Lys Phe Lys Phe Lys Pro
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Phe Lys Phe Lys Phe Lys Phe Lys Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Pro Lys Phe Lys Phe Lys Phe Lys Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Phe Lys Phe Lys Phe Lys Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Pro Lys Phe Lys Phe Lys Pro
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Phe Lys Phe Lys Phe Lys Phe Lys Phe Lys Phe Lys Phe Lys Phe
1               5                   10                  15

<210> SEQ ID NO 10
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 10

Pro Lys Phe Lys Phe Lys Phe Lys Phe Lys Phe Lys Phe Lys Pro
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Phe Lys Phe Lys Phe Lys Phe Lys Phe Lys Phe Lys Phe Lys Phe Lys
1               5                   10                  15

Phe

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Pro Lys Phe Lys Phe Lys Phe Lys Phe Lys Phe Lys Phe Lys Phe Lys
1               5                   10                  15

Pro

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Leu Leu Leu Leu Phe Lys Phe Lys Phe Lys Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Leu Leu Leu Leu Leu Phe Lys Phe Lys Phe Lys Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide

<400> SEQUENCE: 15

Leu Leu Leu Leu Leu Leu Phe Lys Phe Lys Phe Lys Pro
1               5                   10
```

```
<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Lys Phe Phe Pro Lys Lys Pro Phe Lys Phe Phe Lys Lys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide

<400> SEQUENCE: 17

Lys Phe Phe Phe Lys Lys Phe Phe Lys Phe Phe Lys Lys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (1)..(1)
<223> OTHER INFORMATION: Leu can be repeated 2-6 times

<400> SEQUENCE: 18

Leu Phe Lys Phe Lys Phe Lys Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (9)..(9)
<223> OTHER INFORMATION: Leu can be repeated 2-6 times

<400> SEQUENCE: 19

Pro Lys Phe Lys Phe Lys Phe Lys Leu
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (11)..(11)
<223> OTHER INFORMATION: Leu can be repeated 2-6 times

<400> SEQUENCE: 20

Pro Lys Phe Lys Phe Lys Phe Lys Phe Lys Leu
1               5                   10

<210> SEQ ID NO 21
```

```
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: REPEAT
<222> LOCATION: (13)..(13)
<223> OTHER INFORMATION: Leu can be repeated 2-6 times

<400> SEQUENCE: 21

Pro Lys Phe Lys Phe Lys Phe Lys Phe Lys Phe Lys Leu
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (15)..(15)
<223> OTHER INFORMATION: Leu can be repeated 2-6 times

<400> SEQUENCE: 22

Pro Lys Phe Lys Phe Lys Phe Lys Phe Lys Phe Lys Phe Lys Leu
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (17)..(17)
<223> OTHER INFORMATION: Leu can be repeated 2-6 times

<400> SEQUENCE: 23

Pro Lys Phe Lys Phe Lys Phe Lys Phe Lys Phe Lys Phe Lys Phe Lys
1               5                   10                  15

Leu

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (1)..(1)
<223> OTHER INFORMATION: Leu can be repeated 2-6 times

<400> SEQUENCE: 24

Leu Phe Lys Phe Lys Phe Lys Phe Lys Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (1)..(1)
<223> OTHER INFORMATION: Leu can be repeated 2-6 times
```

```
<400> SEQUENCE: 25

Leu Phe Lys Phe Lys Phe Lys Phe Lys Phe Lys Pro
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (1)..(1)
<223> OTHER INFORMATION: Leu can be repeated 2-6 times

<400> SEQUENCE: 26

Leu Phe Lys Phe Lys Phe Lys Phe Lys Phe Lys Phe Lys Pro
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: REPEAT
<222> LOCATION: (1)..(1)
<223> OTHER INFORMATION: Leu can be repeated 2-6 times

<400> SEQUENCE: 27

Leu Phe Lys Phe Lys Phe Lys Phe Lys Phe Lys Phe Lys Phe Lys Pro
1               5                   10                  15
```